(12) United States Patent
Yan et al.

(10) Patent No.: US 11,535,631 B2
(45) Date of Patent: Dec. 27, 2022

(54) THIOPHENE END GROUPS OF NON-FULLERENE ACCEPTORS FOR ELECTRONIC AND PHOTONIC APPLICATIONS

(71) Applicant: The Hong Kong University of Science and Technology, Hong Kong (CN)

(72) Inventors: He Yan, Hong Kong (CN); Jianquan Zhang, Hong Kong (CN)

(73) Assignee: The Hong Kong University of Science and Technology, Hong Kong (HK)

( * ) Notice: Subject to any disclaimer, the term of this patent is extended or adjusted under 35 U.S.C. 154(b) by 203 days.

(21) Appl. No.: 16/862,676

(22) Filed: Apr. 30, 2020

(65) Prior Publication Data

US 2020/0347077 A1 Nov. 5, 2020

Related U.S. Application Data

(60) Provisional application No. 62/920,446, filed on May 1, 2019.

(51) Int. Cl.
*C07D 495/22* (2006.01)
*H01L 51/42* (2006.01)

(52) U.S. Cl.
CPC .......... *C07D 495/22* (2013.01); *H01L 51/424* (2013.01); *H01L 51/428* (2013.01)

(58) Field of Classification Search
CPC ............. H01L 51/0036; H01L 51/0037; H01L 51/0043; H01L 51/424; H01L 51/428; H01L 51/4253; C07D 495/22
See application file for complete search history.

(56) References Cited

U.S. PATENT DOCUMENTS

2018/0366668 A1* 12/2018 Barr ...................... H01L 51/424

FOREIGN PATENT DOCUMENTS

| CN | 106883247 A | 6/2017 | |
|---|---|---|---|
| CN | 108164547 A | 6/2018 | |
| CN | 108864142 A | 11/2018 | |
| CN | 109694464 A * | 4/2019 | ......... H01L 51/0036 |

OTHER PUBLICATIONS

Zhao et al, Molecular Optimization Enables over 13% Efficiency in Organic Solar Cells, J. Am. Chem. Soc. 2017, 139, 7148-7151. (Year: 2017).*

Cui et al, Fine-Tuned Photoactive and Interconnection Layers for Achieving over 13% Efficiency in a Fullerene-Free Tandem Organic Solar Cell, J. Am. Chem. Soc. 2017, 139, 7302-7309. (Year: 2017).*

(Continued)

*Primary Examiner* — Andrew J Golden
(74) *Attorney, Agent, or Firm* — S&F/WEHRW

(57) ABSTRACT

Provided herein are small molecular acceptor compounds containing thiophene end groups, methods for their preparation and intermediates used therein, the use of formulations containing the same as semiconductors in organic electronic devices, especially in organic photovoltaic and organic field-effect transistor devices, and to organic electronic and organic photovoltaic devices made from these formulations.

11 Claims, 11 Drawing Sheets

(a)

(b)

(c)

(56) References Cited

OTHER PUBLICATIONS

Aldrich et al, Fluorination Effects on Indacenodithienothiophene Acceptor Packing and Electronic Structure, End-Group Redistribution, and Solar Cell Photovoltaic Response, J. Am. Chem. Soc. Jan. 2019, 141, 3274-3287. (Year: 2019).*
Ye et al, High-Efficiency Nonfullerene Organic Solar Cells: Critical Factors that Affect Complex Multi-Length Scale Morphology and Device Performance, Adv. Energy Mater. 2017, 7, 1602000 (Year: 2017).*
Sun et al, Dithieno[3,2-b:2',3'-d]pyrrol Fused Nonfullerene Acceptors Enabling Over 13% Efficiency for Organic Solar Cells, Adv. Mater. 2018, 30, 1707150. (Year: 2018).*
Zhang et al, Over 14% Efficiency in Organic Solar Cells Enabled by Chlorinated Nonfullerene Small-Molecule Acceptors, Adv. Mater. 2018, 30, 1800613 (Year: 2018).*
Lin et al, A Facile Planar Fused-Ring Electron Acceptor for As-Cast Polymer Solar Cells with 8.71% Efficiency, J. Am. Chem. Soc. 2016, 138, 2973-2976. (Year: 2016).*
Feng et al, Fused-Ring Acceptors with Asymmetric Side Chains for High-Performance Thick-Film Organic Solar Cells, Adv. Mater. 2017, 29, 1703527. (Year: 2017).*
Gao et al, Side Group Engineering of Small Molecular Acceptors for High-Performance Fullerene-Free Polymer Solar Cells: Thiophene Being Superior to Selenophene, Adv. Funct. Mater. 2017, 27, 1702194. (Year: 2017).*
Yu et al, Conformation Locking on Fused-Ring Electron Acceptor for High-Performance Nonfullerene Organic Solar Cells, Adv. Funct. Mater. 2018, 28, 1705095. (Year: 2018).*
Luo et al, Side-Chain Impact on Molecular Orientation of Organic Semiconductor Acceptors: High Performance Nonfullerene Polymer Solar Cells with Thick Active Layer over 400 nm, Jun. 2018, Adv. Energy Mater. 2018, 8, 1800856 (Year: 2018).*
Luo et al, Fine-Tuning of Molecular Packing and Energy Level through Methyl Substitution Enabling Excellent Small Molecule Acceptors for Nonfullerene Polymer Solar Cells with Efficiency up to 12.54%, Jan. 2018, Adv. Mater. 2018, 30, 1706124 (Year: 2018).*
Xie et al, A Novel Thiophene-Fused Ending Group Enabling an Excellent Small Molecule Acceptor for High-Performance Fullerene-Free Polymer Solar Cells with 11.8% Efficiency, May 2017, Sol. RRL 2017, 1, 1700044 (Year: 2017).*
Luo et al, Reduced Energy Loss Enabled by a Chlorinated ThiopheneFused Ending-Group Small Molecular Acceptor for Efficient Nonfullerene Organic Solar Cells with 13.6% Efficiency, Mar. 2019, Adv. Energy Mater. 2019, 9, 1900041 (Year: 2019).*
Li et al, Systematic investigation of methyl substitution effect on physicochemical properties and photovoltaic performance in nonfullerene small-molecule electron acceptors, Jan. 2019, Dyes and Pigments 164 (2019) 126-132 (Year: 2019).*
Xie et al, A new small molecule acceptor based on indaceno[2,1-b:6,5-b']dithiophene and thiophene-fused ending group for fullerene-free organic solar cells, Sep. 2017, Dyes and Pigments 148 (2018) 263-269 (Year: 2017).*
EIC 1700 STIC structure search results (Year: 2022).*
CN 109694464A English machine translation (Year: 2019).*
Luo et al, Reduced Energy Loss Enabled by a Chlorinated ThiopheneFused Ending-Group Small Molecular Acceptor for Efficient Nonfullerene Organic Solar Cells with 13.6% Efficiency, Adv. Energy Mater. 2019, 9, 1900041 (Year: 2019).*
Sun, Jia, et al. "High performance non-fullerene polymer solar cells based on PTB7-Th as the electron donor with 10.42% efficiency." Journal of Materials Chemistry A 6.6 (2018): 2549-2554.
Yao, Huifeng, et al. "Achieving Highly Efficient Nonfullerene Organic Solar Cells with Improved Intermolecular Interaction and Open-Circuit Voltage." Advanced Materials 29.21 (2017): 1700254.
Office Action of CN 202010369781.7 issued from from the China National Intellectual Property Administration (CNIPA) dated Sep. 5, 2022.
Zhenghui Luo et al., Adv. Energy Mater, Reduced Energy Loss Enabled by a Chlorinated Thiophene-Fused Ending-Group Small Molecular Acceptor for Efficient Nonfullerene Organic Solar Cells with 13.6% Efficiency, published on Mar. 18, 2019.
Hao Zhang et al., Adv. Mater., Over 14% Efficiency in Organic Solar Cells Enabled by Chlorinated Nonfullerene Small-Molecule Acceptors, published on May 28, 2018.
Zhenghui Luo et al., Nano Energy, Significantly improving the performance of polymer solar cells by the isomeric ending-group based small molecular acceptors: Insight into the isomerization, published on Oct. 3, 2019.
Jianquan Zhang et al., Chem. Mater., Chlorinated Thiophene End Groups for Highly Crystalline Alkylated Non-Fullerene Acceptors toward Efficient Organic Solar Cells, published on Jun. 17, 2019.
Zhenghui Luo et al., Adv. Energy Mater., Side-Chain Impact on Molecular Orientation of Organic Semiconductor Acceptors: High Performance Nonfullerene Polymer Solar Cells with Thick Active Layer over 400 nm, published on Jun. 21, 2018.

* cited by examiner

THIOPHENE END GROUPS OF NON-FULLERENE ACCEPTORS FOR ELECTRONIC AND PHOTONIC APPLICATIONS

CROSS-REFERENCE TO RELATED APPLICATIONS

This application claims the benefit of priority of U.S. Provisional Application No. 62/920,446, filed on May 1, 2019, the contents of which being hereby incorporated by reference in their entirety for all purposes.

TECHNICAL FIELD

The present disclosure relates to n-type organic semiconductors based on thiophene end groups, methods for their preparation and intermediates used therein, the use of formulations containing such organic semiconductors as the electron acceptors in organic solar cells (OSCs) or other optoelectronic (OE) devices and OSC devices made from these formulations.

BACKGROUND

The organic solar cell (OSC) is considered a promising low-cost and environmentally friendly solar technology, as it can be produced using low-cost printing methods and does not contain any toxic components.

Rapid advances in developing novel electron-donating and electron-withdrawing building blocks have given rise to a variety of donor and acceptor materials with tunable optical, electronic and morphological properties, which has boosted the power conversion efficiencies (PCE) of non-fullerene OSCs to beyond 15%.

Among these achievements, acceptor-donor-acceptor (A-D-A) small molecular acceptors (SMAs), where an electron-rich conjugated core is flanked by two electron-deficient end groups, have attracted considerable attention in the OSC field and brought a "paradigm shift" from fullerene devices to non-fullerene devices. Compared to fullerene derivatives, A-D-A SMAs possess synthetic accessibility, tunable absorption and energy levels, and favorable molecular packing, which can be achieved by proper combinations between the central cores and the end groups.

End group engineering plays a crucial role in developing high-performing SMAs. Theoretical calculations indicate that end groups can greatly affect the LUMO levels of A-D-A SMAs and thereby the open-circuit voltage (VOC) of the devices. In addition, the molecular packing of A-D-A SMAs largely relies on the $\pi$-$\pi$ stacking of the end groups, meaning that closely stacked end groups facilitate electron transport.

For instance, A-D-A SMAs flanked with the thiophene-based end groups exhibit shorter $\pi$-$\pi$ stacking distances than corresponding analogs flanked with the benzene-based end groups, resulting in enhanced electron mobilities and fill factors (FF) of the devices. Whereas, the more electron-rich thiophene rings weaken the intramolecular charge transfer (ICT) effect between the core and the end groups, which causes a blue-shifted absorption and a decreased extinction coefficient of the acceptor, and thus an inferior short-circuit current density (JSC).

In view of the foregoing, there exists a need for improved A-D-A SMAs and optoelectronics comprising the same with improved performance, lifetime, and the efficiencies.

SUMMARY

Provided herein are substituted thiophene end groups for constructing A-D-A acceptors. The use of unsubstituted thiophene end groups is widely believed to be harmful to the light absorption of the A-D-A acceptors, and therefore the JSC of the OSC devices. There are few reports on unsubstituted thiophene end groups that can achieve good device performance, which is mainly due to the electron-rich nature of the thiophene ring and the weak ICT effects induced by unsubstituted thiophene end groups.

As described in greater detail herein, it was surprisingly discovered that when the A-D-A acceptors comprising thiophene end groups are substituted with, e.g., one or more halogenated atoms or alkyl groups, the resulting A-D-A acceptors show simultaneously enhanced JSC and FF in the OSC devices. Without wishing to be bound by theory, it hypothesized that there are mainly two reasons for such improvement in device performances. First, the halogen atoms endow the thiophene-based end groups with stronger electron-withdrawing ability relative to their non-halogenated counterparts due to the strong electronegativity, which extends the absorption range and enhances extinction coefficients. On the other hand, halogenated molecules have been shown to facilitate molecular packing induced by noncovalent interactions, which further promotes efficient electron transport.

In a first aspect, provided herein is a compound of Formula 1:

wherein $Ar^1$ is selected from the group consisting of:

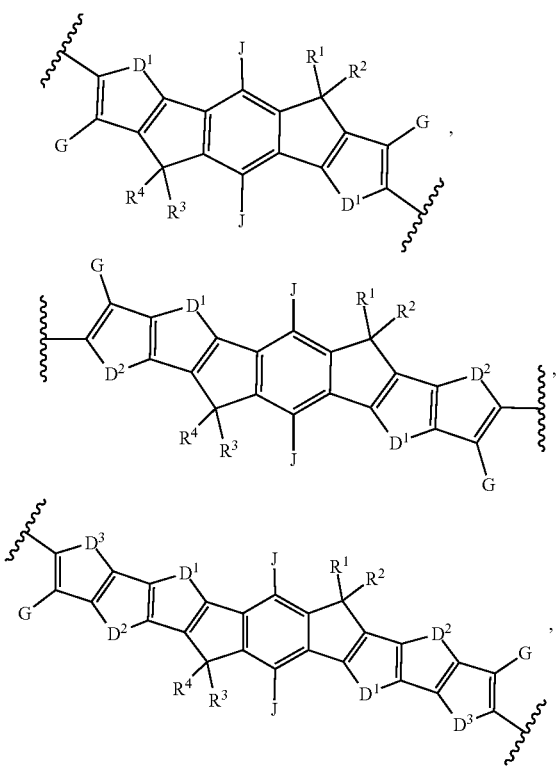

-continued

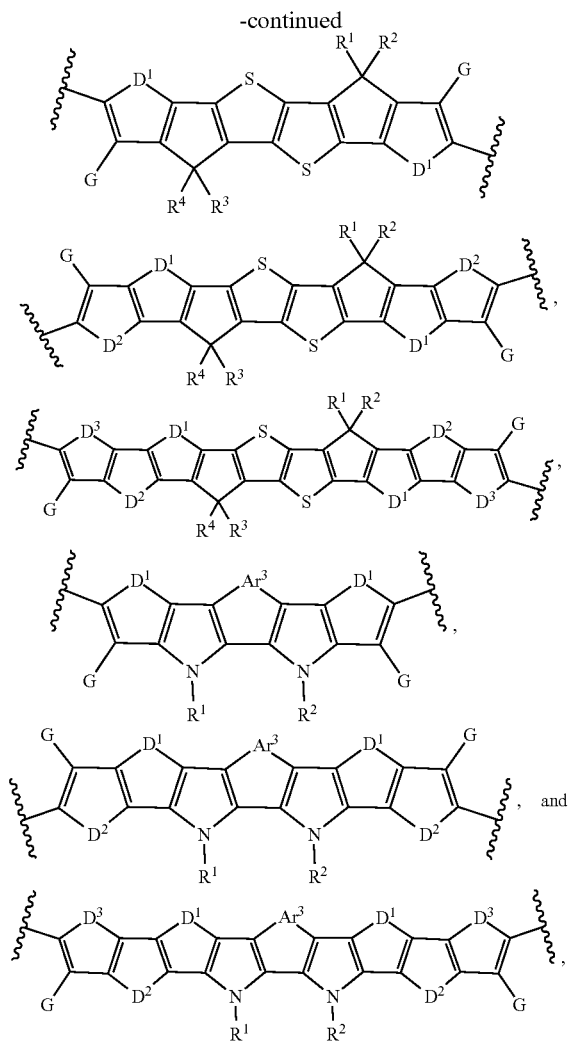

wherein each of $R^1$, $R^2$, $R^3$, and $R^4$ is independently an alkyl group selected from the group consisting of $C_2$-$C_{40}$ straight-chain alkyl, $C_3$-$C_{40}$ branched alkyl, $C_3$-$C_{40}$ cyclic alkyl, $C_2$-$C_{40}$ alkyl aryl, and $C_2$-$C_{40}$ alkyl heteroaryl, wherein one or more non-adjacent C atoms of the alkyl group are optionally replaced by —O—, —S—, —(C=O)—, —C(=O)O—, —OC(=O)—, —O(C=O)O—, —CR=CR—, or —C≡C—, and wherein one or more hydrogen atoms of the alkyl group are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups;

each of $D^1$, $D^2$, and $D^3$ is independently selected from the group consisting of —O—, —S—, —Se—, —Te—, —(NR)—, and —C(R)$_2$—;

each of J and G for each occurrence is independently selected from the group consisting of hydrogen, F, Cl, Br, CN, OR, NHR, N(R)$_2$, and an alkyl group selected from the group consisting of $C_2$-$C_{40}$ straight-chain alkyl, $C_3$-$C_{40}$ branched alkyl, $C_3$-$C_{40}$ cyclic alkyl, $C_2$-$C_{40}$ alkyl aryl, and $C_2$-$C_{40}$ alkyl heteroaryl, wherein one or more non-adjacent C atoms of the alkyl group are optionally replaced by —O—, —S—, —(C=O)—, —C(=O)O—, —OC(=O)—, —O(C=O)O—, —CR=CR—, or —C≡C—, and wherein one or more H atoms of the alkyl group are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups;

$Ar^3$ is selected from the group consisting of:

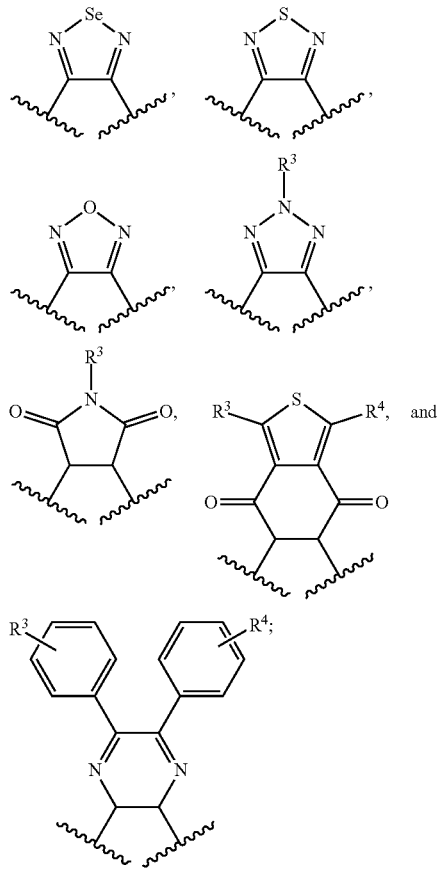

$Ar^2$ is selected from the group consisting of:

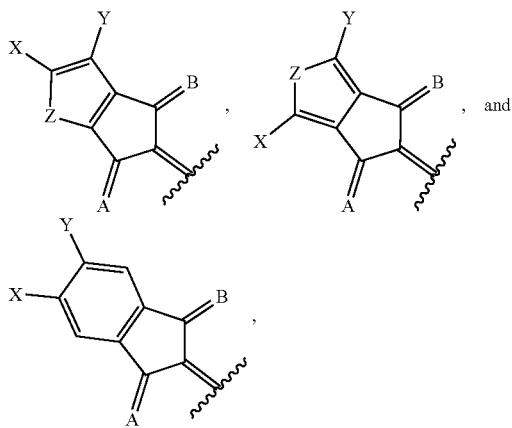

wherein A and B for each occurrence is independently selected from the group consisting of:

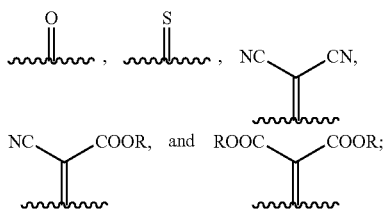

X and Y for each occurrence is independently selected from the group consisting of hydrogen, F, Cl, Br, I, CN, SCN, and alkyl;

Z for each occurrence is independently selected from the group consisting of —O—, —S—, —Se—, —Te—, and —(NR)—; and R for each occurrence is independently straight-chain alkyl, branched alkyl, or cyclic alkyl, with the proviso that if $Ar^2$ is:

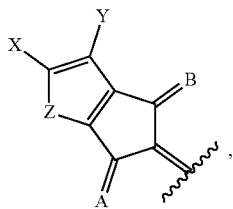

then no more than 1 instance of X or Y is hydrogen.

In a first embodiment of the first aspect, provided herein is the compound of the first aspect, wherein X is F, Cl, Br or methyl; Y is hydrogen; and Z is —S—; or each of X and Y is F, Cl, or Br and Z is —S—; or each of X and Y is hydrogen and Z is —S—.

In a second embodiment of the first aspect, provided herein is the compound of the first embodiment of the first aspect, wherein each of $D^1$, $D^2$, and $D^3$ is —S—.

In a third embodiment of the first aspect, provided herein is the compound of the second embodiment of the first aspect, wherein $Ar^1$ is selected from the group consisting of:

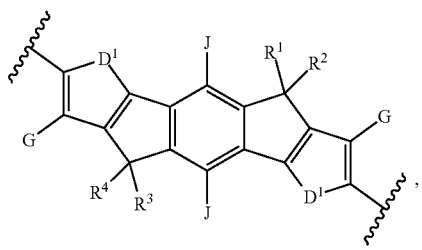

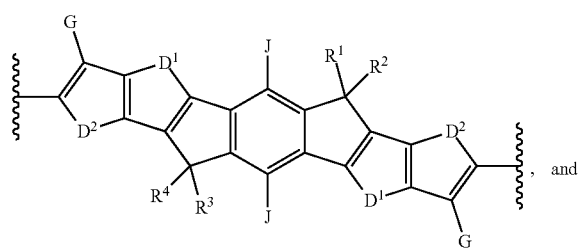

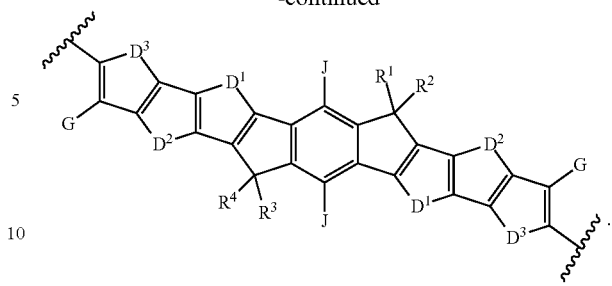

In a fourth embodiment of the first aspect, provided herein is the compound of the third embodiment of the first aspect, wherein J is hydrogen or an alkyl group; and G is hydrogen, F, Cl, or methyl group.

In a fifth embodiment of the first aspect, provided herein is the compound of the fourth embodiment of the first aspect, wherein A and B is independently selected from:

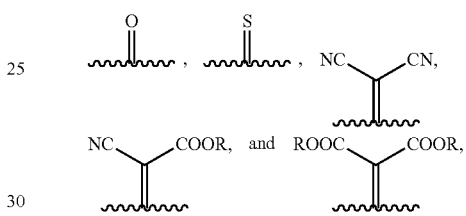

with the proviso that at least one of A or B is

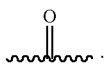

In a sixth embodiment of the first aspect, provided herein is the compound of the fifth embodiment of the first aspect, wherein each of $R^1$, $R^2$, $R^3$, and $R^4$ is an alkyl group selected from the group consisting of $C_2$-$C_{40}$ straight-chain alkyl, $C_3$-$C_{40}$ branched alkyl, $C_3$-$C_{40}$ cyclic alkyl, $C_2$-$C_{40}$ alkyl aryl, and $C_2$-$C_{40}$ alkyl heteroaryl.

In a seventh embodiment of the first aspect, provided herein is the compound of the first aspect, wherein A and B is independently selected from the group consisting of:

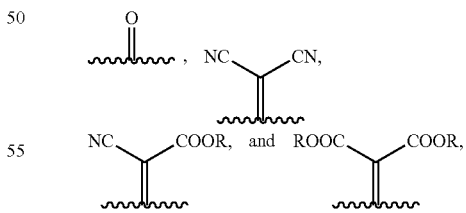

with the proviso that at least one of A or B is

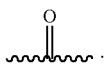

In an eighth embodiment of the first aspect, provided herein is the compound of the first aspect, wherein A is:

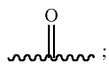

and B is:

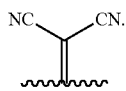

In a ninth embodiment of the first aspect, provided herein is the compound of the eighth embodiment of the first aspect, wherein each of $D^1$, $D^2$, and $D^3$ is —S—.

In a tenth embodiment of the first aspect, provided herein is the compound of the ninth embodiment of the first aspect, wherein J is hydrogen or an alkyl group; G is hydrogen, F, Cl, or an alkyl group; and each of $R^1$, $R^2$, $R^3$, and $R^4$ is an alkyl group selected from the from the group consisting of $C_2$-$C_{40}$ straight-chain alkyl, $C_3$-$C_{40}$ branched alkyl, $C_3$-$C_{40}$ cyclic alkyl, $C_2$-$C_{40}$ alkyl aryl, and $C_2$-$C_{40}$ alkyl heteroaryl.

In an eleventh embodiment of the first aspect, provided herein is the compound of the ninth embodiment of the first aspect, wherein $Ar^1$ is selected from the group consisting of:

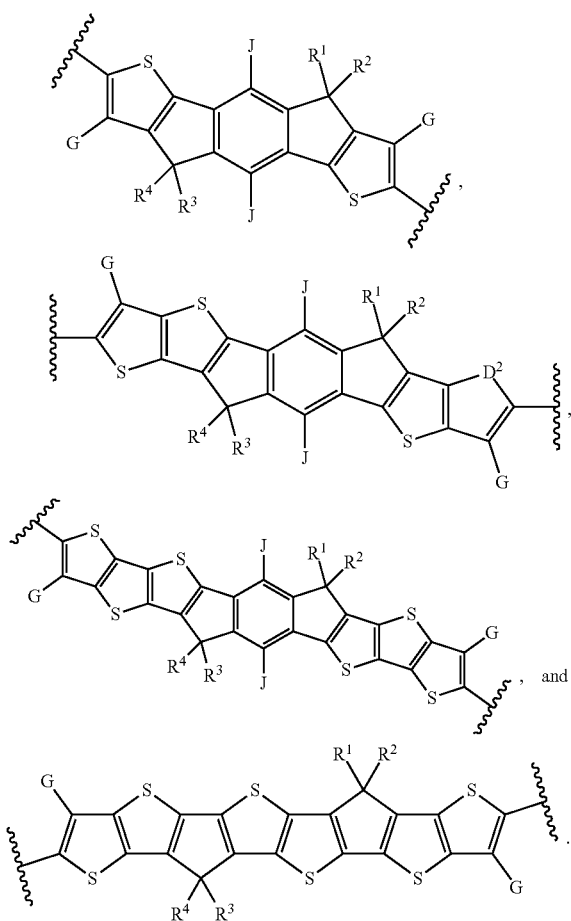

In a twelfth embodiment of the first aspect, provided herein is the compound of the eleventh embodiment of the first aspect, wherein J is hydrogen or an alkyl group; and each of $R^1$, $R^2$, $R^3$, and $R^4$ is an alkyl group selected from the group consisting of $C_2$-$C_{40}$ straight-chain alkyl, $C_3$-$C_{40}$ branched alkyl, $C_3$-$C_{40}$ cyclic alkyl, $C_2$-$C_{40}$ alkyl aryl, and $C_2$-$C_{40}$ alkyl heteroaryl.

In a thirteenth embodiment of the first aspect, provided herein is the compound of the first aspect, wherein $Ar^2$ is selected from the group consisting of:

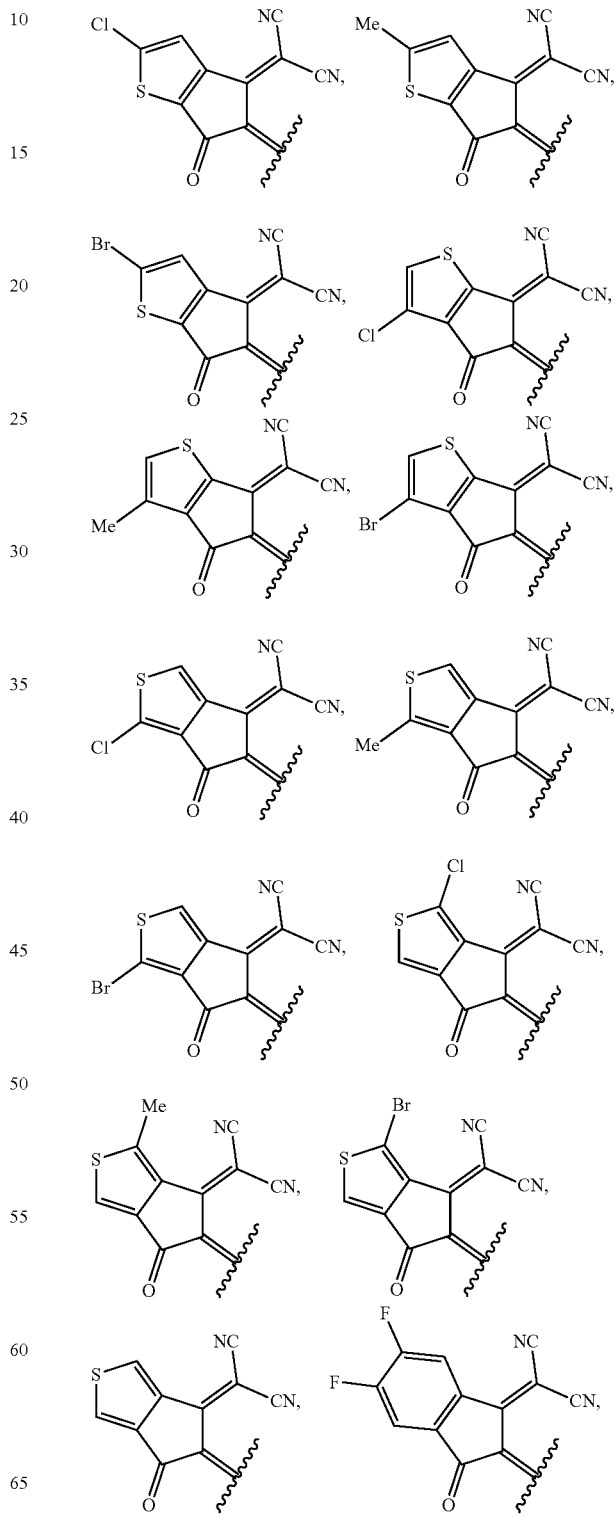

-continued

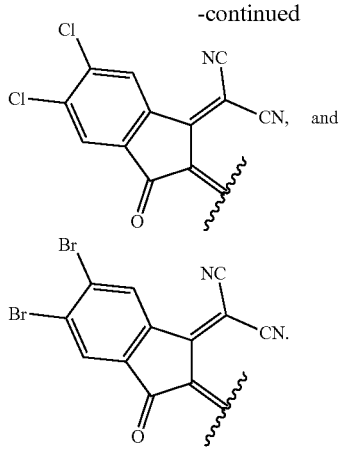

and

In a fourteenth embodiment of the first aspect, provided herein is the compound of the twelfth embodiment of the first aspect, wherein $Ar^1$ is selected from the group consisting of:

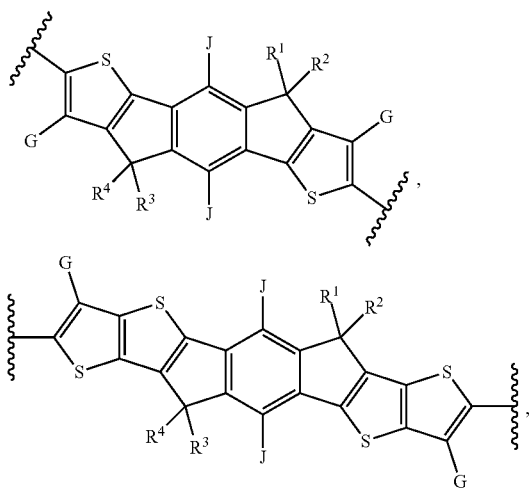

-continued

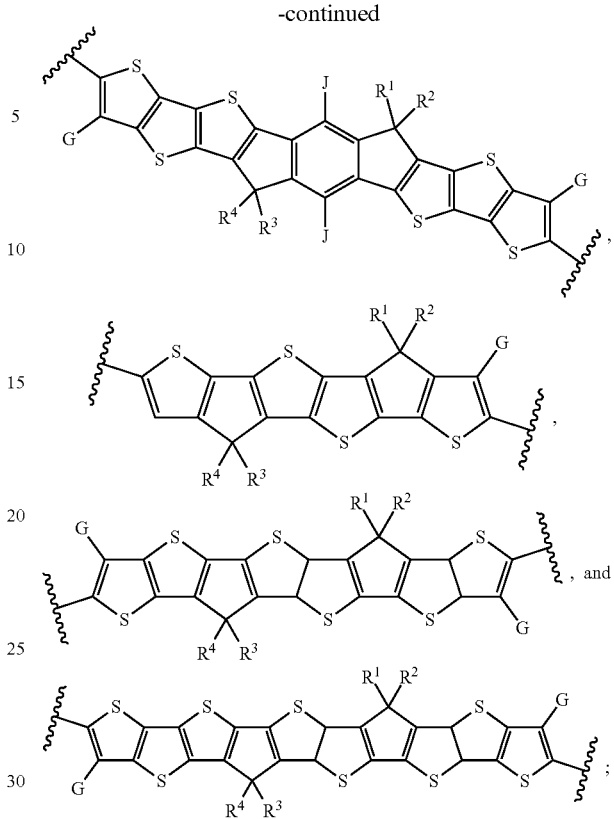

G is hydrogen F, Cl, $C_2$-$C_{40}$ straight-chain alkyl, $C_3$-$C_{40}$ branched alkyl, or $C_3$-$C_{40}$ cyclic alkyl; each of $R^1$, $R^2$, $R^3$, and $R^4$ is an alkyl group selected from the group consisting of $C_2$-$C_{40}$ straight-chain alkyl, $C_3$-$C_{40}$ branched alkyl, $C_3$-$C_{40}$ cyclic alkyl, $C_2$-$C_{40}$ alkyl aryl, and $C_2$-$C_{40}$ alkyl heteroaryl; and J is hydrogen or an alkyl group.

In a fifteenth embodiment of the first aspect, provided herein is the compound of the twelfth embodiment of the fourteenth aspect, wherein G is hydrogen and J is hydrogen.

In a sixteenth embodiment of the first aspect, provided herein is the compound of the first aspect, wherein the compound is selected from the group consisting of:

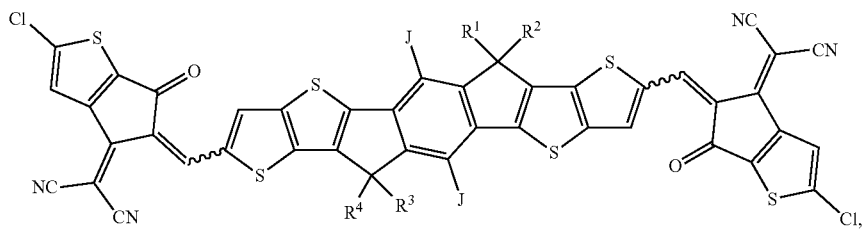

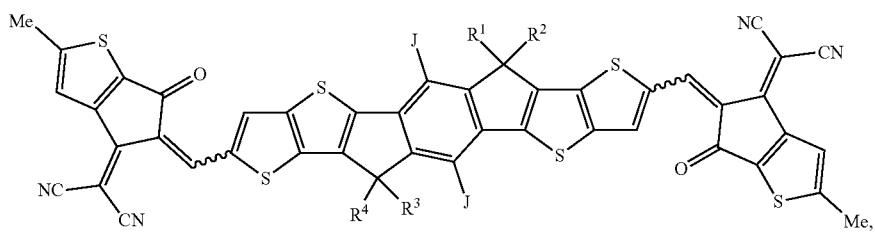

-continued
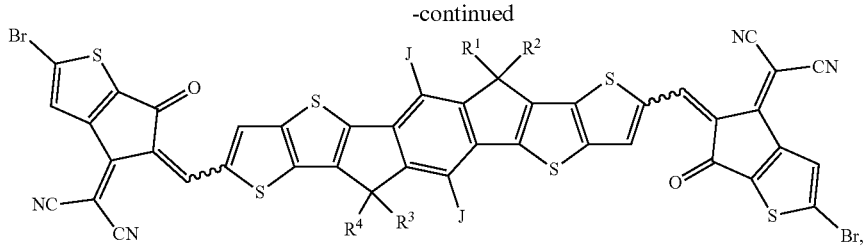
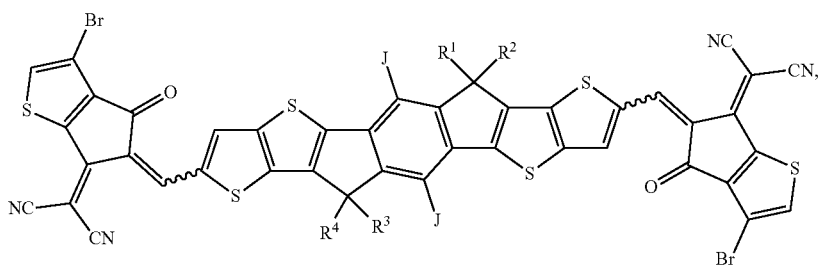
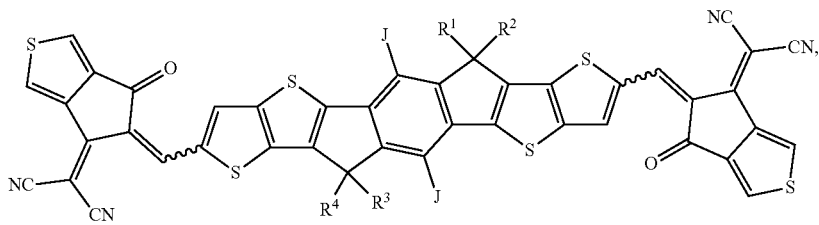
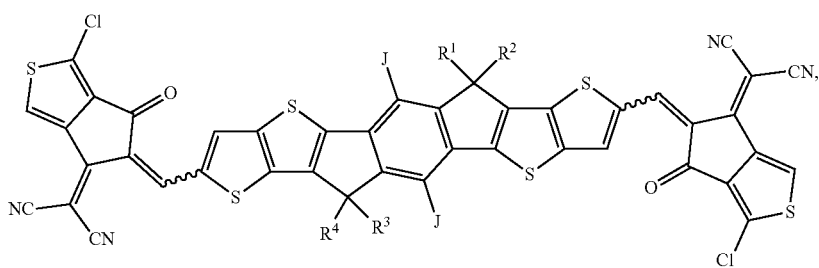
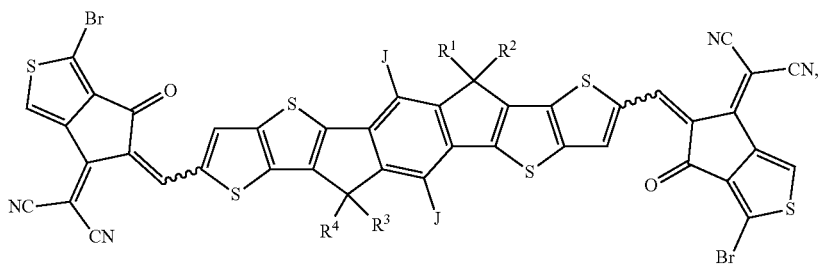
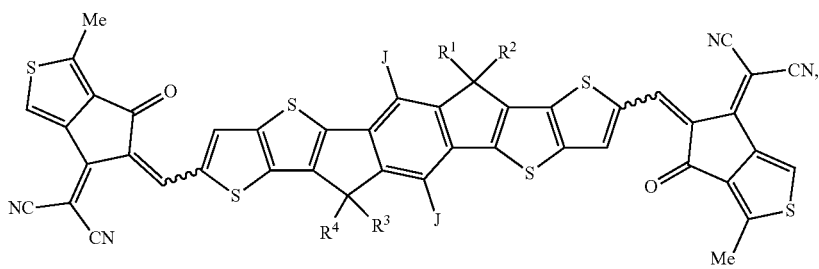

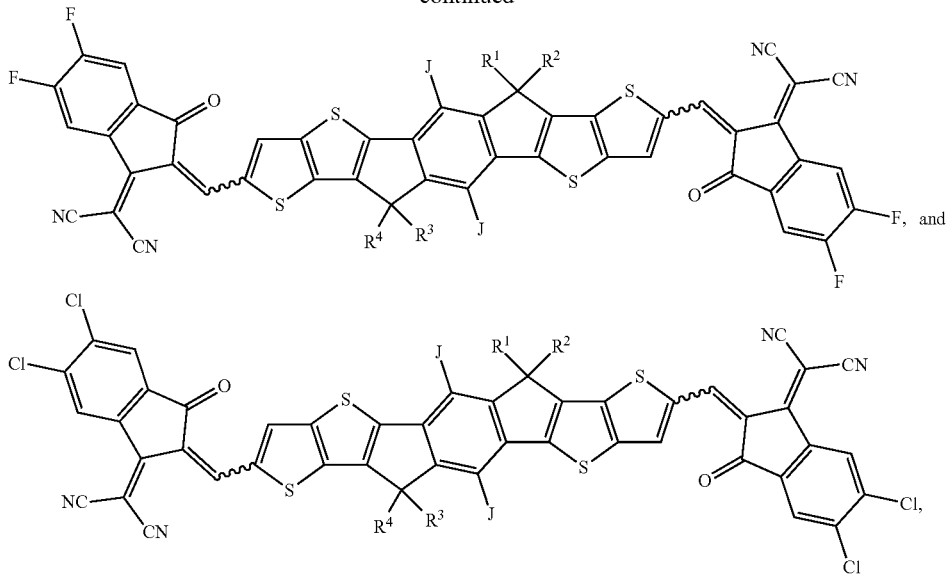

wherein each of $R^1$, $R^2$, $R^3$, and $R^4$ is an alkyl group selected from the group consisting of $C_2$-$C_{40}$ straight-chain alkyl, $C_3$-$C_{40}$ branched alkyl, $C_3$-$C_{40}$ cyclic alkyl, $C_2$-$C_{40}$ alkyl aryl, and $C_2$-$C_{40}$ alkyl heteroaryl; and J is hydrogen or an alkyl group.

In a seventeenth embodiment of the first aspect, provided herein is the compound of the sixteenth embodiment of the first aspect, wherein each of $R^1$, $R^2$, $R^3$, and $R^4$ is 4-(n-hexyl)phenyl or n-octyl; and J is hydrogen, with the proviso that if the compound is:

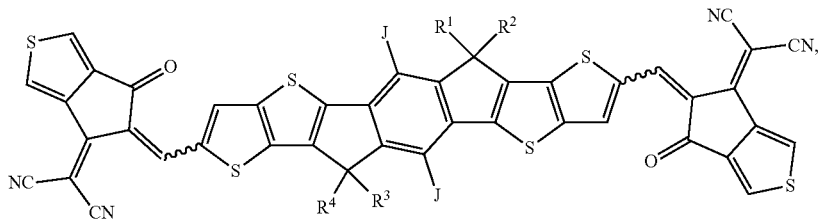

then each of $R^1$, $R^2$, $R^3$, and $R^4$ is n-hexyl; and J is hydrogen.

In a second aspect, provided herein is a photovoltaic device comprising the compound of the first aspect.

In a third aspect, provided herein is a photovoltaic device comprising the compound of the seventeenth embodiment of the first aspect.

In the present disclosure, it was surprisingly found that an A-D-A acceptor comprising one or more of the following formula can achieve red-shifted absorption and stronger molecular packing compared with the unsubstituted thiophene end groups.

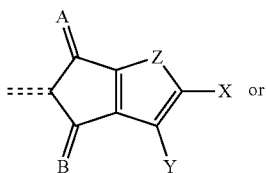

Formula I

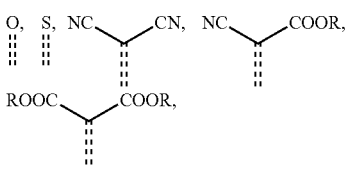

wherein, X and Y are independently selected from the group consisting of H, F, Cl, Br, I, CN, and SCN, wherein the total number of H is 0 or 1;

Z is selected from O, S, Se, Te, N—$R^1$, wherein $R^1$ are independently a straight-chain, branched, or cyclic alkyl group; and A and B are independently selected from:

O, S, NC CN, NC COOR,

ROOC COOR, wherein R are independently a straight-chain, branched, or cyclic alkyl group.

In some embodiments of the present disclosure, by halogenation of the unsubstituted thiophene end groups, the resulting C8-ITCC-Cl exhibits lowered energy levels and red-shifted absorption with an onset of ~800 nm relative to C8-ITCC. Moreover, stronger lamellar and π-π stacking, together with suitable domain sizes and a higher domain purity were observed for C8-ITCC-Cl when blended with a medium bandgap polymer PBDB-TF. Consequently, a higher PCE of 12.7% with a VOC of 0.95 V, a JSC of 18.5 mA cm$^{-2}$ and an FF of 73% is achieved by the C8-ITCC-Cl-based device, which outperforms that of the C8-ITCC-based one and is among the highest efficiencies for the TIC-containing SMAs.

In further embodiments, SMAs comprising Formula I were demonstrated to exhibit high crystallinity suitable for organic solar cell applications.

The present subject matter further relates to the use of a formulation as described herein as a coating or printing interlayer, especially for the preparation of OE devices and rigid or flexible organic photovoltaic (OPV) cells and devices.

The above description is only an outline of the technical schemes of the present invention. Preferred embodiments of the present disclosure are provided below in conjunction with the attached drawings to enable one with ordinary skill in the art to better understand said and other objectives, features and advantages of the present invention and to make the present invention accordingly. The formulations, methods and devices of the present subject matter provide surprising improvements in the efficiency of the OE devices and the production thereof. Unexpectedly, the performance, the lifetime and the efficiency of the OE devices can be improved, if these devices are achieved by using a formulation of the present subject matter. Furthermore, the formulation of the present subject matter provides an astonishingly high level of film forming. Especially, the homogeneity and the quality of the films can be improved. In addition thereto, the present subject matter enables better solution printing of OE devices, especially OPV devices.

BRIEF DESCRIPTION OF THE DRAWINGS

It should be understood that the drawings described above or below are for illustration purposes only. The drawings are

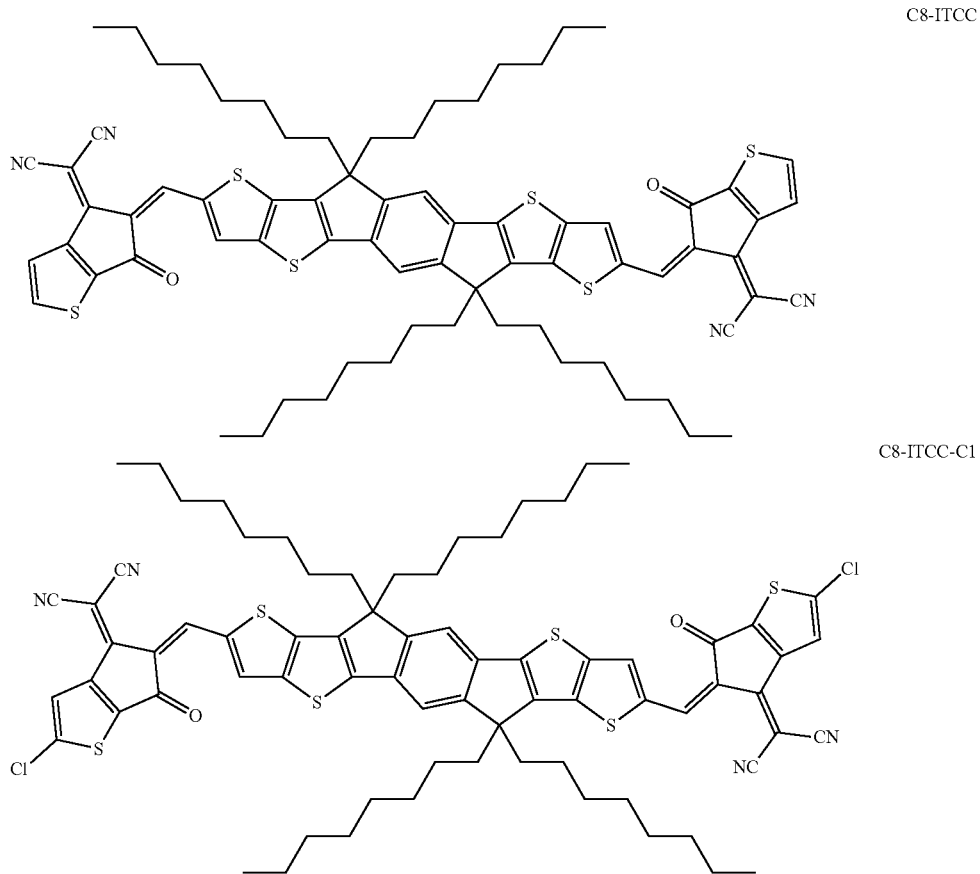

C8-ITCC

C8-ITCC-Cl not necessarily to scale, with emphasis generally being placed upon illustrating the principles of the present teachings. The drawings are not intended to limit the scope of the present teachings in any way.

Figure 1:
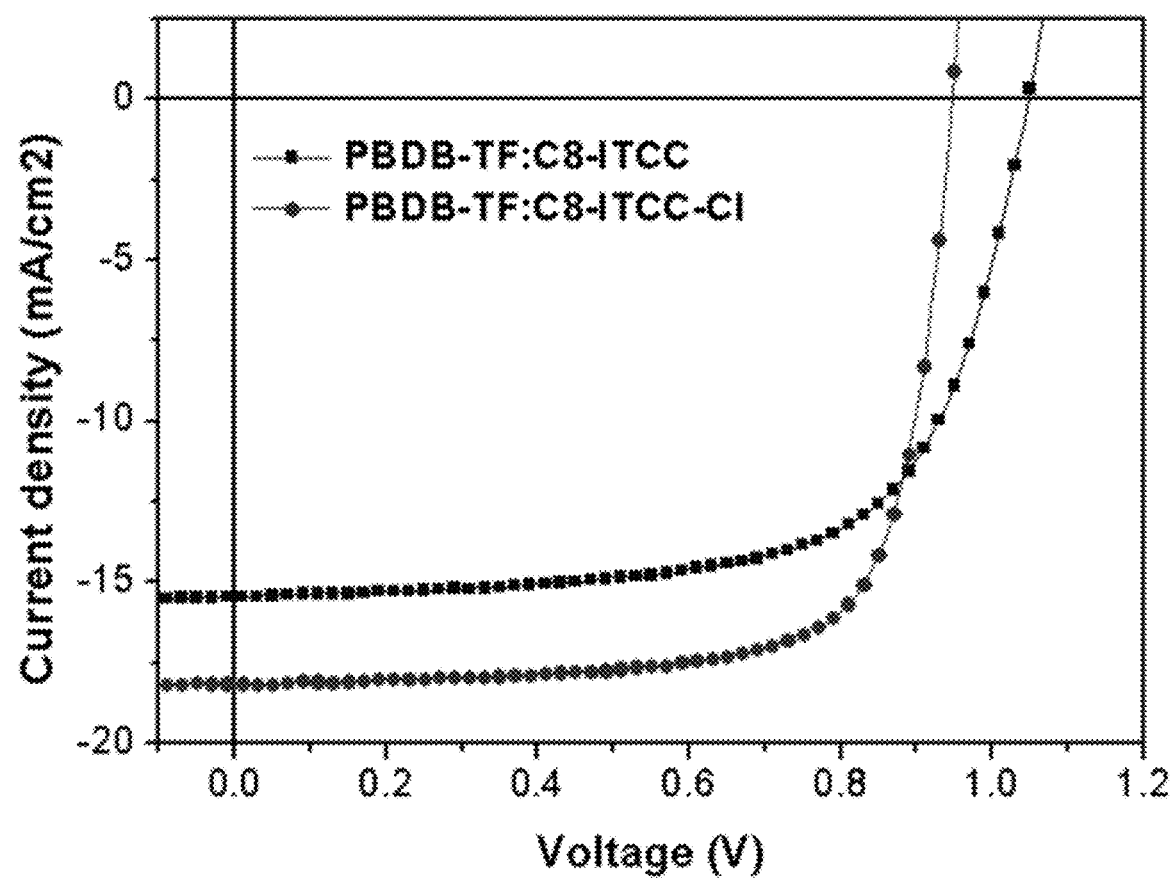

FIG. 1 shows J-V curves of the PBDB-TF:C8-ITCC and PBDB-TF:C8-ITCC-Cl devices in accordance with certain embodiments described herein.

Figure 2:
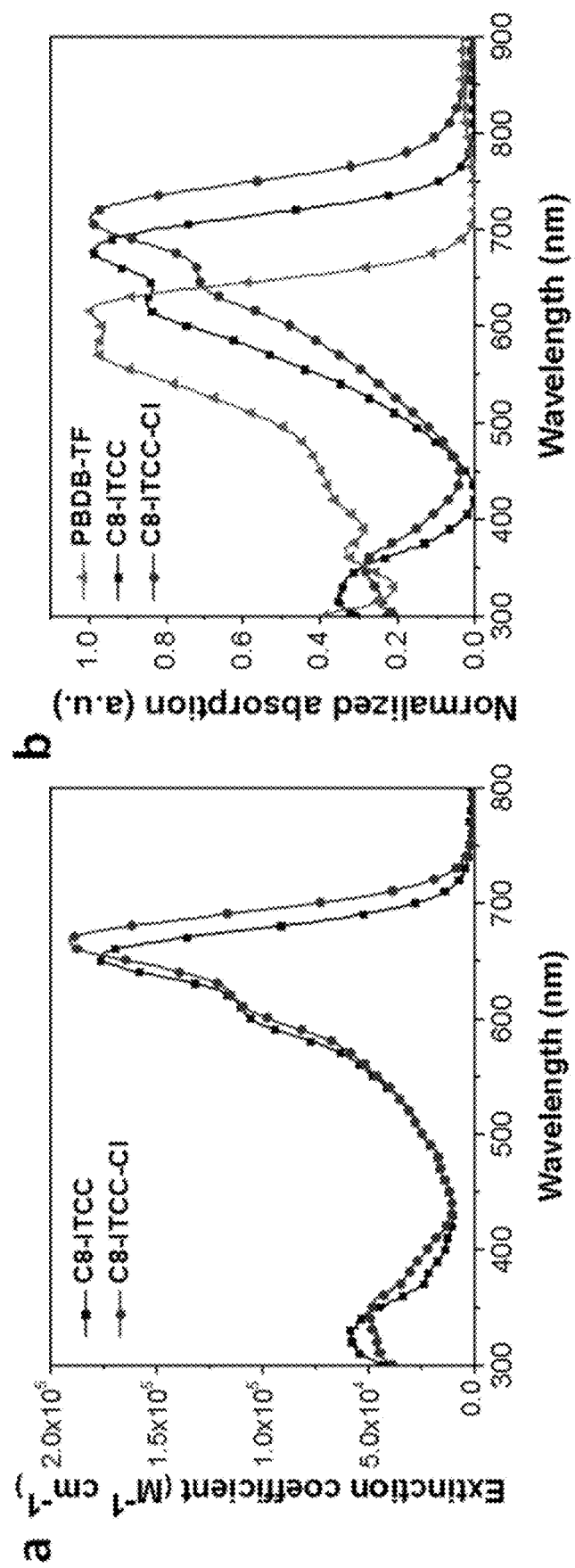

FIG. 2 shows (a) UV-Vis absorption spectra of C8-ITCC and C8-ITCC-Cl in diluted chloroform solutions with a concentration of $10^{-6}$ M. (b) Normalized UV-Vis absorption spectra of C8-ITCC and C8-ITCC-Cl in the thin-film state.

Figure 3:
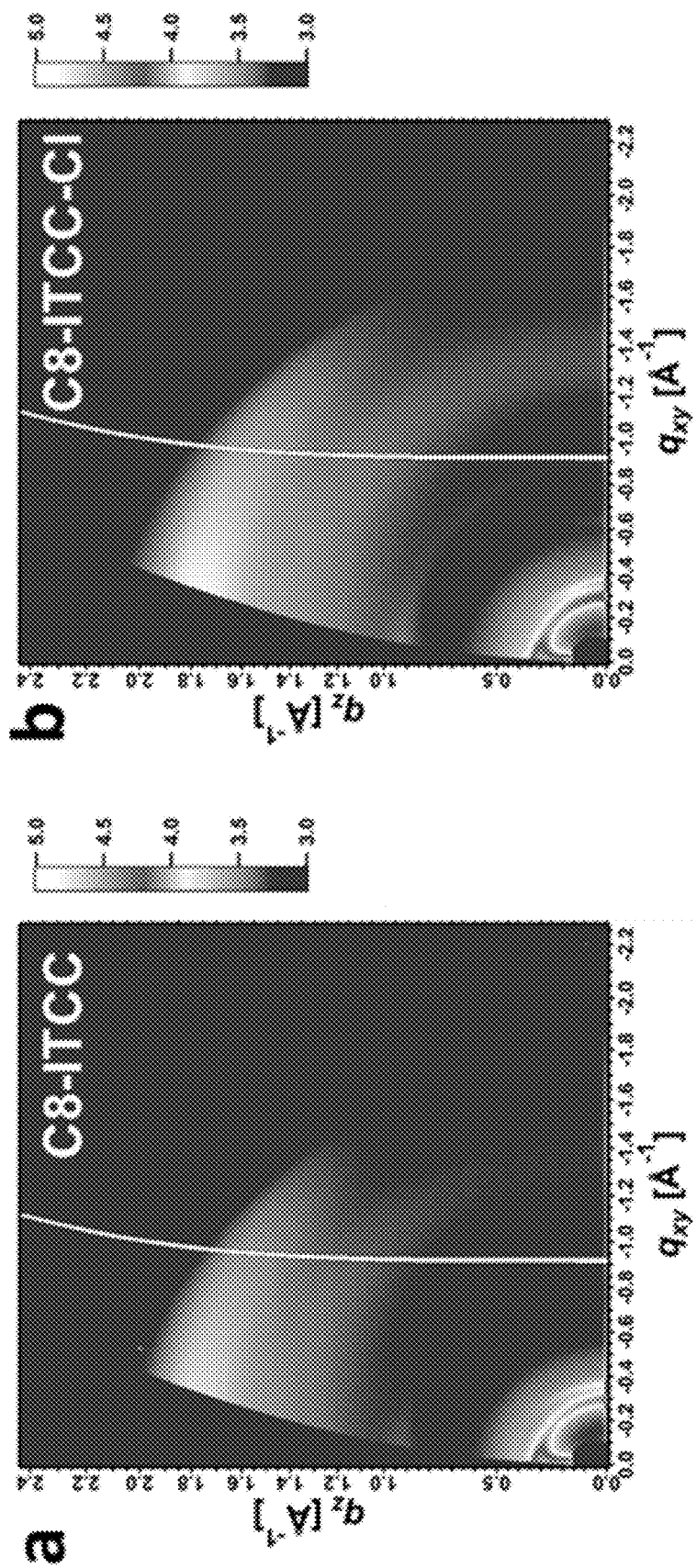
Figure 3:
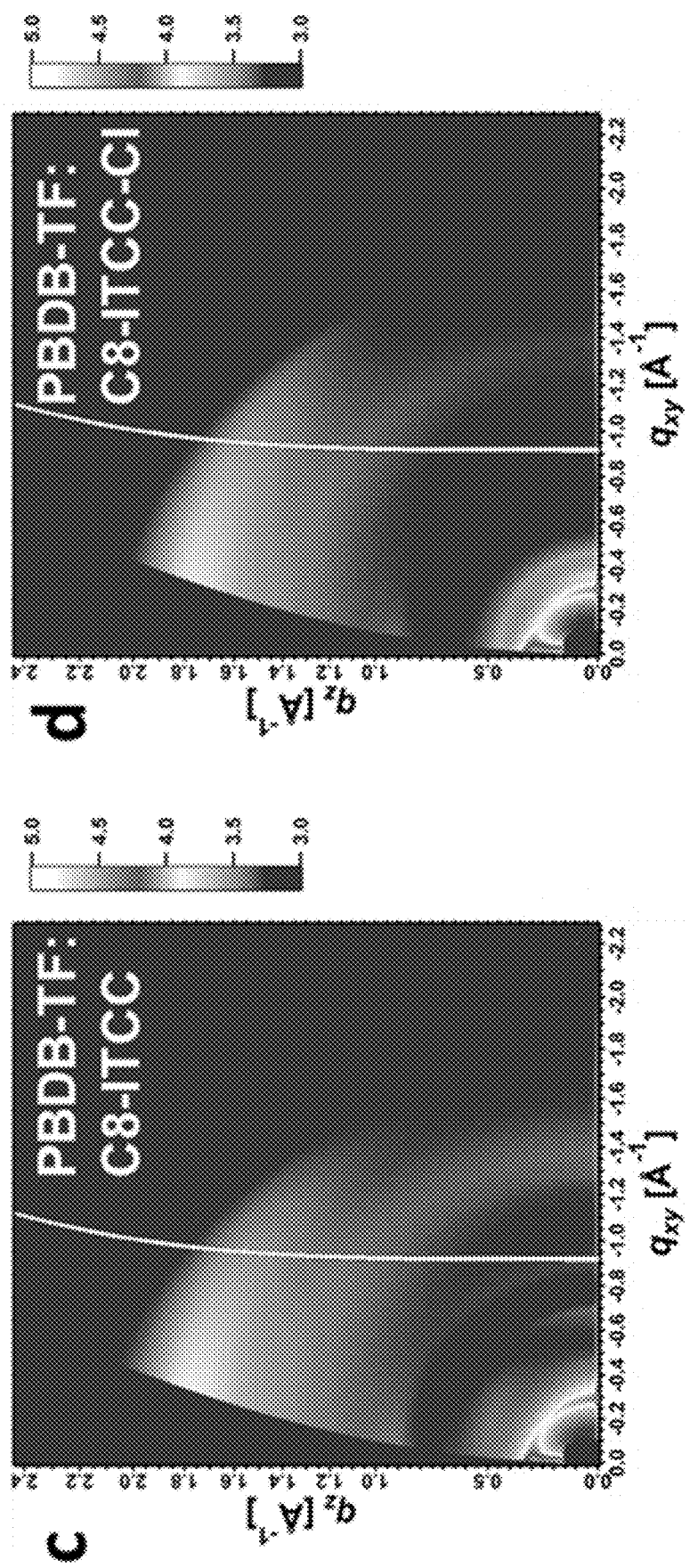

FIG. 3 shows 2D GIWAXS patterns of (a) the pristine C8-ITCC film, (b) pristine C8-ITCC-Cl film, (c) the PBDB-TF:C8-ITCC blend film and (d) the PBDB-TF:C8-ITCC-Cl blend film.

Figure 4:
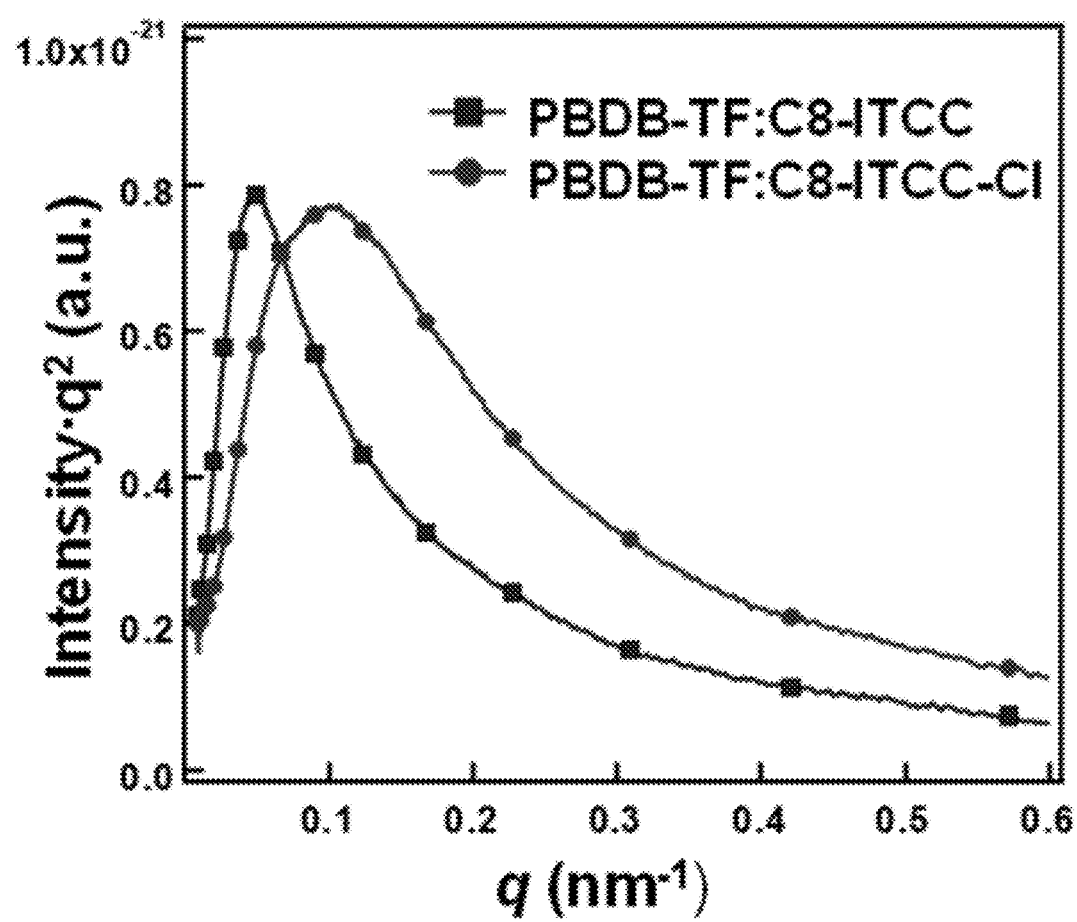

FIG. 4 shows RSoXS profiles of the PBDB-TF:C8-ITCC and PBDB-TF:C8-ITCC-Cl blend films.

Figure 5:
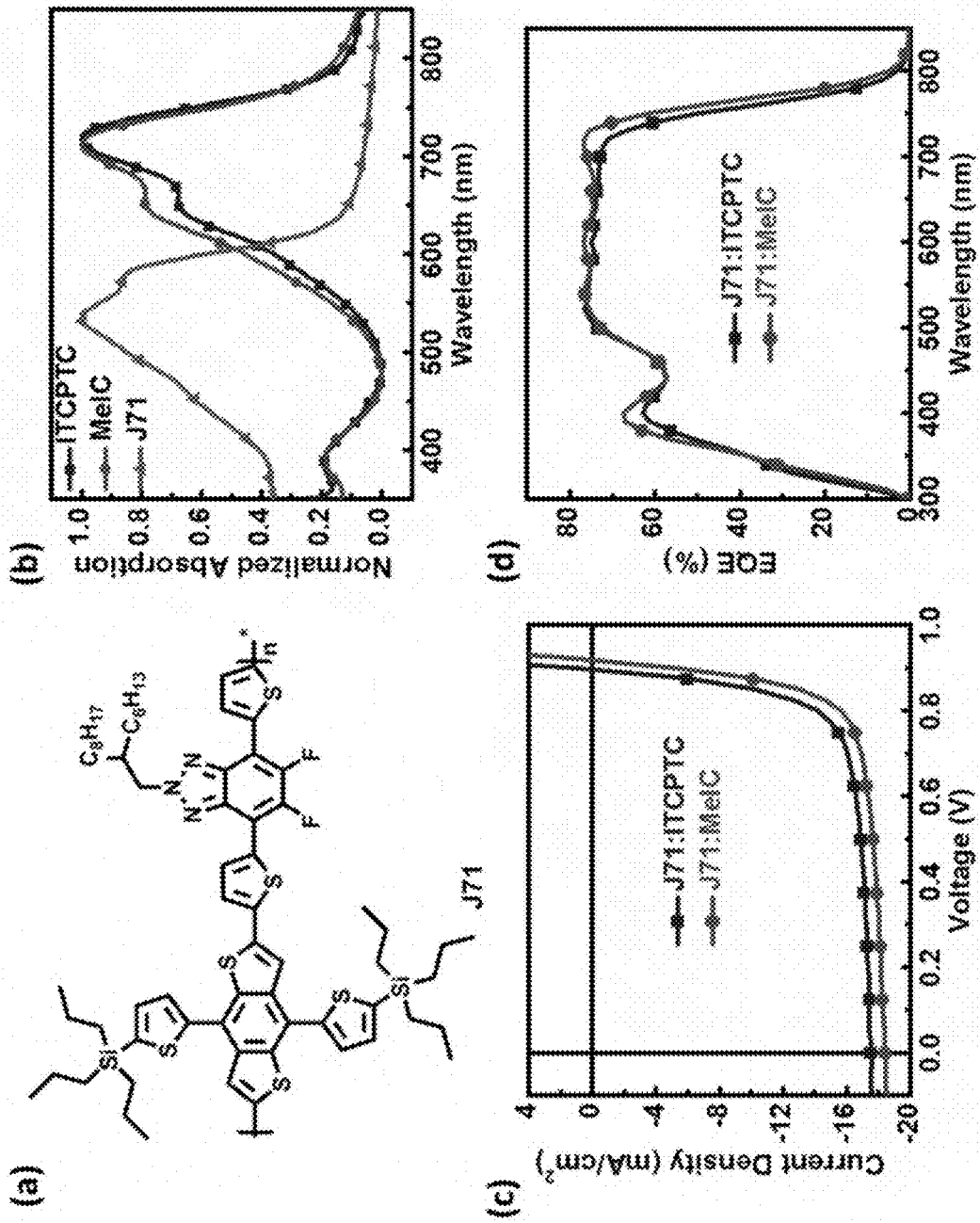

FIG. 5 shows (a) The chemical structures of J71; (b) the normalized UV-vis absorption spectra of J71, ITCPTC and MeIC in the film state; (c) J-V characteristics of the best PSCs with thermal annealing at 150° C. for 2 min under the AM 1.5 G illumination, 100 mW cm$^{-2}$; (d) EQE spectra of the corresponding devices based on J71: ITCPTC and J71: MeIC in accordance with certain embodiments described herein.

Figure 6:
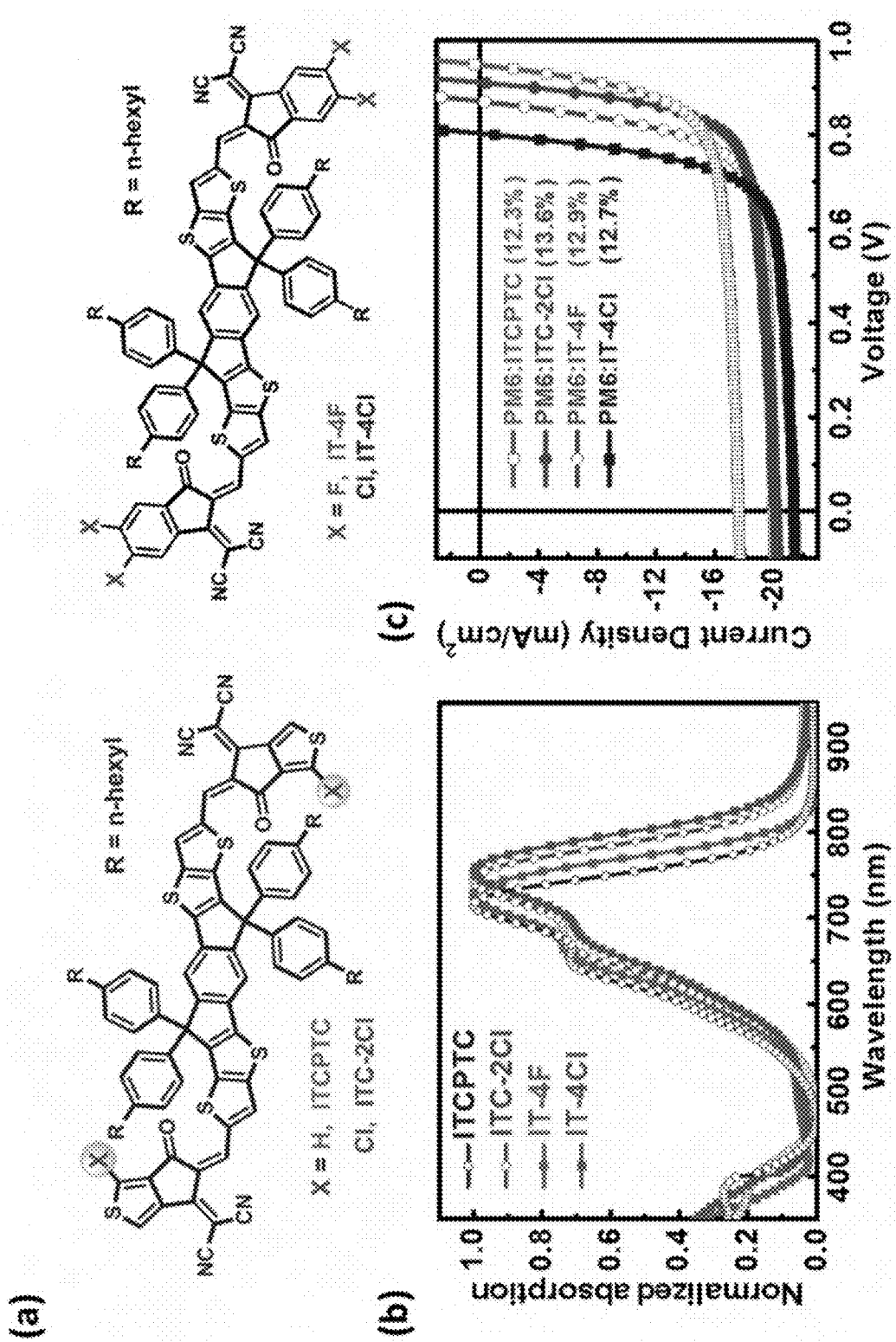

FIG. 6 shows (a) The chemical structures of ITCPTC, ITC-2Cl, IT-4F and IT-4Cl in accordance with certain embodiments described herein; (b) the normalized UV-vis absorption spectra of ITCPTC, ITC-2Cl, IT-4F and IT-4Cl in the film state; (c) J-V characteristics of the best PSCs in accordance with certain embodiments described herein.

Figure 7:
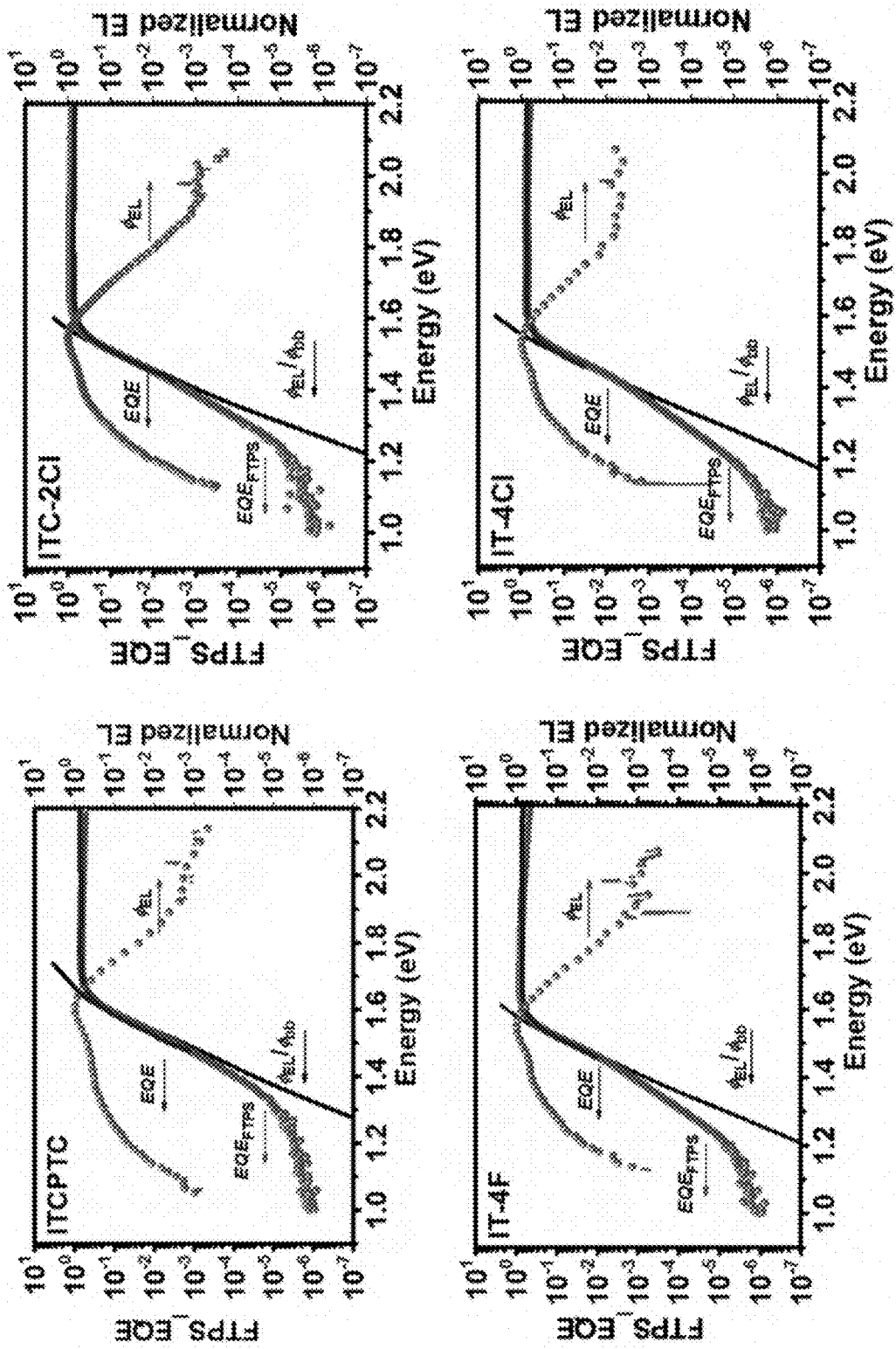

FIG. 7 shows normalized FTPS-EQE, EQE and EL of the ITCPTC-, ITC-2Cl, IT-4F and IT-4Cl-based devices.

Figure 8:
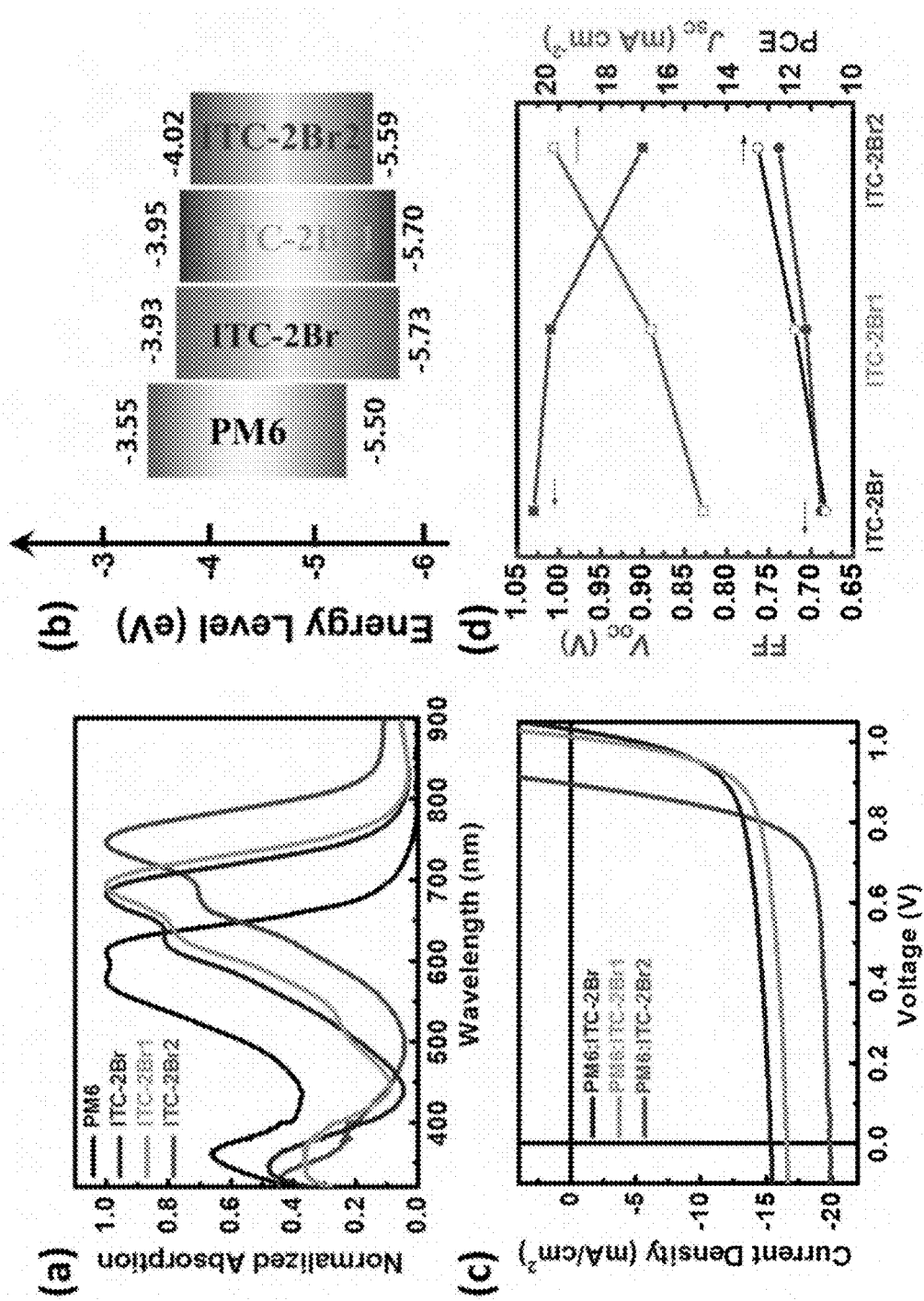

FIG. 8 shows normalized FTPS-EQE, EQE and EL of the ITCPTC-, ITC-2Cl, IT-4F and IT-4Cl-based devices in accordance with certain embodiments described herein.

Figure 9:
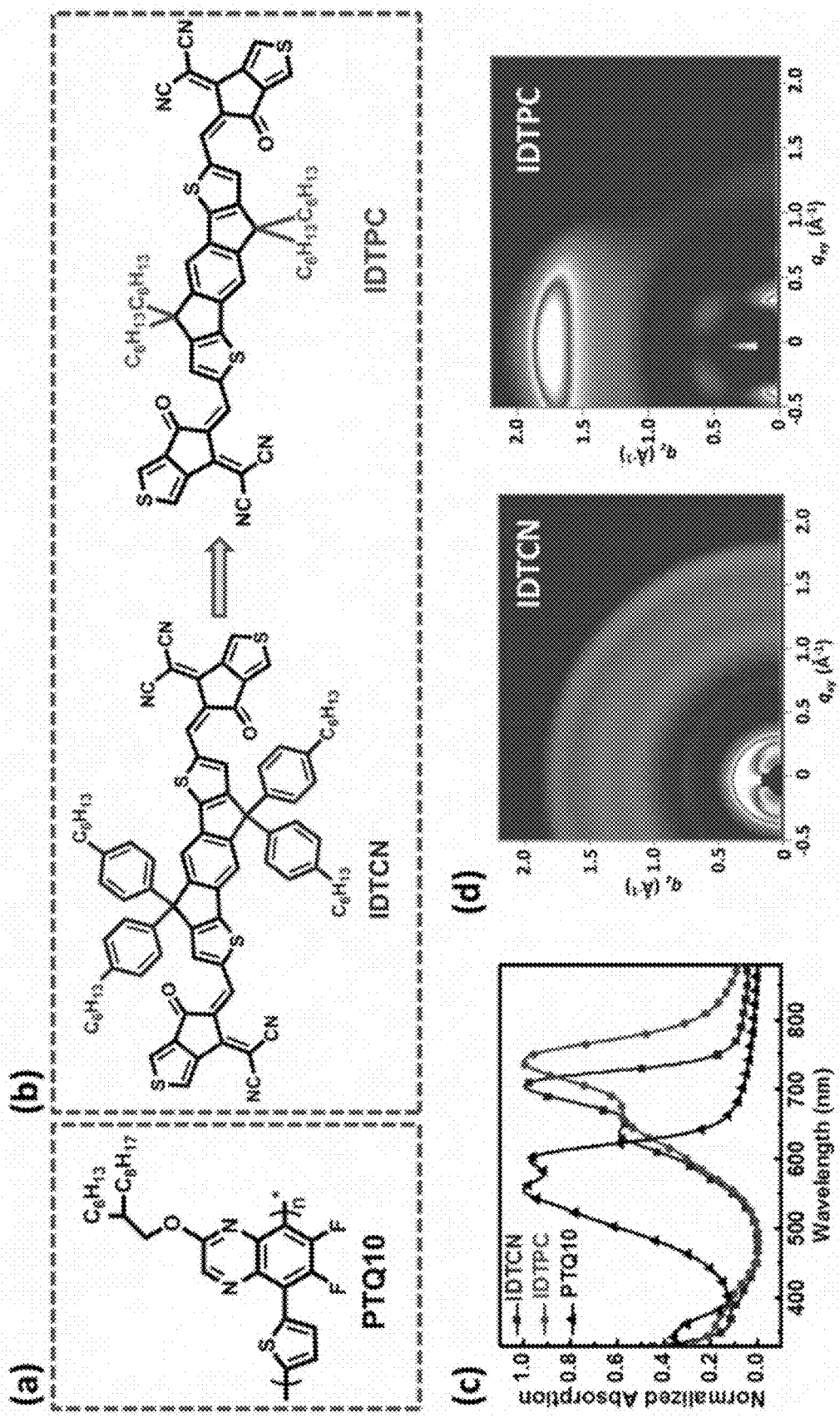

FIG. 9 shows (a) chemical structures of the polymer donor PTQ10; (b) Chemical structures of the acceptors of IDTCN and IDTPC; (c) Normalized UV-vis absorption spectra of PTQ10, IDTCN and IDTPC in neat film; (d) 2D GIXD patterns of IDTPC and IDTCN films.

Figure 10:
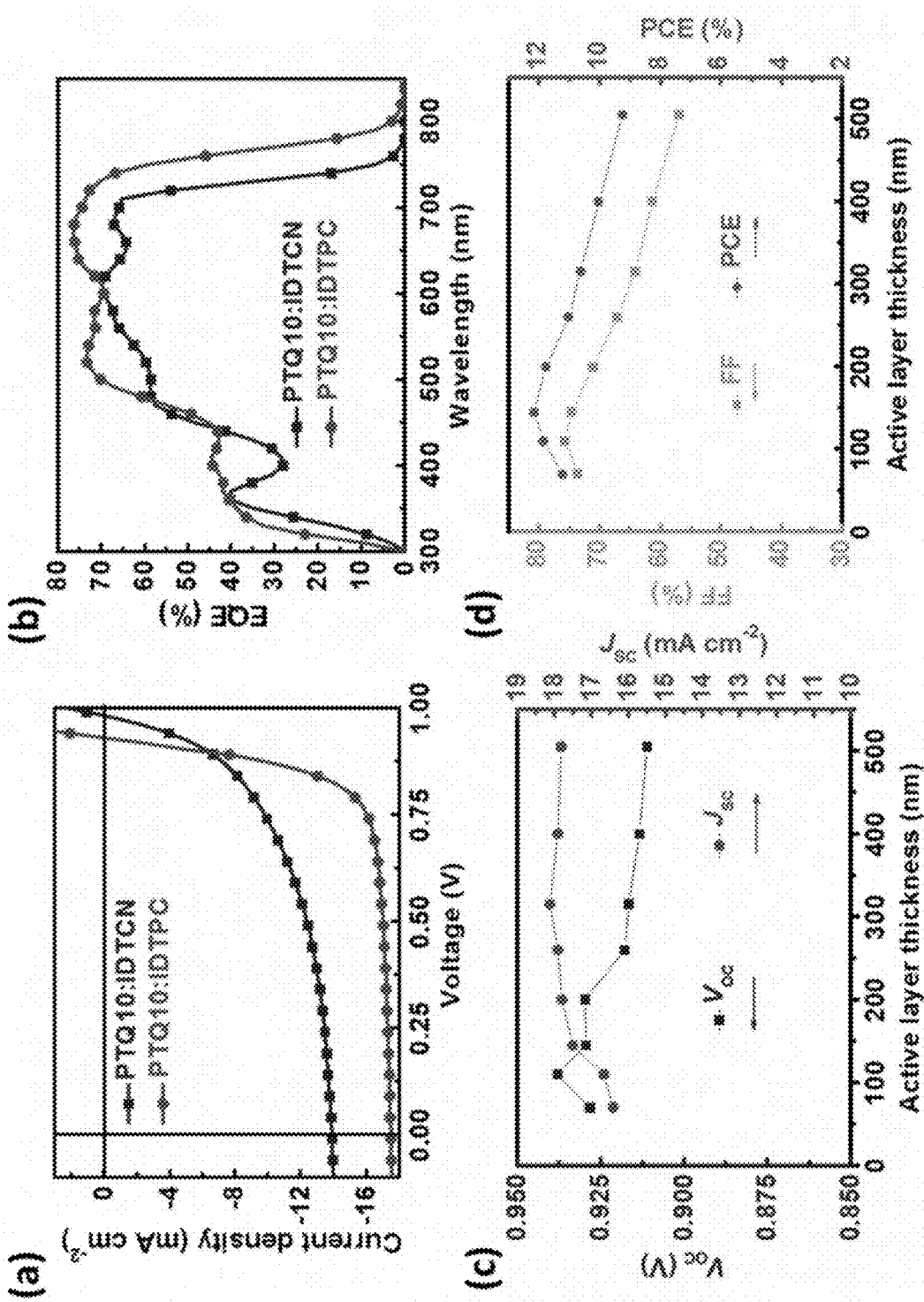

FIG. 10 shows (a) J-V characteristics of the PSCs under the illumination of AM 1.5G, 100 mW cm$^{-2}$; (b) EQE spectra of the best devices based on PTQ10:IDTCN and PTQ10:IDTPC; Thickness dependence of photovoltaic performance of the PTQ10:IDTPC-based PSCs. Plots of VOC or JSC (c) and FF or PCE (d) vs. the active layer thickness ranging from 70 to 505 nm for the PSCs based on PTQ10: IDTPC.

DETAILED DESCRIPTION

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein A small molecular organic compound is defined as an organic molecule with molecular weight lower than 3,000 g/mol.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, a "P-type semiconductor material" or a "donor" material refers to a semiconductor material, for example, an organic semiconductor material, having holes as the majority current or charge carriers. In some embodiments, when a p-type semiconductor material is deposited on a substrate, it can provide a hole mobility in excess of about 10$^{-5}$ cm$^2$/Vs. In the case of field-effect devices, a p-type semiconductor also can exhibit a current on/off ratio of greater than about 10.

As used herein, an "N-type semiconductor material" or an "acceptor" material refers to a semiconductor material, for example, an organic semiconductor material, having electrons as the majority current or charge carriers. In some embodiments, when an n-type semiconductor material is deposited on a substrate, it can provide an electron mobility in excess of about 10$^{-5}$ cm$^2$/Vs. In the case of field-effect devices, an n-type semiconductor also can exhibit a current on/off ratio of greater than about 10.

As used herein, "mobility" refers to a measure of the velocity with which charge carriers, for example, holes (or units of positive charge) in the case of a p-type semiconductor material and electrons (or units of negative charge) in the case of an n-type semiconductor material, move through the material under the influence of an electric field. This parameter, which depends on the device architecture, can be measured using a field-effect device or space-charge limited current measurements.

As used herein, "homo-tandem" refers to the tandem solar cells constructed from the photoactive layers with identical optical absorptions.

As used herein, "hybrid tandem" refers to the tandem solar cells constructed from the photoactive layers with optical absorptions.

As used herein, "sub-cell" refers to the photoactive layers that can convert light into electricity in tandem solar cells.

As used herein, a compound can be considered "ambient stable" or "stable at ambient conditions" when a transistor incorporating the compound as its semiconducting material exhibits a carrier mobility that is maintained at about its initial measurement when the compound is exposed to ambient conditions, for example, air, ambient temperature, and humidity, over a period of time. For example, a compound can be described as ambient stable if a transistor incorporating the compound shows a carrier mobility that does not vary more than 20% or more than 10% from its initial value after exposure to ambient conditions, including, air, humidity and temperature, over a 3 day, 5 day, or 10 day period.

As used herein, fill factor (FF) is the ratio (given as a percentage) of the actual maximum obtainable power, (Pm or Vmp*Jmp), to the theoretical (not actually obtainable) power, (Jsc*Voc). Accordingly, FF can be determined using the equation:

$$FF=(Vmp*Jmp)/(Jsc*Voc)$$

where Jmp and Vmp represent the current density and voltage at the maximum power point (Pm), respectively, this point being obtained by varying the resistance in the circuit until J*V is at its greatest value; and Jsc and Voc represent the short circuit current and the open circuit voltage, respectively. Fill factor is a key parameter in evaluating the performance of solar cells. Commercial solar cells typically have a fill factor of about 0.60% or greater.

As used herein, the open-circuit voltage (Voc) is the difference in the electrical potentials between the anode and the cathode of a device when there is no external load connected.

As used herein, the power conversion efficiency (PCE) of a solar cell is the percentage of power converted from absorbed light to electrical energy. The PCE of a solar cell can be calculated by dividing the maximum power point (Pm) by the input light irradiance (E, in W/m$^2$) under standard test conditions (STC) and the surface area of the solar cell (Ac in m$^2$). STC typically refers to a temperature of 25° C. and an irradiance of 1000 W/m$^2$ with an air mass 1.5 (AM 1.5) spectrum.

As used herein, a component (such as a thin film layer) can be considered "photoactive" if it contains one or more compounds that can absorb photons to produce excitons for the generation of a photocurrent.

As used herein, "solution-processable" refers to compounds (e.g., polymers), materials, or compositions that can be used in various solution-phase processes including spin-coating, printing (e.g., inkjet printing, gravure printing, offset printing and the like), spray coating, electrospray coating, drop casting, dip coating, blade coating, and the like.

As used herein, a "semicrystalline polymer" refers to a polymer that has an inherent tendency to crystallize at least partially either when cooled from a melted state or deposited from solution, when subjected to kinetically favorable conditions such as slow cooling, or low solvent evaporation rate and so forth. The crystallization or lack thereof can be readily identified by using several analytical methods, for example, differential scanning calorimetry (DSC) and/or X-ray diffraction (XRD).

As used herein, "annealing" refers to a post-deposition heat treatment to the semicrystalline polymer film in ambient or under reduced/increased pressure for a time duration of more than 100 seconds, and "annealing temperature" refers to the maximum temperature that the polymer film is exposed to for at least 60 seconds during this process of annealing. Without wishing to be bound by any particular theory, it is believed that annealing can result in an increase of crystallinity in the polymer film, where possible, thereby increasing field effect mobility. The increase in crystallinity can be monitored by several methods, for example, by comparing the differential scanning calorimetry (DSC) or X-ray diffraction (XRD) measurements of the as-deposited and the annealed films.

As used herein, a "polymeric compound" (or "polymer") refers to a molecule including a plurality of one or more repeating units connected by covalent chemical bonds. A polymeric compound can be represented by General Formula I:

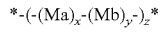

*-(-(Ma)$_x$-(Mb)$_y$-)$_z$*  General Formula I wherein each Ma and Mb is a repeating unit or monomer. The polymeric compound can have only one type of repeating unit as well as two or more types of different repeating units. When a polymeric compound has only one type of repeating unit, it can be referred to as a homopolymer. When a polymeric compound has two or more types of different repeating units, the term "copolymer" or "copolymeric compound" can be used instead. For example, a copolymeric compound can include repeating units where Ma and Mb represent two different repeating units. Unless specified otherwise, the assembly of the repeating units in the copolymer can be head-to-tail, head-to-head, or tail-to-tail. In addition, unless specified otherwise, the copolymer can be a random copolymer, an alternating copolymer, or a block copolymer. For example, General Formula I can be used to represent a copolymer of Ma and Mb having x mole fraction of Ma and y mole fraction of Mb in the copolymer, where the manner in which comonomers Ma and Mb is repeated can be alternating, random, regiorandom, regioregular, or in blocks, with up to z comonomers present. In addition to its composition, a polymeric compound can be further characterized by its degree of polymerization (n) and molar mass (e.g., number average molecular weight (M) and/or weight average molecular weight (Mw) depending on the measuring technique(s)).

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and isopropyl), butyl (e.g., n-butyl, iso-butyl, sec-butyl, tert-butyl), pentyl groups (e.g., n-pentyl, 1-methylbutyl, 2-methylbutyl, iso-pentyl, tert-pentyl, 1,2-dimethylpropyl, neopentyl, and 1-ethylpropyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group). In some embodiments, alkenyl groups can be substituted as described herein. An alkenyl group is generally not substituted with another alkenyl group, an alkyl group, or an alkynyl group.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The representation "⌇" as used herein in connection to chemical a group or moiety is intended to represent the covalent bond that the aforementioned chemical group or moiety is covalently bonded to another chemical group or moiety.

In certain embodiments, the A-D-A SMAs described herein can generally be represented by a compound of Formula 1:

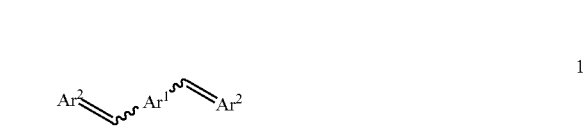

1 wherein $Ar^1$ is selected from the group consisting of:

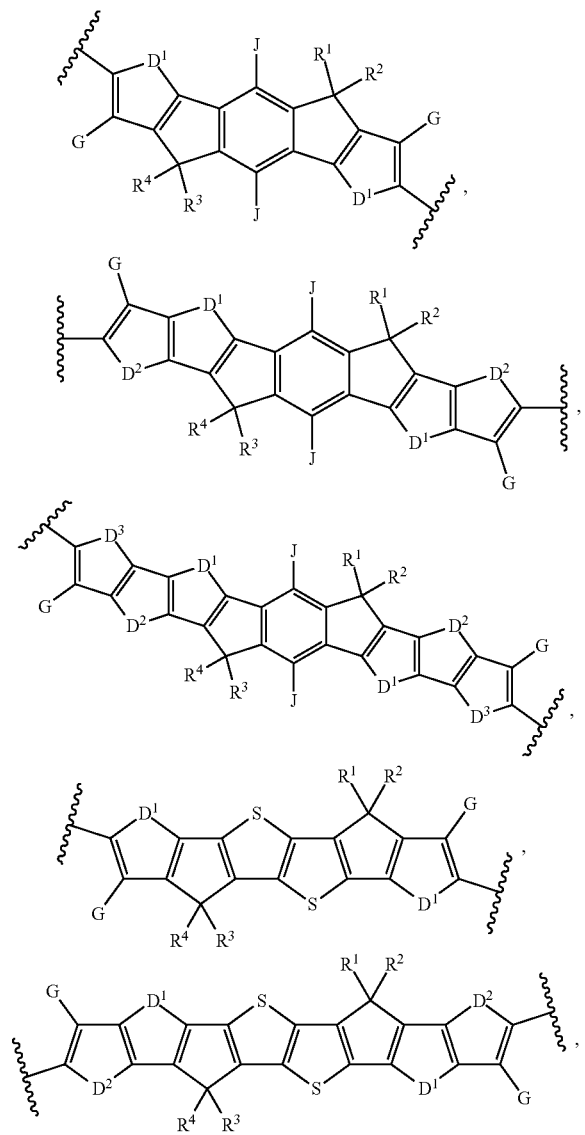

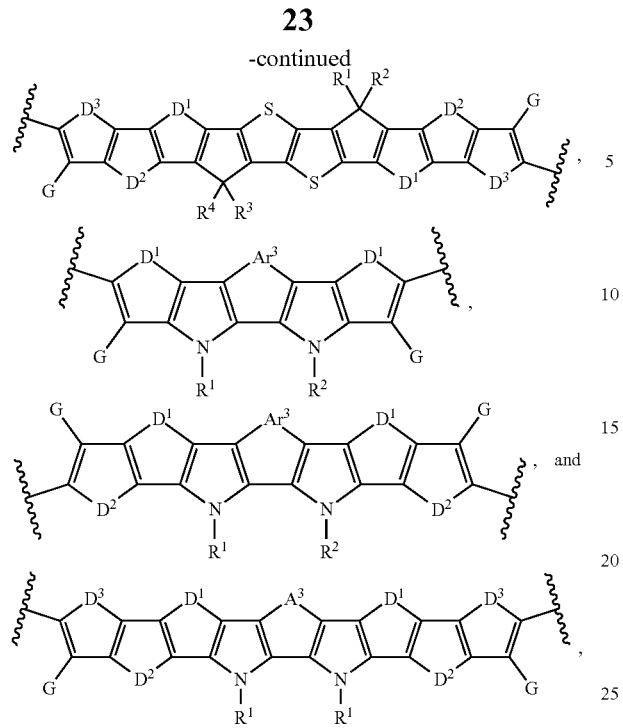

wherein each of $R^1$, $R^2$, $R^3$, and $R^4$ is independently an alkyl group selected from the group consisting of $C_2$-$C_{40}$ straight-chain alkyl, $C_3$-$C_{40}$ branched alkyl, $C_3$-$C_{40}$ cyclic alkyl, $C_2$-$C_{40}$ alkyl aryl, and $C_2$-$C_{40}$ alkyl heteroaryl, wherein one or more non-adjacent C atoms of the alkyl group are optionally replaced by —O—, —S—, —(C=O)—, —C(=O)O—, —OC(=O)—, —O(C=O)O—, —CR=CR—, or —C≡C—, and wherein one or more hydrogen atoms of the alkyl group are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups;

each of $D^1$, $D^2$, and $D^3$ is independently selected from the group consisting of —O—, —S—, —Se—, —Te—, —(NR)—, and —C(R)$_2$—;

each of J and G for each occurrence is independently selected from the group consisting of hydrogen, F, Cl, Br, CN, OR, NHR, N(R)$_2$, and an alkyl group selected from the group consisting of $C_2$-$C_{40}$ straight-chain alkyl, $C_3$-$C_4$ branched alkyl, $C_3$-$C_{40}$ cyclic alkyl, $C_2$-$C_{40}$ alkyl aryl, and $C_2$-$C_{40}$ alkyl heteroaryl, wherein one or more non-adjacent C atoms of the alkyl group are optionally replaced by —O—, —S—, —(C=O)—, —C(=O)O—, —OC(=O)—, —O(C=O)O—, —CR=CR—, or —C≡C—, and wherein one or more H atoms of the alkyl group are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups;

$Ar^3$ is selected from the group consisting of:

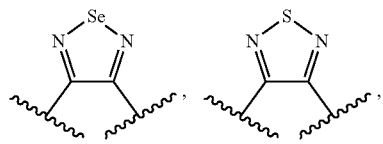

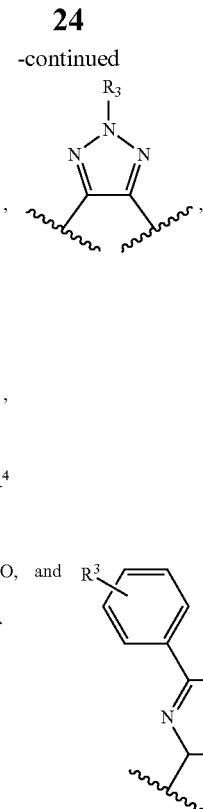

$Ar^2$ is selected from the group consisting of:

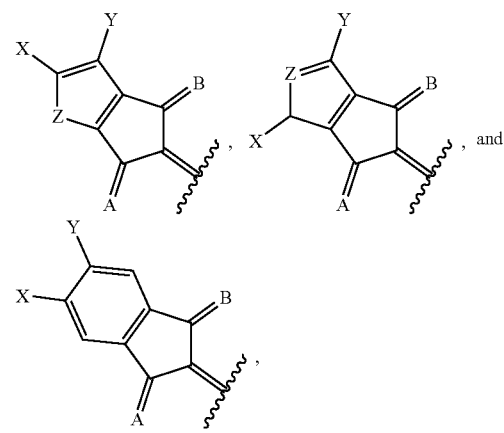

wherein A and B for each occurrence is independently selected from the group consisting of:

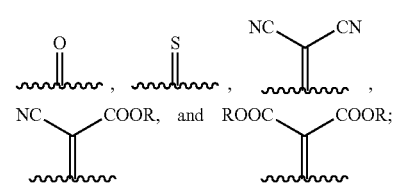

X and Y for each occurrence is independently selected from the group consisting of hydrogen, F, Cl, Br, I, CN, SCN, and alkyl;

Z for each occurrence is independently selected from the group consisting of —O—, —S—, —Se—, —Te—, and —(NR)—; and R for each occurrence is independently straight-chain alkyl, branched alkyl, or cyclic alkyl.

In certain embodiments, if Ar² is:

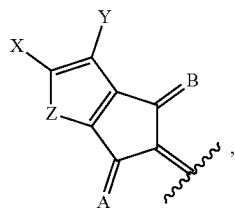

then no more than 1 instance of X or Y is hydrogen.

In certain embodiments, A is

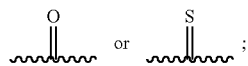

and B is

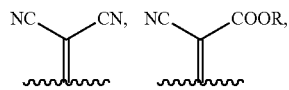

and

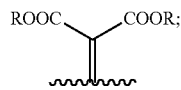

or A is

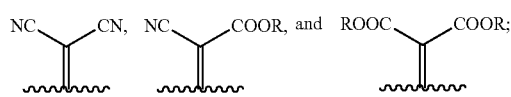

and B is

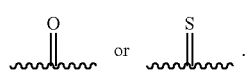

In certain embodiments, A is

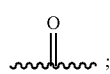

and B is

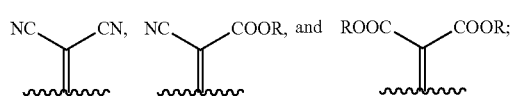

In certain embodiments, at least one of X or Y is a halogen or alkyl. In certain embodiments, X is F, Cl, Br, I, or methyl; and Y is hydrogen; or X is hydrogen; and Y is X is F, Cl, Br, I, or methyl. In certain embodiments, X is Cl, Br, or methyl and Y is hydrogen; or X is hydrogen and Y Cl, Br, or methyl. In instances in which one or more of X and Y is alkyl, the alkyl group can be $C_1$-$C_{10}$, $C_1$-$C_9$, $C_1$-$C_8$, $C_1$-$C_7$, $C_1$-$C_6$, $C_1$-$C_5$, $C_1$-$C_4$, $C_1$-$C_3$, or $C_1$-$C_2$.

In certain embodiments, Z is —S—.

In certain embodiments, Ar¹ is selected from the group consisting of:

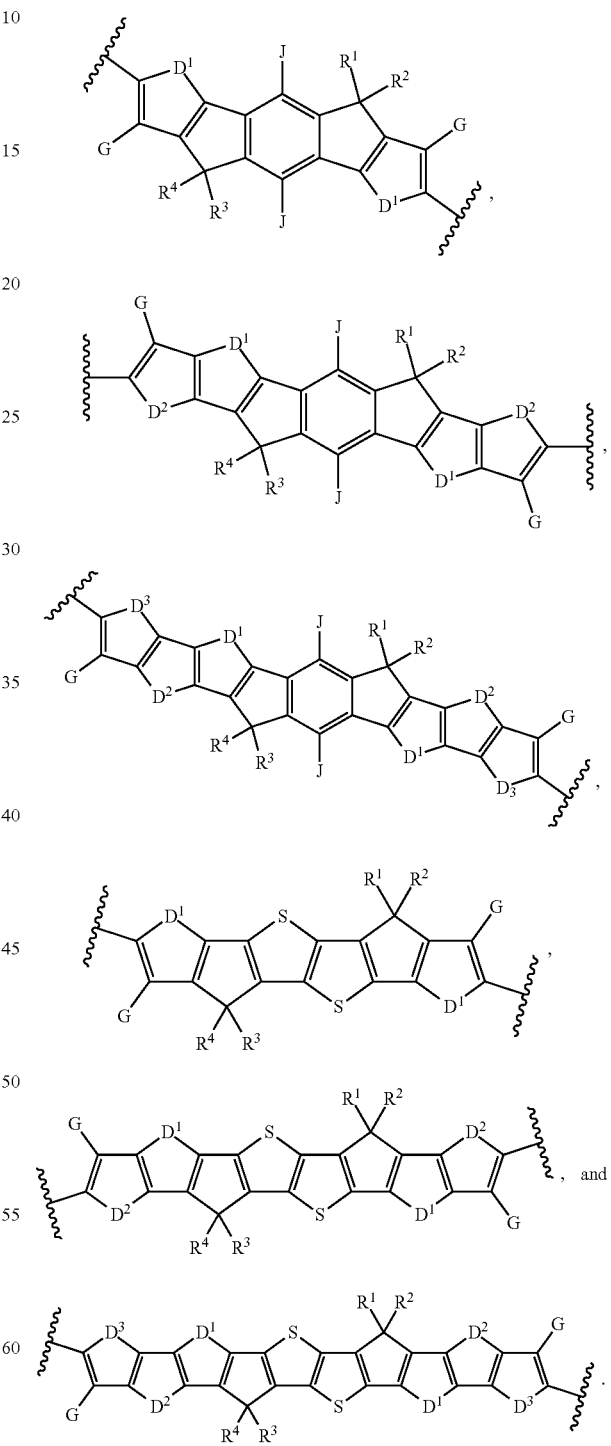

In certain embodiments, Ar¹ is selected from the group consisting of:

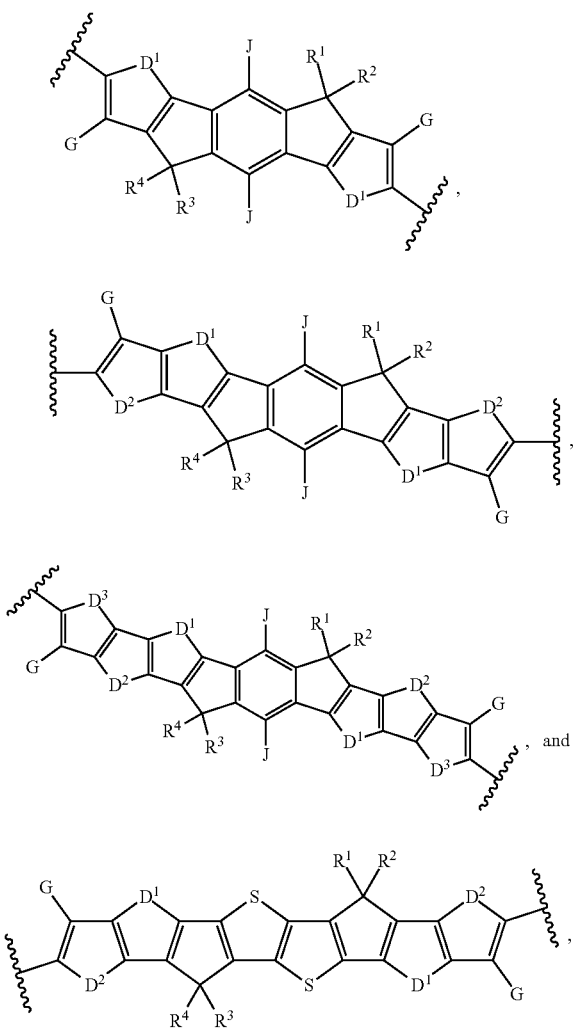
In certain embodiments, Ar² is selected from the group consisting of:
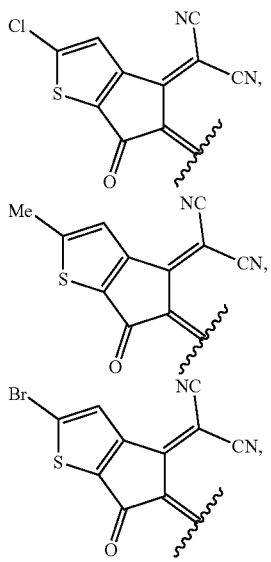
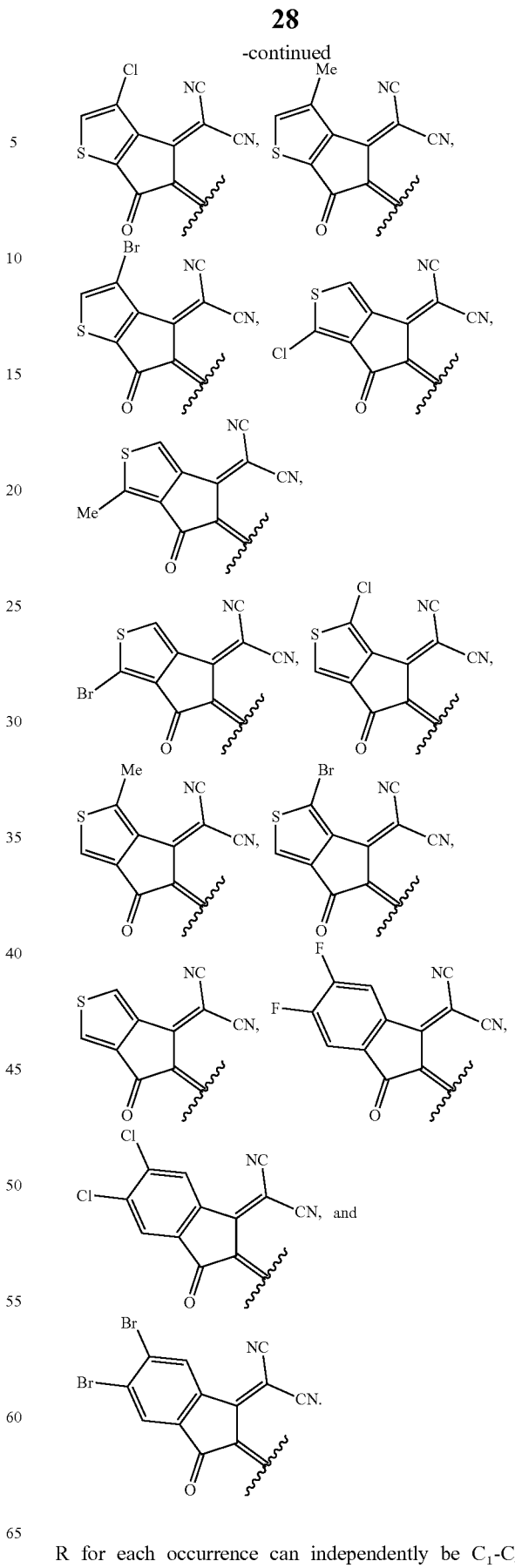
R for each occurrence can independently be $C_1$-$C_{40}$, $C_1$-$C_{35}$, $C_1$-$C_{30}$, $C_1$-$C_{25}$, $C_1$-$C_{20}$, $C_1$-$C_{15}$, $C_1$-$C_{10}$, or $C_1$-$C_5$ straight-chain alkyl; $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, or $C_3$-$C_5$ branched alkyl; or $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, or $C_3$-$C_6$ cyclic alkyl.

In certain embodiments, each of $R^1$, $R^2$, $R^3$, and $R^4$ is independently an alkyl group selected from the group consisting of $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ straight-chain alkyl; $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, and $C_3$-$C_5$ branched alkyl; $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, and $C_3$-$C_6$ cyclic alkyl; $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ alkyl aryl; and $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ alkyl heteroaryl.

In certain embodiments, each of $R^1$, $R^2$, $R^3$, and $R^4$ is a branched alkyl group represented by —$CH_2CH(R^a)(R^b)$, wherein $R^a$ for each occurrence is independently $C_1$-$C_{40}$, $C_1$-$C_{35}$, $C_1$-$C_{30}$, $C_1$-$C_{25}$, $C_1$-$C_{20}$, $C_1$-$C_{15}$, or $C_1$-$C_{10}$ alkyl; and $R^b$ is $C_1$-$C_{10}$, $C_1$-$C_8$, $C_1$-$C_6$, $C_1$-$C_4$, or $C_1$-$C_2$ alkyl.

In certain embodiments, each of $R^1$, $R^2$, $R^3$, and $R^4$ is independently represented by the moiety:

wherein $Ar^3$ is aryl or heteroaryl; and $R^c$ is an alkyl group selected from the group consisting of $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ straight-chain alkyl; $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, and $C_3$-$C_5$ branched alkyl; $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, and $C_3$-$C_6$ cyclic alkyl; $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ alkyl aryl; and $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ alkyl heteroaryl; or $R^c$ is represented by the moiety: —$CH_2CH(R^a)(R^b)$, wherein $R^a$ for each occurrence is independently selected from R is $C_1$-$C_{40}$, $C_1$-$C_{35}$, $C_1$-$C_{30}$, $C_1$-$C_{25}$, $C_1$-$C_{20}$, $C_1$-$C_{15}$, or $C_1$-$C_{10}$ alkyl; and $R^b$ is $C_1$-$C_{10}$, $C_1$-$C_8$, $C_1$-$C_6$, $C_1$-$C_4$, or $C_1$-$C_2$.

In certain embodiments, each of $D^1$, $D^2$, and $D^3$ is —S—.

In certain embodiments, J for each occurrence is independently hydrogen or an alkyl group selected from the group consisting of $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ straight-chain alkyl; $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, and $C_3$-$C_5$ branched alkyl; $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, and $C_3$-$C_6$ cyclic alkyl; $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ alkyl aryl; and $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ alkyl heteroaryl. In certain embodiments, J is a branched alkyl group represented by —$CH_2CH(R^a)(R^b)$, wherein $R^a$ for each occurrence is independently selected from $R^a$ is $C_1$-$C_{40}$, $C_1$-$C_{35}$, $C_1$-$C_{30}$, $C_1$-$C_{25}$, $C_1$-$C_{20}$, $C_1$-$C_{15}$, or $C_1$-$C_{10}$ alkyl; and $R^b$ is $C_1$-$C_{10}$, $C_1$-$C_8$, $C_1$-$C_6$, $C_1$-$C_4$, or $C_1$-$C_2$.

In instances in which J is a $C_2$-$C_{40}$ alkyl aryl or a $C_2$-$C_{40}$ alkyl heteroaryl, J can be represented by the moiety:

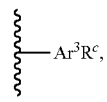

wherein $Ar^3$ is aryl or heteroaryl; and $R^c$ is an alkyl group selected from the group consisting of $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ straight-chain alkyl; $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, and $C_3$-$C_5$ branched alkyl; $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, and $C_3$-$C_6$ cyclic alkyl; $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ alkyl aryl; and $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ alkyl heteroaryl; or $R^c$ is represented by the moiety: —$CH_2CH(R^a)(R^b)$, wherein $R^a$ for each occurrence is independently selected from R is $C_1$-$C_{40}$, $C_1$-$C_{35}$, $C_1$-$C_{30}$, $C_1$-$C_{25}$, $C_1$-$C_{20}$, $C_1$-$C_{15}$, or $C_1$-$C_{10}$ alkyl; and $R^b$ is $C_1$-$C_{10}$, $C_1$-$C_8$, $C_1$-$C_6$, $C_1$-$C_4$, or $C_1$-$C_2$.

In certain embodiments,

A is selected from the group consisting of:

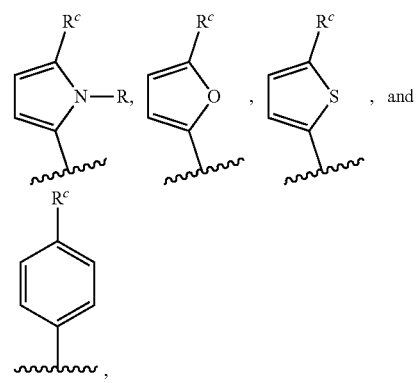

wherein $R^c$ is an alkyl group selected from the group consisting of $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ straight-chain alkyl; $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, and $C_3$-$C_5$ branched alkyl; $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, and $C_3$-$C_6$ cyclic alkyl; $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ alkyl aryl; and $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ alkyl heteroaryl; or $R^c$ is represented by the moiety: —$CH_2CH(R^a)(R^b)$, wherein $R^a$ for each occurrence is independently selected from $R^a$ is $C_2$-$C_{40}$, $C_5$-$C_{40}$, $C_5$-$C_{35}$, $C_5$-$C_{30}$, $C_5$-$C_{25}$, $C_5$-$C_{20}$, $C_5$-$C_{15}$, or $C_5$-$C_{10}$ alkyl; $R^b$ is $C_1$-$C_{10}$, $C_1$-$C_8$, $C_1$-$C_6$, $C_1$-$C_4$, or $C_1$-$C_2$; and R is as defined herein.

In certain embodiments, G for each occurrence is independently hydrogen, F, Cl, Br, or an alkyl group selected from the group consisting of $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ straight-chain alkyl; $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, and $C_3$-$C_5$ branched alkyl; $C_3$-$C_{40}$, $C_3$-$C_{35}$, $C_3$-$C_{30}$, $C_3$-$C_{25}$, $C_3$-$C_{20}$, $C_3$-$C_{15}$, $C_3$-$C_{10}$, and $C_3$-$C_6$ cyclic alkyl; $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ alkyl aryl; and $C_1$-$C_{40}$, $C_2$-$C_{40}$, $C_2$-$C_{35}$, $C_2$-$C_{30}$, $C_2$-$C_{25}$, $C_2$-$C_{20}$, $C_2$-$C_{15}$, $C_2$-$C_{10}$, $C_2$-$C_5$, $C_1$-$C_{15}$, $C_1$-$C_{10}$, and $C_1$-$C_5$ alkyl heteroaryl. In certain embodiments, G is hydrogen, chloride, or an alkyl group. In certain embodiments, G is hydrogen.

In certain embodiments, the compound is selected from the group consisting of:

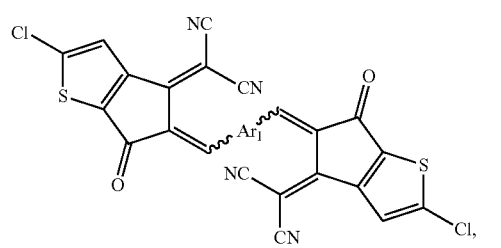

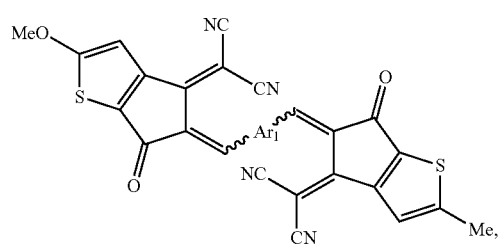

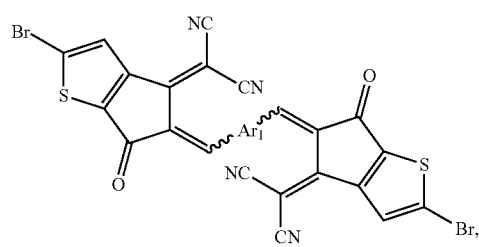

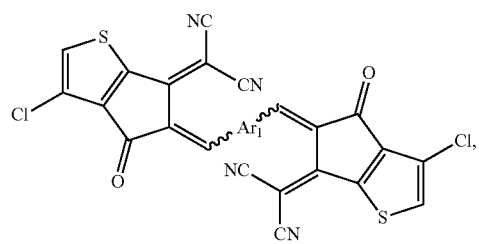

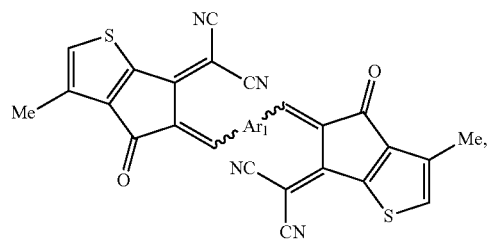

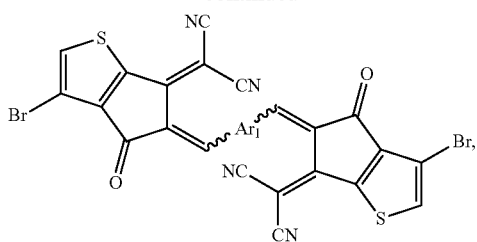

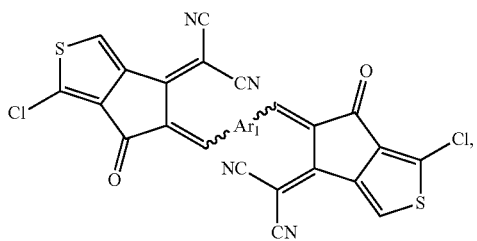

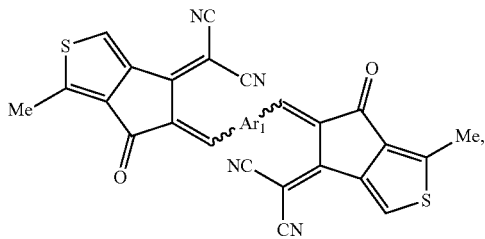

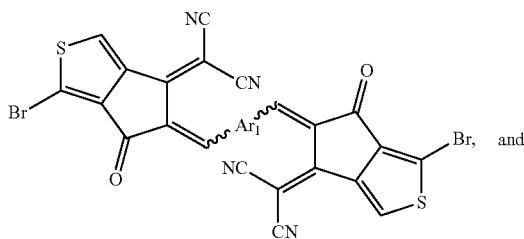

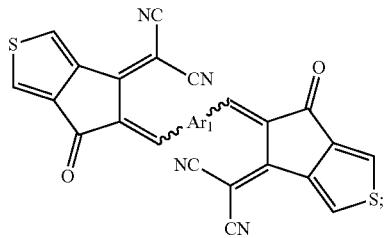

$Ar^1$ is selected from the group consisting of:

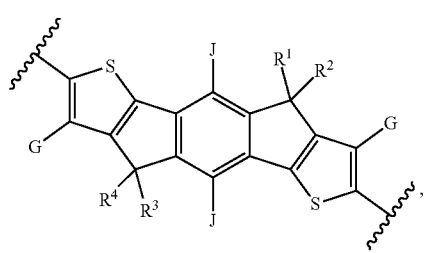

33
-continued
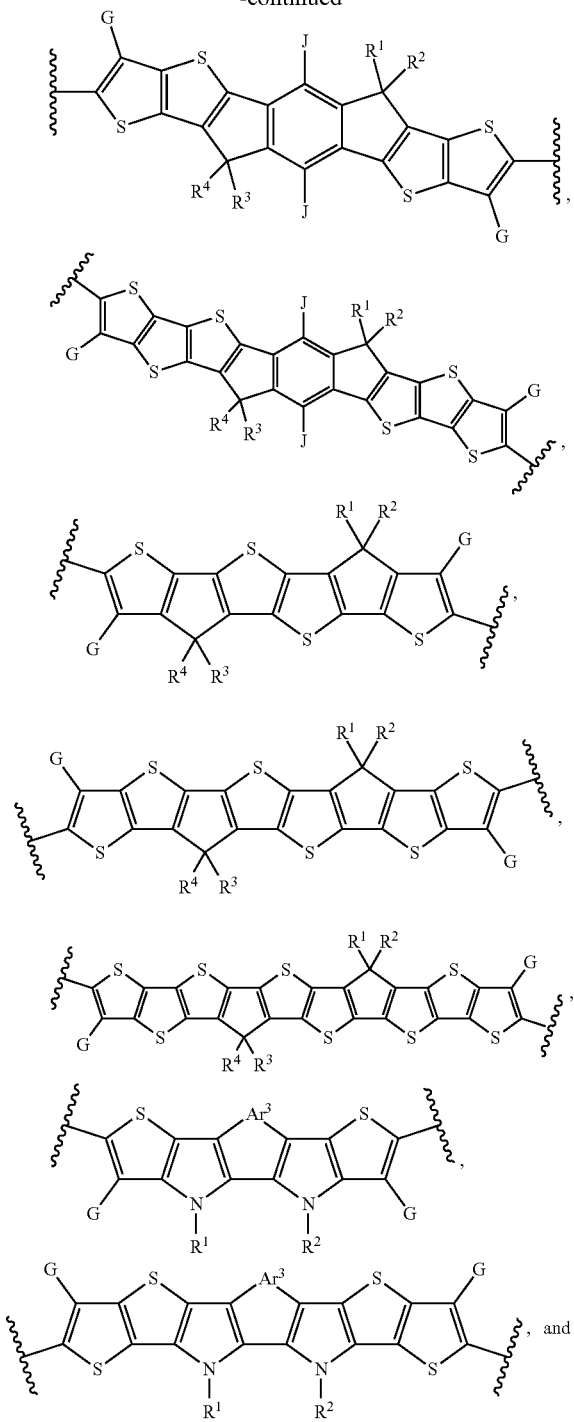
34
-continued
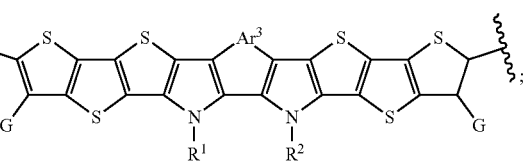
and
Ar³ is selected from the group consisting of:
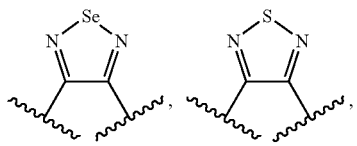
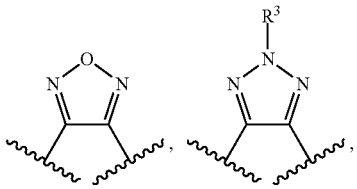
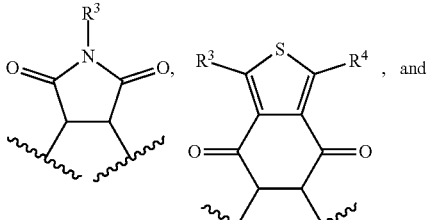
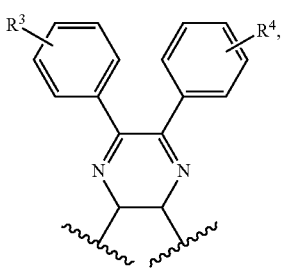
wherein J, G, R, $R^1$, $R^2$, $R^3$ and $R^4$ are as defined herein.
In certain embodiments, the compound is selected from the group consisting of:
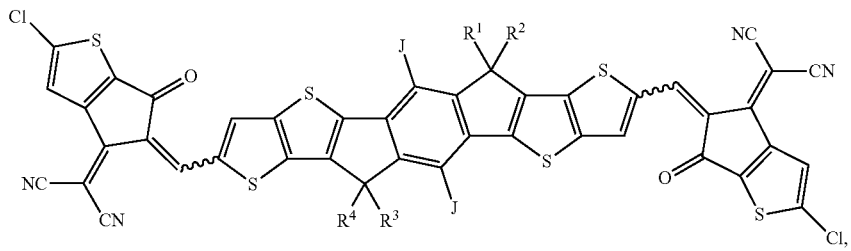

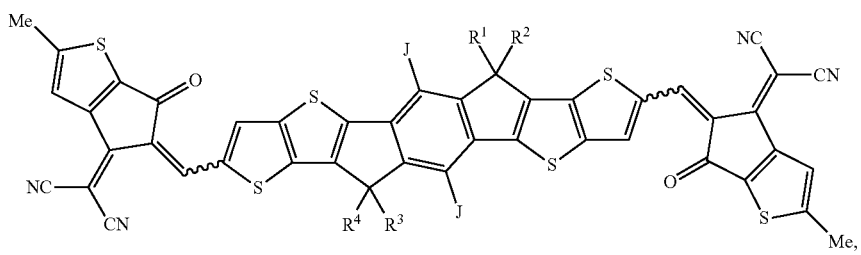
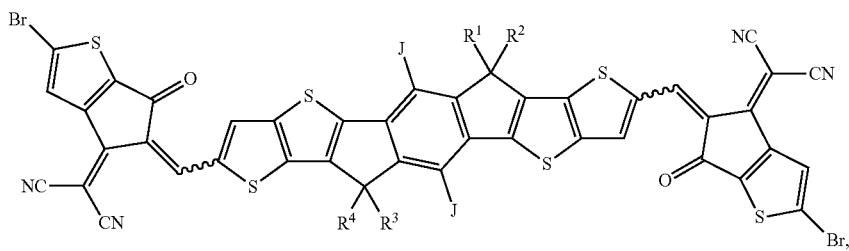
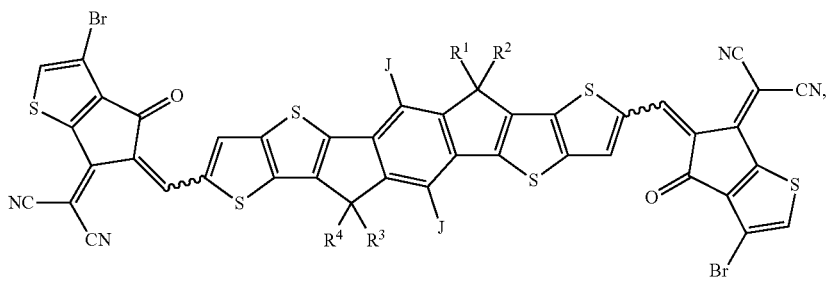
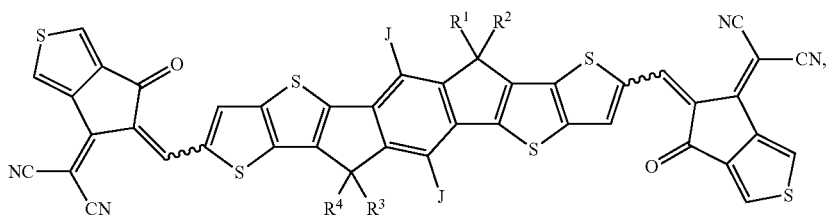
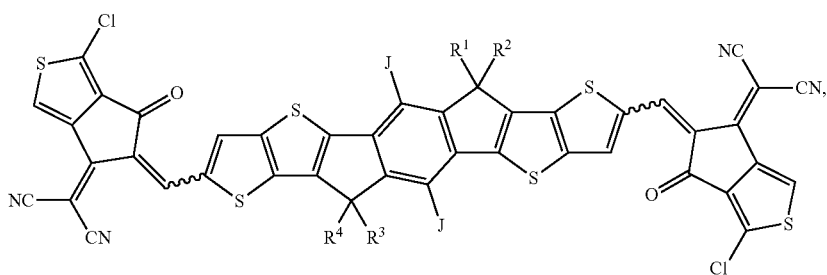
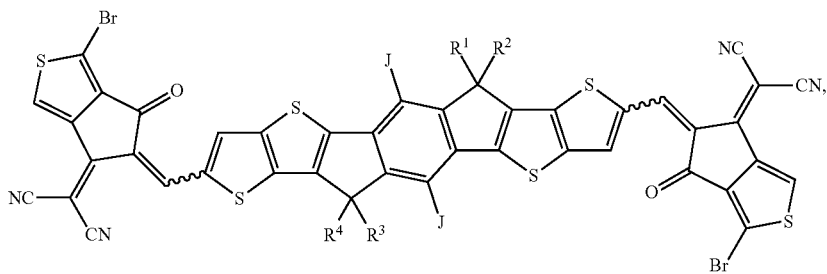

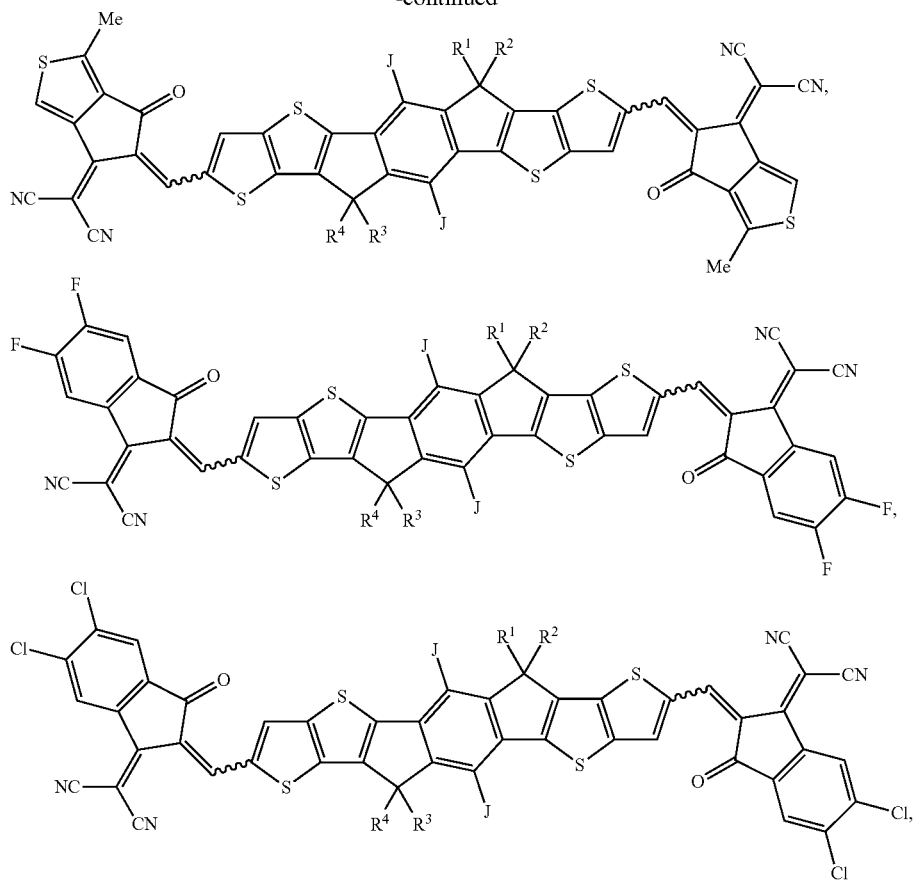
wherein $R^1$, $R^2$, $R^3$, and $R^4$ and J are as defined herein.
In certain embodiments, the compound is selected from the group consisting of:
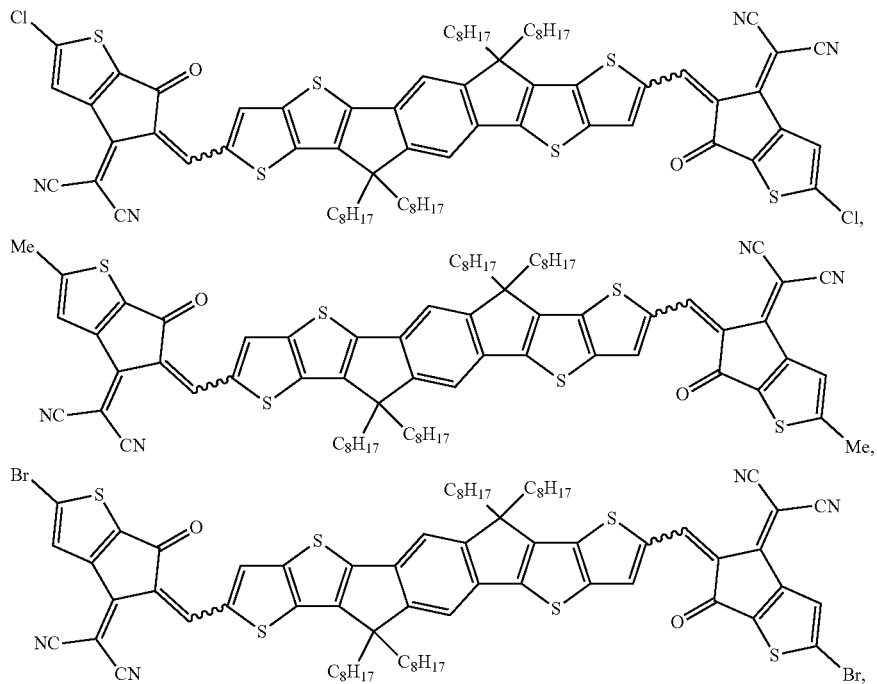

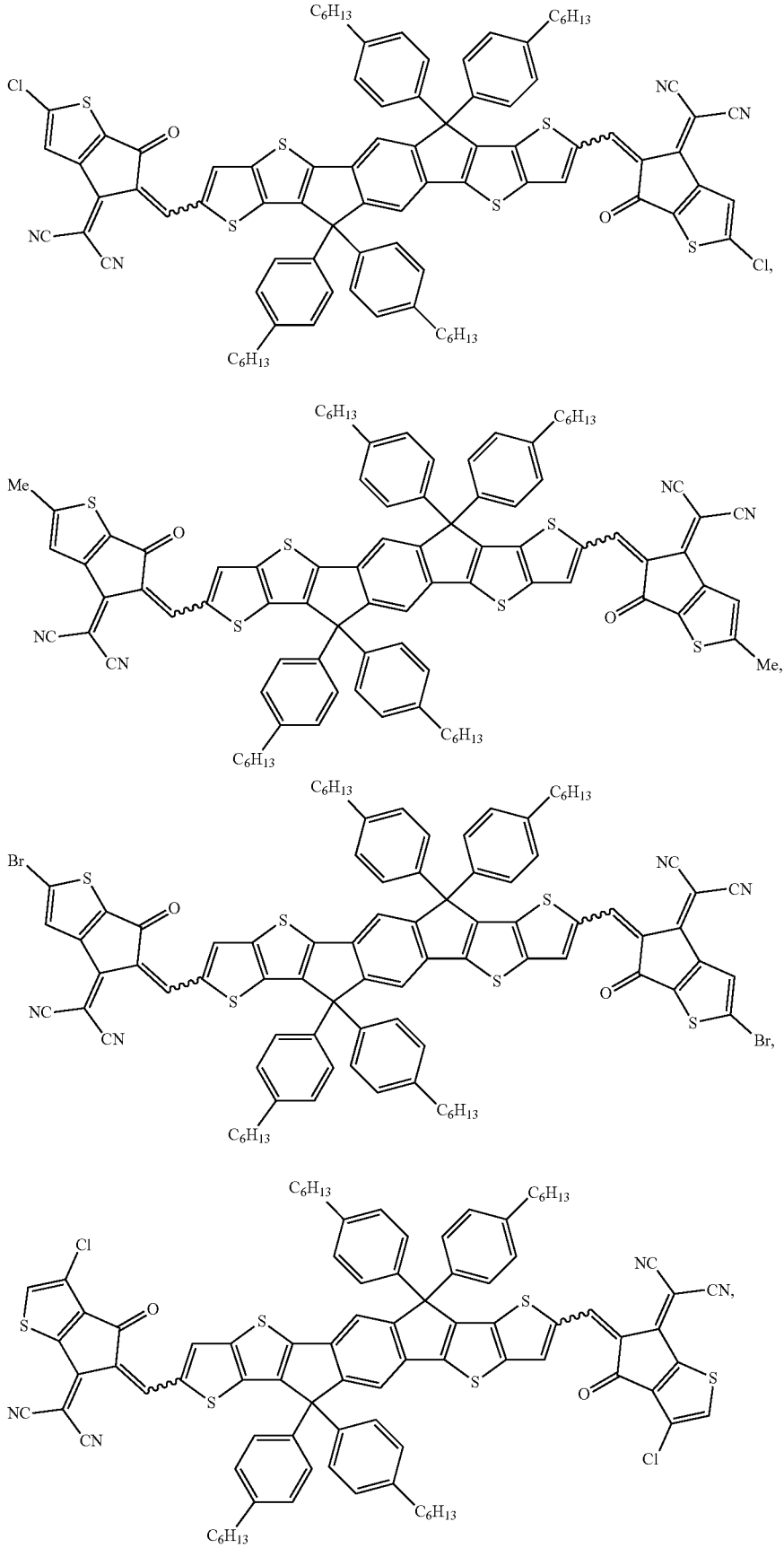

-continued
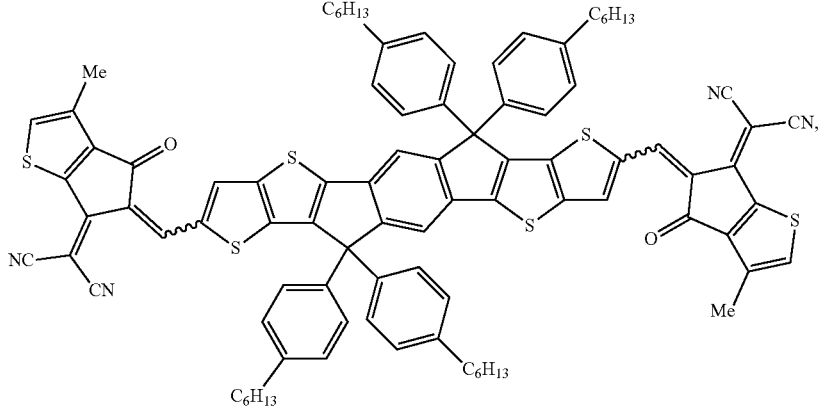
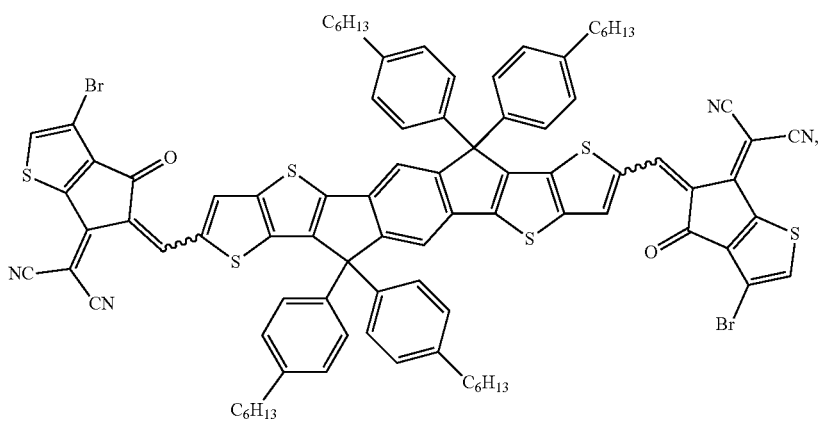
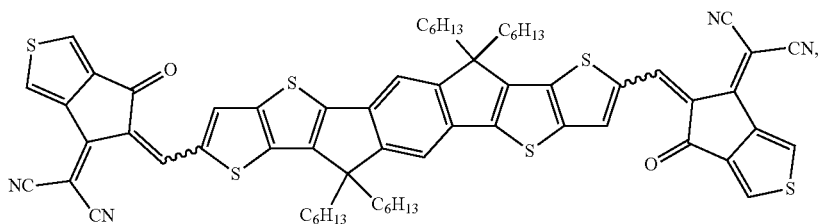
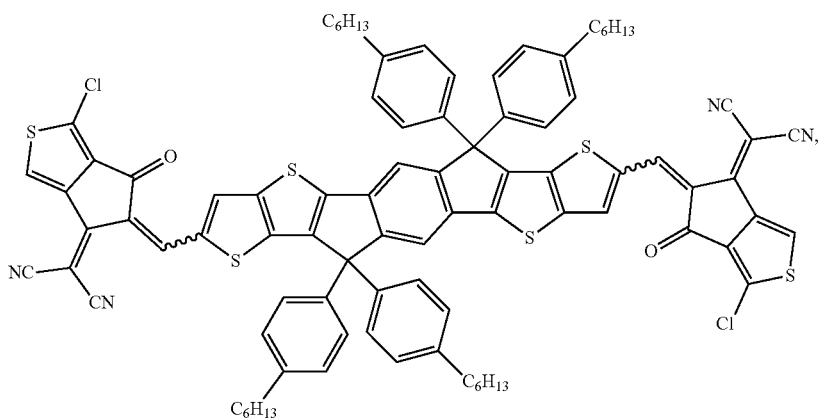

-continued
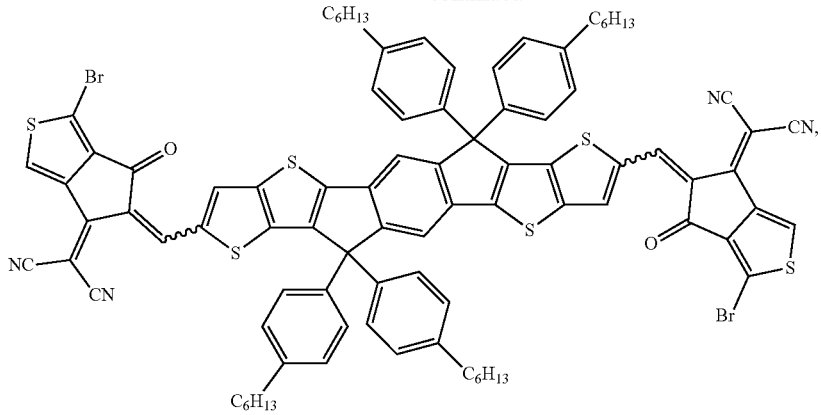
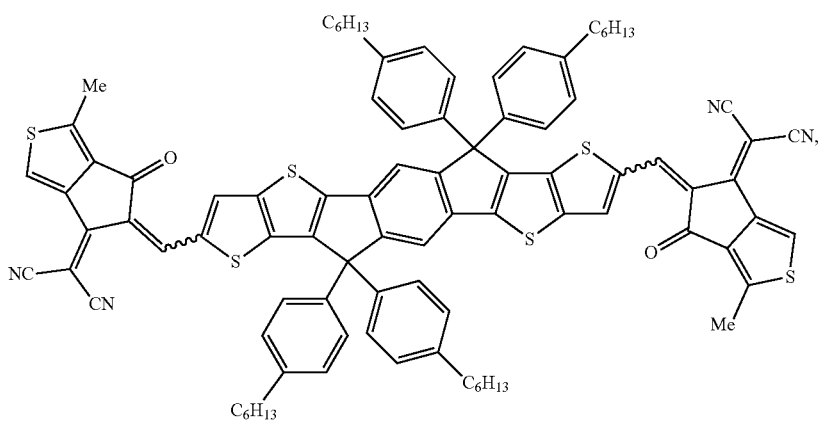
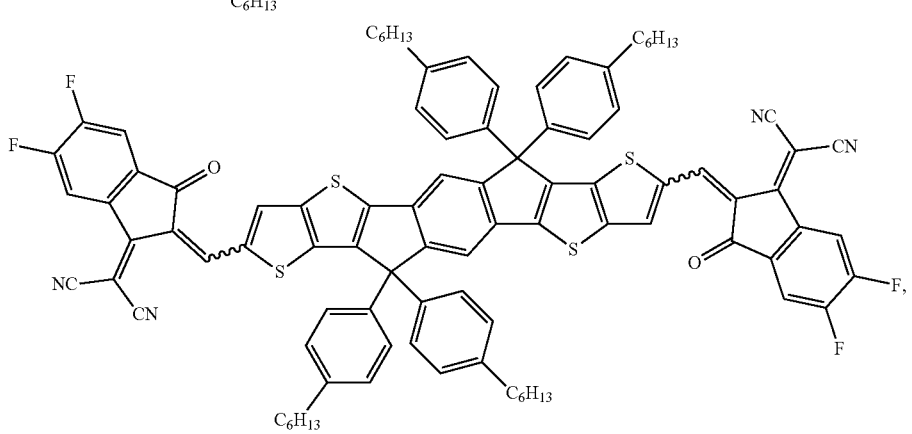
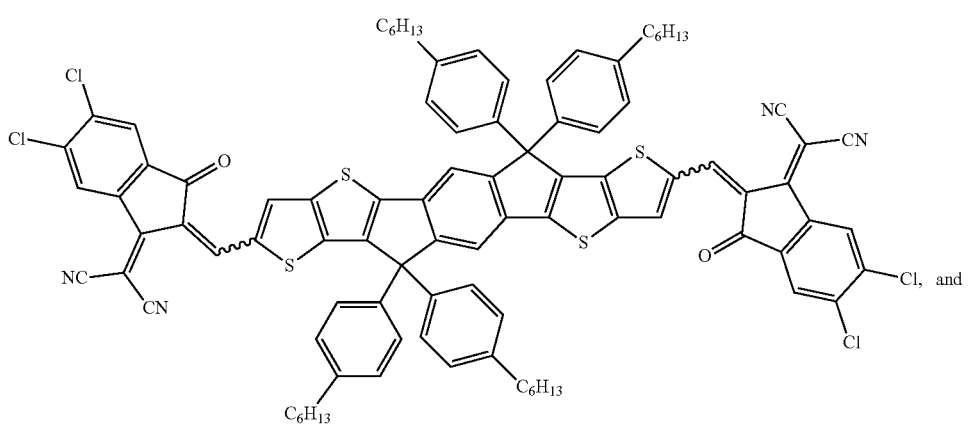

-continued

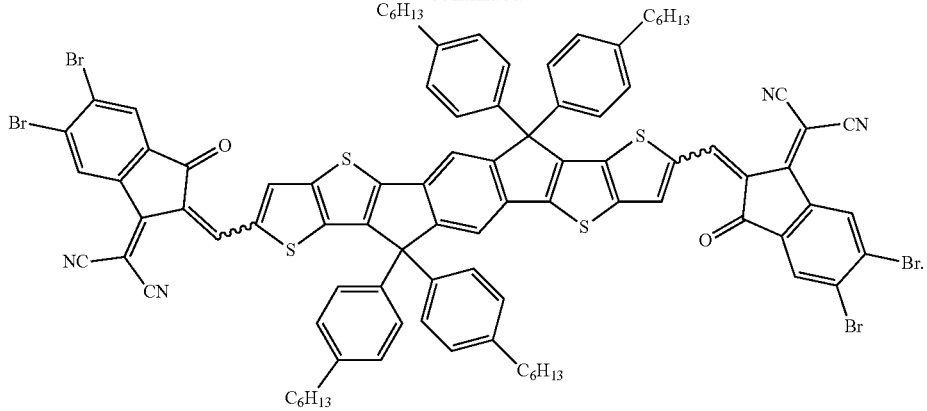

Also provided herein is an A-D-A SMA compound comprising the following aromatic formula:

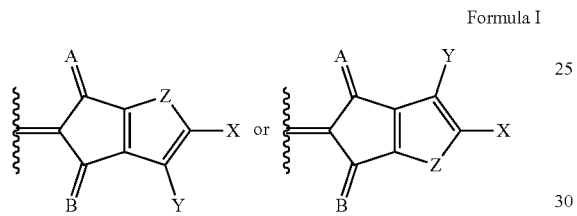
Formula I wherein X and Y are independently selected from the group consisting of H, F, Cl, Br, I, CN, and SCN, with the proviso total number of H in X and Y is 0 or 1;

Z is selected from the group consisting of O, S, Se, Te, and N—R1, wherein R1 is independently a straight-chain, branched, or cyclic alkyl group; and A and B are independently selected from:

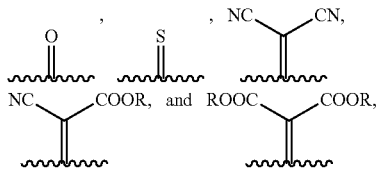

wherein R is independently a straight-chain, branched, or cyclic alkyl group.

In certain embodiments the, the compound has the following aromatic formula:

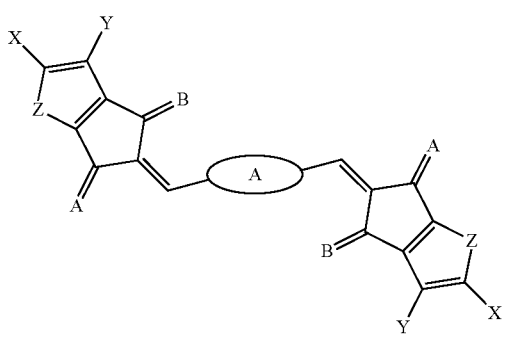

wherein A is selected from:

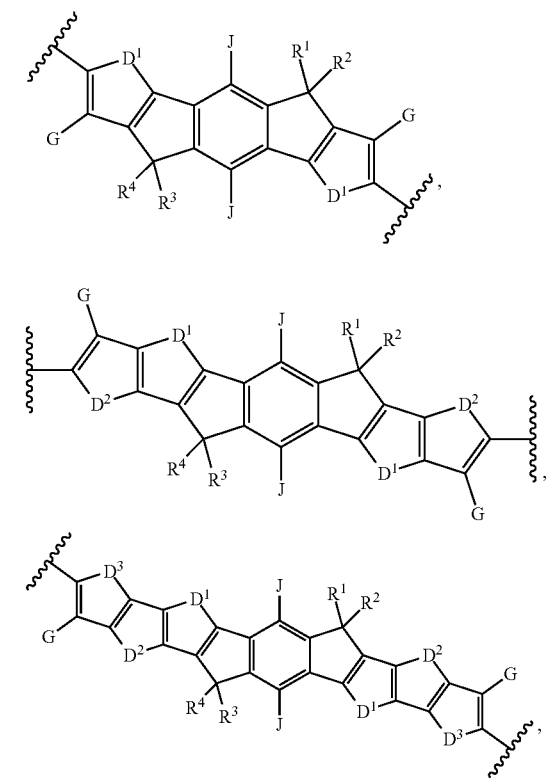

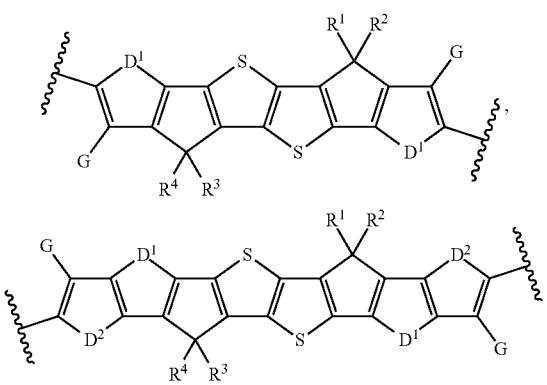

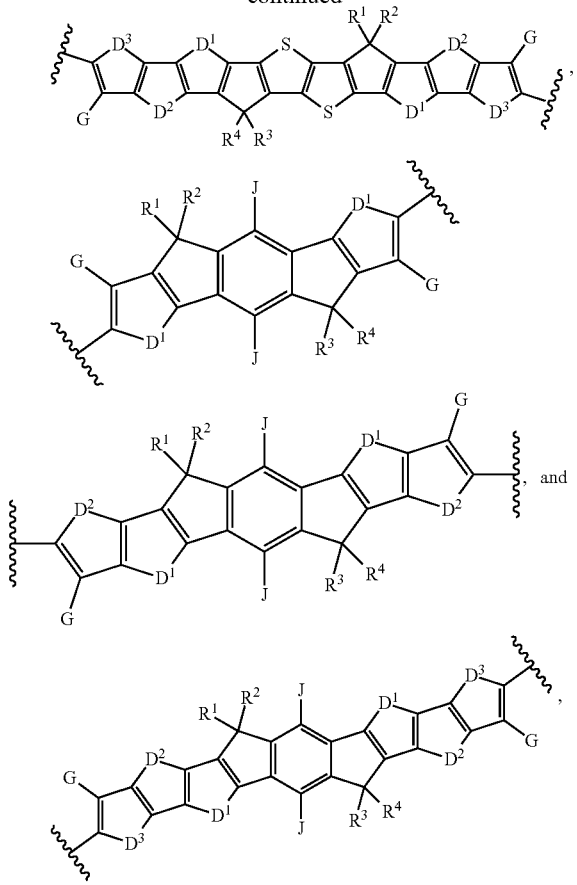

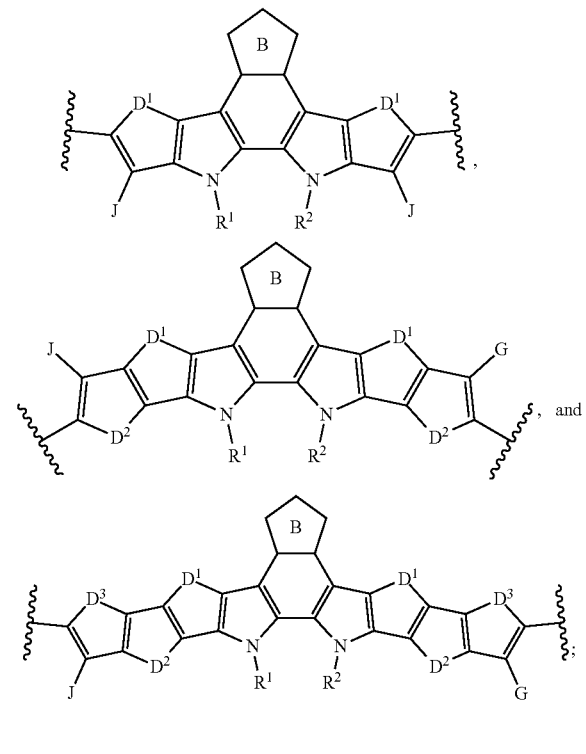

wherein R¹, R², R³ and R⁴ are independently selected from the group consisting of straight-chain, branched, cyclic alkyl, alkyl phenyl, alkyl thienyl and other alkyl aryl with 2-40 C atoms, wherein one or more non-adjacent C atoms are optionally replaced by —O—, —S—, —C(O)—, —C(O—)—O—, —O—C(O)—, —O—C(O)—O—, —CR⁵=CR⁶—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups;

D¹, D² and D³ are independently selected from the group consisting of O, S, Se, Te, NR⁵, C(R⁵)₂, wherein R⁵ are independently selected from a straight-chain, branched, and cyclic alkyl group; and J and G are independently selected from H, F, Cl, Br, CN, OR⁵, NHR⁵, straight-chain, branched, cyclic alkyl, alkyl phenyl, alkyl thienyl and other alkyl aryl with 2-40 C atoms, wherein one or more non-adjacent C atoms are optionally replaced by —O—, —S—, —C(O)—, —C(O—)—O—, —O—C(O)—, —O—C(O)—O—, —CR⁶=CR⁷—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups.

In certain embodiments, A is a moiety having the formula:

B is selected from the group consisting of:

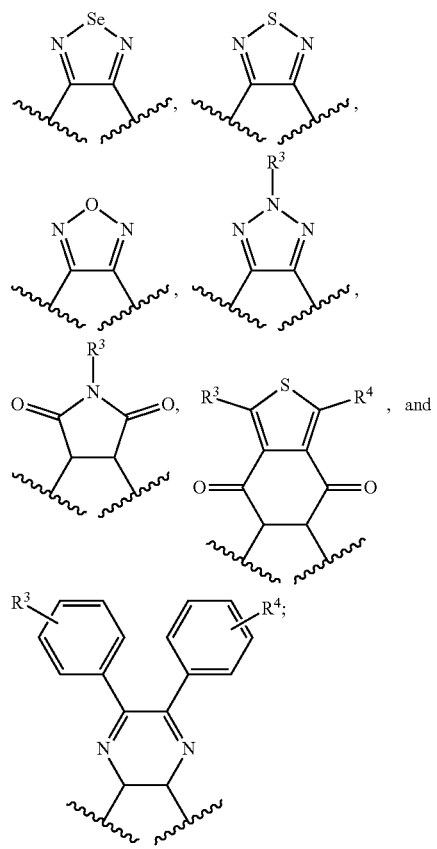

R, $R^1$, and $R^2$ are independently selected from the group consisting of straight-chain, branched, cyclic alkyl, alkyl phenyl, alkyl thienyl and other alkyl aryl with 2-40 C atoms, wherein one or more non-adjacent C atoms are optionally replaced by —O—, —S—, —C(O)—, —C(O—)—O—, —O—C(O)—, —O—C(O)—O—, —$CR^5$=$CR^6$—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups;

$D^1$, $D^2$ and $D^3$ are independently selected from the group consisting of O, S, Se, Te, $NR^5$, and $C(R^5)_2$;

$R^5$, $R^6$, and $R^7$ are independently selected from a straight-chain, branched, or cyclic alkyl group; and J and G are independently selected from H, F, Cl, Br, CN, $OR^5$, $NHR^5$, straight-chain, branched, cyclic alkyl, alkyl phenyl, alkyl thienyl and other alkyl aryl with 2-40 C atoms, wherein one or more non-adjacent C atoms are optionally replaced by —O—, —S—, —C(O)—, —C(O—)—O—, —O—C(O)—, —O—C(O)—O—, —$CR^6$=$CR^7$—, or —C≡C—, and wherein one or more H atoms are optionally replaced by F, Cl, Br, I, or CN or denote aryl, heteroaryl, aryloxy, heteroaryloxy, arylcarbonyl, heteroarylcarbonyl, arylcarbonyloxy, heteroarylcarbonyloxy, aryloxycarbonyl, or heteroaryloxycarbonyl having 4 to 30 ring atoms unsubstituted or substituted by one or more non-aromatic groups.

Also provided herein is a method of preparing the compound of Formula 1, the method comprising: contacting a compound of Formula 1a:

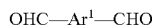

OHC—$Ar^1$—CHO     1a with a compound selected from the group consisting of:

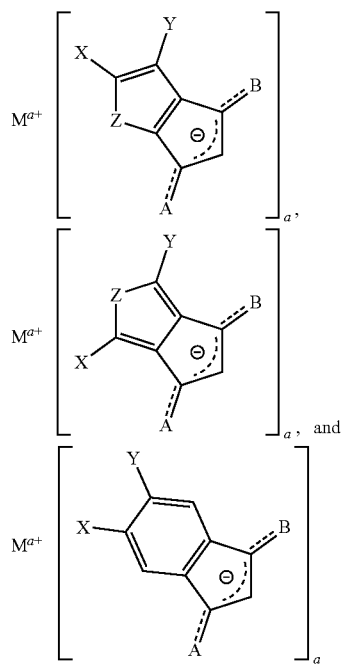

wherein A, B, X, Y, Z, and $Ar^1$ are as defined herein; M is Li, Cs, Na, Mg, or Ca; and a corresponds to the oxidation state of M, i.e. 1+ in the case Li, Cs, and Na; and 2+ for Mg and Ca; or M represents the conjugate acid of an amine base; thereby forming the compound of Formula 1.

The amine base can be any amine base known in the art. In certain embodiments, the amine base is selected from the group consisting of ammonia, mono-, di-, or trialkyl-amines, heteroaryl amines, heterocycloalkyl amines, and the like. Exemplary amine bases include, but are not limited to Hunig's base, pyridine, pyrazine, trimethylamine, morpholine, N-methyl morpholine, piperidine, piperazine, pyrrolidine, DABCO, quinuclidine, TBD, DBU, DBN, DMAP, and the like.

The present disclosure also provides a photoactive layer comprising at least one compound described herein and a non-fullerene electron acceptor. In certain embodiments, the non-fullerene electron acceptor is a donor-acceptor polymer. The donor-acceptor polymer can be any donor-acceptor polymer known in the art. Preferably, the lowest unoccupied molecular orbital (LUMO) energy levels of the A-D-A SMA compound described herein align with the energy levels of the highest occupied molecular orbital (HOMO) energy levels of the donor-acceptor polymer. Selection of a suitable donor-acceptor polymer is well within the skill of a person of ordinary skill in the art.

In certain embodiments, the active layer thickness ranges from 10 to 600 nm; 50 to 600 nm; 50 to 550 nm; or 70 to 505 nm.

In certain embodiments, the donor-acceptor polymer is represented by a polymer comprising repeating unit of Formula 4:

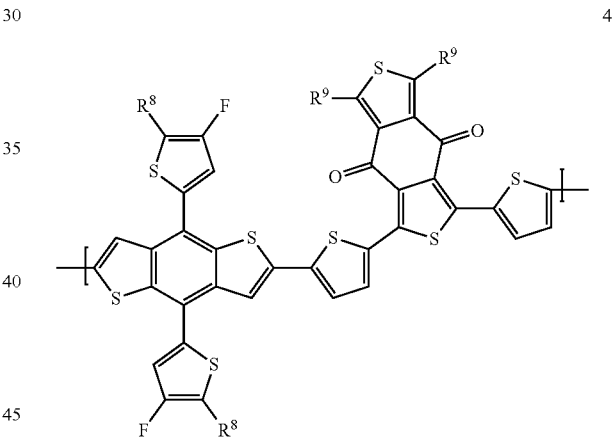

4 wherein $R^8$ is $C_4$-$C_{20}$ alkyl; and $R^8$ is $C_4$-$C_{20}$ alkyl. In certain embodiments, each of $R^8$ and $R^9$ are independently —$CH_2CH(R^a)(R^b)$, wherein $R^a$ for each occurrence is independently selected from $R^a$ is $C_1$-$C_{40}$, $C_1$-$C_{35}$, $C_1$-$C_{30}$, $C_1$-$C_{25}$, $C_1$-$C_{20}$, $C_1$-$C_{15}$, or $C_1$-$C_{10}$ alkyl; and $R^b$ is $C_1$-$C_{10}$, $C_1$-$C_8$, $C_1$-$C_6$, $C_1$-$C_4$, or $C_1$-$C_2$. In certain embodiments, each of $R^8$ and $R^9$ is —$(CH_2)CH(C_2H_5)(C_4H_9)$(PBDB-TF).

Additional exemplary donor-acceptor polymers include, but are not limited to, J51, J52, J61, J71, PM6, PTQ1, P3HT, PCDT-DFBT, PffBT4T-2DT, PffBT4T-2OD, FTAZ, PTB7, PBDB-T, PBDB-TF, PBDB-T1, PBDB-T-2Cl, PBDB-T-2F, P2F-EHp, and the like.

Also provided herein is an OE device comprising at least compound described herein. In certain embodiments, the OE device comprises a photoactive layer comprising at least compound described herein.

In certain embodiments, the OE device is selected from the group consisting of organic field effect transistors (OFET), integrated circuits (IC), thin film transistors (TFT), radio frequency identification (RFID) tags, organic light emitting diodes (OLED), organic light emitting transistors (OLET), electroluminescent displays, organic photovoltaic (OPV) cells, organic solar cells (O-SC), flexible OPVs and O-SCs, organic laser diodes (O-laser), organic integrated circuits (O-IC), lighting devices, sensor devices, electrode materials, photoconductors, photodetectors, electrophotographic recording devices, capacitors, charge injection layers, Schottky diodes, planarising layers, antistatic films, conducting substrates, conducting patterns, photoconductors, electrophotographic devices, organic memory devices, biosensors and biochips. In certain embodiments, the OE device is a photovoltaic cell.

In an exemplary embodiment, an organic electronic (OE) device comprises a coating or printing ink containing the formulation. Another exemplary embodiment is further characterized in that the OE device is an organic solar cells (OSC) device.

Formulations of the present teachings can exhibit semiconductor behavior such as optimized light absorption/charge separation in a photovoltaic device; charge transport/recombination/light emission in a light-emitting device; and/or high carrier mobility and/or good current modulation characteristics in a field-effect device. In addition, the present formulations can possess certain processing advantages such as solution-processability and/or good stability (e.g., air stability) in ambient conditions. The formulations of the present teachings can be used to prepare either p-type (donor or hole-transporting), n-type (acceptor or electron-transporting), or ambipolar semiconductor materials, which in turn can be used to fabricate various organic or hybrid optoelectronic articles, structures and devices, including organic photovoltaic devices and organic light-emitting transistors.

EXAMPLES

Example 1—Synthetic Route to C8-ITCC-Cl

Step 1: Preparation of 5-chlorothiophene-2-carbonyl chloride

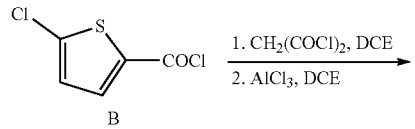

Synthesis of 5-chlorothiophene-2-carbonyl chloride (B). To a solution of 5-chlorothiophene-2-carboxylic acid (A, 3.25 g, 20 mmol) in anhydrous dichloromethane (40 mL) was added thienyl chloride (40 mL, 1.0 M in dichloromethane). After the mixture was stirred at r.t. overnight, dichloromethane and thienyl chloride were evaporated under reduced pressure. The resulting yellow solid was dried under high vacuum and used for the next step without further purification.

Step 2: Preparation of 2-chloro-4H-cyclopenta[b]thiophene-4,6(5H)-dione

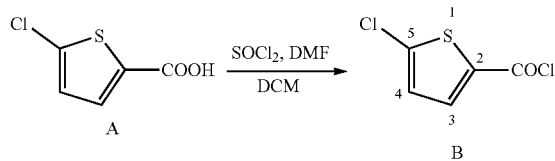

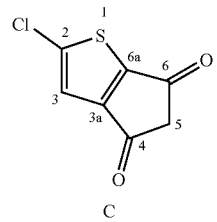

Synthesis of 2-chloro-4H-cyclopenta[b]thiophene-4,6 (5H)-dione (C). Towards a mixture of anhydrous aluminum chloride (6.7 g, 50 mmol) and 5-chlorothiophene-2-carbonyl chloride (B) in dry 1,2-dichloroethane (60 mL) was added with malonyl dichloride (6 g, 40 mmol) under vigorous stirring in an ice bath. The reaction was allowed to warm to 80° C. and stirred for 12 hours. The mixture was poured into ice water and extracted with chloroform. The combined organic extracts were washed with 10% hydrochloric acid and water before drying over sodium sulfate. After the organic phase was concentrated, silica gel column chromatography was carried out (eluent: dichloromethane) to afford the product as a brown solid (2.8 g, 75% for two steps). $^1$H NMR (400 MHz, CDCl$_3$): δ (ppm) 7.26 (s, 1H), 3.34 (s, 2H). $^{13}$C NMR (100 MHz, CDCl$_3$): δ (ppm) 189.3, 187.6, 147.4, 120.2, 47.4. MALDI-TOF MS: Calcd for $C_{26}H_{16}S_4$ (M$^+$): 185.9542. Found: 185.9536.

Step 3: Preparation of 2-(2-chloro-6-oxo-5,6-dihydro-4H-cyclopenta[b]thiophen-4-ylidene)malononitrile

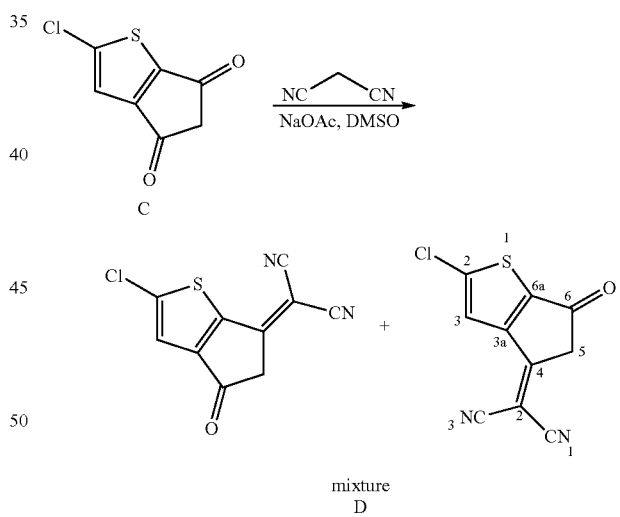

Synthesis of TIC-Cl (D). Sodium acetate (162 mg, 1.969 mmol) was added to the mixture of 2-chloro-4H-cyclopenta[b]thiophene-4,6(5H)-dione (C, 334 mg, 1.789 mmol) and malononitrile (130 mg, 1.969 mmol) in anhydrous DMSO (10 mL) at room temperature. The mixture was stirred for 2 h at room temperature. A purple coloration occurred immediately, and the suspended solid was dissolved slowly. The mixture was poured into water and acidified to pH 1-2 by addition of hydrochloric acid. The suspension was stirred for 10 min. Then the solid material was filtered off, and washed thoroughly with water. The pure product was obtained by silica gel chromatography (eluent: dichloromethane) to obtain an orange solid (270 mg, 64%). The product contained two isomers (ratio: ~2:1) and was used without further separation. $^1$H NMR (400 MHz, CDCl$_3$): δ (ppm) 7.77 (s, 1H), 3.81 (s, 2H); 7.31 (s, 1H), 3.80 (s, 2H). $^{13}$C NMR (100 MHz, CDCl$_3$): δ (ppm) 186.9, 185.1, 160.9, 160.7, 154.0, 152.7, 152.3, 148.8, 148.7, 148.2, 121.8, 120.8, 112.2, 111.7, 111.4, 111.3, 78.28, 76.11, 44.9, 44.7. MALDI-TOF MS: Calcd for C$_{26}$H$_{16}$S$_4$ (M$^+$): 233.9655. Found: 233.9651.

Step 4: Preparation of C8-ITCC-Cl

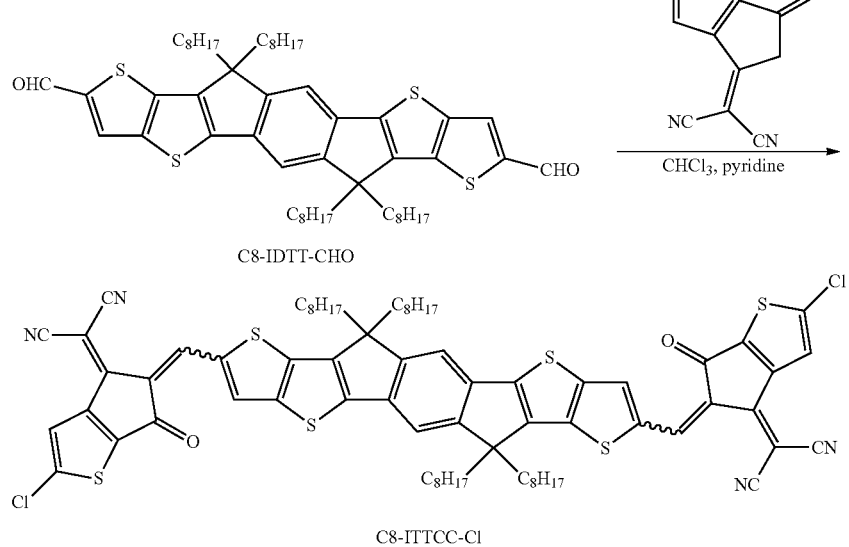

C8-IDTT-CHO

C8-ITTCC-Cl

Synthesis of C8-ITCC-Cl. C8-IDTT-CHO (30 mg, 0.026 mmol) and TIC-Cl (31 mg, 0.13 mmol) were dissolved in anhydrous CHCl3 (10 mL). Anhydrous pyridine (1 mL) was then added and the mixture was stirred and refluxed overnight. The resulting mixture was extracted with chloroform, washed with water, and dried over MgSO4. After removing the solvent, the crude product was purified on a silica-gel column chromatography (eluent:hexane:dichloromethane=1:2) to afford C8-ITCC-Cl as a blue solid (29 mg, 84%). $^1$H NMR (400 MHz, CDCl$_3$): δ (ppm) 8.75 (s, 2H), 8.16 (s, 2H), 7.89 (s, 2H), 7.49 (s, 2H), 2.41-2.05 (m, 8H), 1.25-1.07 (m, 40H), 0.97-0.72 (t, 12H). $^{13}$C NMR (100 MHz, CDCl$_3$): δ (ppm) MALDI-TOF MS: Calcd for C$_{26}$H$_{16}$S$_4$ (M$^+$): 1314.3670. Found: 1314.3667.

Example 2—Optical and Electrochemical Properties

Example 2a: Optical Properties

Film UV-Vis absorption spectra of polymers from Example 2 were acquired on a Perkin Elmer Lambda 20 UV/VIS Spectrophotometer. All film samples were spin-cast on ITO/ZnO substrates. Solution UV-Vis absorption spectra at elevated temperatures were collected on a Perkin Elmer Lambda 950 UV/VIS/NIR Spectrophotometer. The temperature of the cuvette was controlled with a Perkin Elmer PTP 6+6 Peltier System, which is supplied by a Perkin Elmer PCB 1500 Water Peltier System. Before each measurement, the system was held for at least 10 min at the target temperature to reach thermal equilibrium. A cuvette with a stopper (Sigma Z600628) was used to avoid volatilization during the measurement. The onset of the absorption is used to estimate the polymer bandgap.

Example 2b: Electronic Properties

Cyclic voltammetry was carried out on a CHI760E electrochemical workstation with three electrodes configuration, using Ag/AgCl as the reference electrode, a Pt plate as the counter electrode, and a glassy carbon as the working electrode. Polymers were drop-cast onto the electrode from DCB solutions to form thin films. 0.1 mol L$^{-1}$ tetrabutylammonium hexafluorophosphate in anhydrous acetonitrile was used as the supporting electrolyte. Potentials were referenced to the ferrocenium/ferrocene couple by using ferrocene as external standards in acetonitrile solutions. The scan rate is 0.1 V s$^{-1}$.

Example 3—Device Fabrication

Diethylzinc (15% wt in toluene) and molybdenum oxide (MoO$_3$) were purchased from Sigma-Aldrich and used as received without further treatment. Pre-patterned ITO-coated glass substrates were cleaned by sequential sonication in soap deionized water, deionized water, acetone, and isopropanol for 30 min of each step. Active layer solutions (D:A ratio 1:1 w/w) were prepared in chloroform with 0.5% 1,8-diiodooctane (polymer concentration: 8 mg mL-1). To completely dissolve the polymer, the active layer solution should be stirred on a hotplate at 65° C. for at least 1 hour. The active layers were spin-coated with a speed of 2000-

3000 rpm at room temperature. The active layers were then treated with vacuum to remove the solvent. Subsequently, the blend films were thermally annealed at 100° C. for 5 min before being transferred to the vacuum chamber of a thermal evaporator inside the same glovebox, and a thin layer (6 nm) of $MoO_3$ was deposited as the anode interlayer, followed by the deposition of 100 nm of Al as the top electrode at a vacuum level of ~1.0×10−4 Pa. All devices were encapsulated using epoxy and thin glass slides inside the glovebox. Device J-V characteristics were measured under AM 1.5 G (100 mW cm$^{-2}$) using a Newport solar simulator in ambient atmosphere. The light intensity was calibrated using a standard Si diode (with KG5 filter, purchased from PV Measurement) to bring spectral mismatch to unity. J-V characteristics were recorded using a Keithley 2400 source meter unit. Typical cells have devices area of 5.9 mm$^2$, defined by a metal mask with an aperture aligned with the device area.

Example 4—PBDB-TF:C8-ITCC and PBDB-TF:C8-ITCC-Cl Device Performance

To investigate the photovoltaic performances of the two SMAs, solar cell devices based on PBDB-TF:SMAs were fabricated. Table 1 summarizes the device properties of PBDB-TF:C8-ITCC and PBDB-TF:C8-ITCC-Cl under the optimized processing conditions. The PBDB-TF:C8-ITCC-Cl devices shows a VOC of 0.95 V that is 0.09 V lower than the PBDB-TF:C8-ITCC ones (1.04 V), which is primarily due to the lower LUMO levels of C8-ITCC-Cl. Despite the lower VOC, the device based on C8-ITCC-Cl exhibits both a higher JSC of 18.5 mA/cm$^2$ and a higher FF of 0.73 compared with those based on C8-ITCC (JSC=16.2 mA/cm$^2$, FF=0.63). Consequently, a high PCE of 12.7% was achieved by the PBDB-TF:C8-ITCC-Cl combination, which outperformed the PBDB-TF:C8-ITCC one (10.8%).

TABLE 1

Photovoltaic parameters of the PBDB-TF:C8-ITCC and PBDB-TF:C8-ITCC-Cl devices with the inverted structure under illumination of 100 mW/cm$^2$.

| Material combinations | Voc (V) | Jsc (mA cm') | FF (%) | PCEa (%) | Phille (cm2 V' sA) |
|---|---|---|---|---|---|
| PBDB-TF:C8-ITCC | 1.04 ± 0.01 | 16.1 ± 0.1 | 63 ± 1 | 10.5 ± 0.2 (10.8) | 6.7/2.7 × 10$^{-4}$ |
| PBDB-TF:C8-ITCC-Cl | 0.95 ± 0.01 | 17.9 ± 0.1 | 73 ± 1 | 12.4 ± 0.2 (12.7) | 9.1/6.6 × 10$^{-4}$ |

$^a$ Average values from 20 devices with the highest values shown in parentheses.

Grazing incidence wide-angle X-ray scattering (GI-WAXS) measurements were performed to reveal the morphology of the films. For the pristine SMAs, both C8-ITCC and C8-ITCC-Cl show strong (010) diffraction peaks in the OOP direction (qz=1.78 Å-1), indicative of their preferentially "face-on" orientation. Although similar lamellar (20.93 Å) and π-π stacking distances (3.53 Å) for both SMAs were determined, C8-ITCC-Cl exhibited a larger coherence length (CL) compared with C8-ITCC (99.2 vs 75.4 Å for lamellar stacking, and 23.6 vs 21.7 Å for π-π stacking). The enhanced molecular packing of C8-ITCC-Cl was preserved when blended with PBDB-TF. Interestingly, a (010) CL of 37.68 Å was observed for the PBDB-TF blended with C8-ITCC-Cl, which is nearly the double of that for the PBDB-TF blended with C8-ITCC (19.49 Å). This is in agreement with the observed higher hole and electron mobility of the PBDB-TF:C8-ITCC-Cl film ($\mu_h/\mu_e$=9.1/6.7× 10-4 cm$^2$V$^{-1}$ s$^{-1}$) than that of C8-ITCC ($\mu_h/\mu_e$=6.7/2.7× 10-4 cm$^2$V$^{-1}$ s$^{-1}$) measured by the space-charge-limited current (SCLC) method. The GIWAXS and mobility results reflect that the introduction of the chlorine atoms on the thiophene end group facilitates molecular packing in both lamellar and π-π stacking directions, and thus builds up a more efficient charge transport channel in the solar cell devices.

Having determined the molecular packing of C8-ITCC and C8-ITCC-Cl-based blends, we further utilized resonant soft X-ray scattering (RSoXS) to investigate their nano-scale phase segregation. It is found that the RSoXS profile shifted towards a higher q when replacing C8-ITCC with C8-ITCC-Cl in the blend. In addition, the domain sizes, which are half of the characteristic mode length scale (domain spacing, $\zeta=2\pi/q$), are determined to be 66.8 and 31.4 nm for the PBDB-TF:C8-ITCC and PBDB-TF:C8-ITCC-Cl blends, respectively. The surprisingly large domain size of PBDB-TF:C8-ITCC could be responsible for its lower PL quenching and reduced device performance. Notably, the polymer (010) CL of the PBDB-TF:C8-ITCC blend is only about half of that of the PBDB-TF:C8-ITCC-Cl blend, implying that this material combination may excessively intermix and cannot form phase segregation in the ideal scale for bulk-heterojunction OSCs. To test this hypothesis, we examined the domain purity of the two blends, which is proportional to the root square of the integrated scattering intensity (ISI). The average domain purities of the PBDB-TF:C8-ITCC and PBDB-TF:C8-ITCC-Cl blends were calculated to be 0.81 and 1.00, respectively. Indeed, the PBDB-TF:C8-ITCC-Cl blend formed purer domains compared with the PBDB-TF:C8-ITCC one, which suppresses bimolecular recombination.

Example 5—Synthetic Route to ITCPTC and MeIC

After cooling to room temperature, the mixture was poured into methanol (100 mL) and filtered. The residue was purified by column chromatography on silica gel using petroleum ether/dichloromethane (v/v=1/1) as eluent, yielding a dark blue solid (157 mg, 91%). $^1$H NMR (400 MHz, CDCl$_3$): δ 8.73 (s, 2H), 8.30 (d, J=2.2 Hz, 2H), 8.10 (s, 2H), 7.86 (d, J=2.2 Hz, 2H), 7.57 (s, 2H), 7.13 (d, J=8.3 Hz, 8H), 7.06 (d, J=8.3 Hz, 8H), 2.55-2.42 (m, 8H), 1.59-1.45 (m, 8H), 1.34-1.13 (m, 24H), 0.79 (t, J=6.7 Hz, 12H). $^{13}$C NMR (100 MHz, CDCl$_3$): δ 181.32, 156.75, 155.75, 153.24, 147.71, 143.78, 142.55, 142.15, 139.64, 139.48, 138.88, 137.03, 128.89, 128.73, 127.88, 125.57, 118.61, 115.03, 114.29, 67.69, 63.20, 35.63, 31.72, 31.31, 29.74, 29.22, 27.32, 22.62, 14.114. HRMS (ESI) m/z: [M$^+$1] calcd. for C$_{90}$H$_{78}$N$_4$O$_2$S$_6$, 1439.4527; found, 1439.4482.

Example 5b—Synthesis of MeIC

IT-CHO (200 mg, 0.19 mmol), compound CPTCN-Me (170 mg, 0.8 mmol), chloroform (30 mL), and pyridine (1 mL) were added to a two-necked round-bottomed flask. The mixture was deoxygenated with nitrogen for 30 min and then refluxed for 12 h. After cooling to room temperature, the mixture was poured into methanol (200 mL) and filtered. The residue was purified by column chromatography on silica gel using petroleum ether/dichloromethane (1:2) as

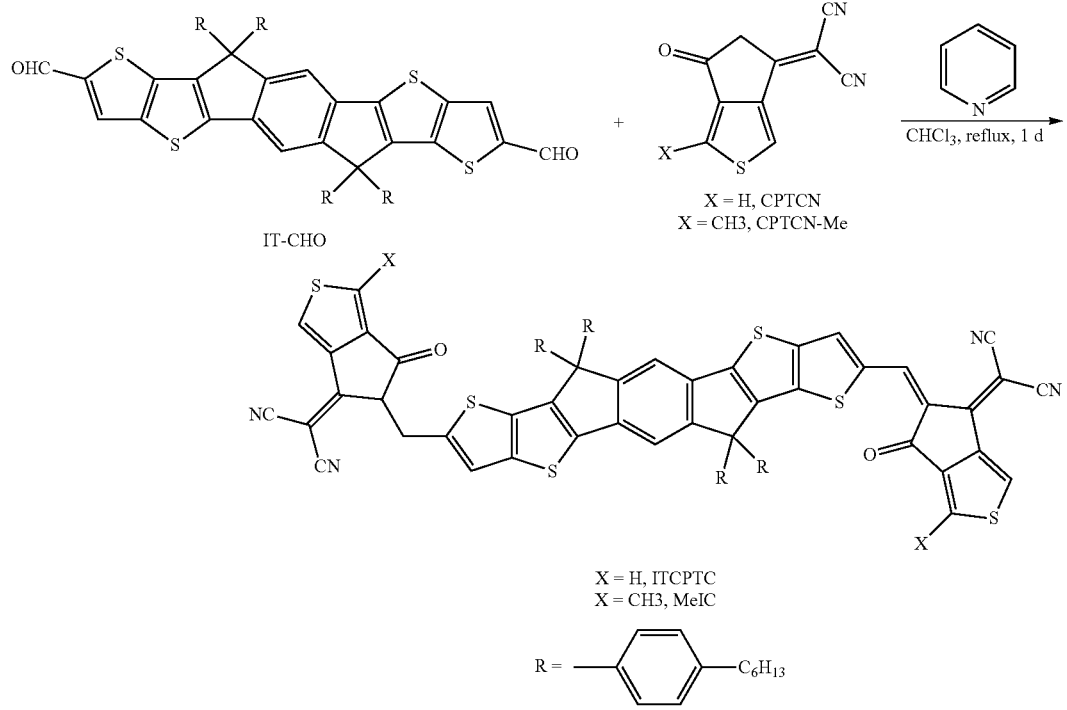

Example 5a—Synthesis of ITCPTC

IT-CHO (129 mg, 0.12 mmol), CPTCN (100 mg, 0.5 mmol), chloroform (10 mL) were placed in a two-necked round-bottomed flask. The mixture was deoxygenated with argon for 30 min, then pyridine (0.1 mL) was added and refluxed at 80° C. for 12 h.

eluent, yielding a dark blue solid (253 mg, 92%). $^1$H NMR (CDCl$_3$, 400 MHz): δ [ppm]: 8.72 (s, 2H), 8.21 (s, 2H), 8.09 (s, 2H), 7.62 (s, 2H), 7.23 (d, J=8.0 Hz, 8H), 7.15 (d, J=8.0 Hz, 8H), 2.78 (s, 6H), 2.62-2.48 (m, 8H), 1.65-1.53 (m, 8H), 1.35-1.23 (m, 24H), 0.92-0.83 (m, 12H). $^{13}$C NMR (100 MHz, CDCl$_3$): δ [ppm]: 182.21, 155.94, 155.66, 152.79, 147.65, 147.09, 144.74, 143.80, 142.53, 142.22, 139.54, 137.10, 136.93, 136.56, 129.68, 128.92, 127.93, 125.03, 118.54, 115.06, 114.47, 67.18, 63.31, 35.66, 31.74, 31.29, 29.23, 22.63, 14.13, 13.63. MS (MALDI-TOF): calcd for ($C_{92}H_{82}N_4O_2S_6$), 1466.5; found, 1466.9. Elemental anal. calcd for $C_{92}H_{82}N_4O_2S_6$: C, 75.27; H, 5.63; N, 3.82. Found: C, 75.24; H, 5.22; N 3.71.

In this example, a novel small molecule acceptor MeIC with a methylated end-capping group Me-CPTCN was developed. Compared to its unmethylated counterpart (ITCPTC), MeIC exhibits higher-lying LUMO level, stronger crystallinity and absorption in the region of 520-740 nm (FIG. 1b). The MeIC-based PSC with J71 (FIG. 5a) as donor achieved a PCE of 12.54% with a JSC of 18.41 mA/cm$^2$ (FIG. 5 and Table 2), significantly higher than those of the device based on J71 and non-methylated ITCPTC (11.63% with JSC of 17.52 mA/cm$^2$). The higher JSC of the PSC based on J71:MeIC can be attributed to more balanced μh/μe, higher charge dissociation probability and charge collection efficiency, better molecular packing and more suitable phase separation properties. These results revealed that the introducing of methyl substituents does not only raise the LUMO level value, but also significantly affect the molecular interactions and packing in thin film. Such a minor modification that leads to the significant improvement of the photovoltaic performance is a very exciting discovery, indicative of new insights in the development of nonfullerene acceptors.

Example 6—Synthetic Route to ITC-2Cl silica gel using petroleum ether/dichloromethane (1:2) as eluent, yielding a dark blue solid (243 mg, 85%). $^1$H NMR (CDCl$_3$, 400 MHz): δ [ppm]: 8.78 (s, 2H), 8.27 (s, 4H), 7.63 (s, 2H), 7.62 (s, 2H), 7.21 (d, J=8.0 Hz, 8H), 7.14 (d, J=8.0 Hz, 8H), 2.62-2.48 (m, 8H), 1.65-1.57 (m, 8H), 1.35-1.20 (m, 24H), 0.92-0.82 (m, 12H). $^{13}$C NMR (100 MHz, CDCl$_3$): δ [ppm]: 180.29, 155.86, 154.65, 153.86, 147.79, 142.61, 142.51, 139.70, 138.77, 138.74, 136.99, 128.92, 128.42, 127.83, 118.70, 114.80, 114.26, 114.14, 67.48, 63.26, 35.62, 31.70, 31.28, 29.21, 22.59, 14.11. HRMS (ESI): calcd for [$C_{90}H_{76}Cl_2N_4O_2S_6$] (M*$^+$H)$^+$: Calc. m/z: 1506.3670, found: 1506.3698.

A new chlorinated nonfullerene acceptor (ITC-2Cl) with chlorinated thiophene-fused end groups was developed. In comparison with the unchlorinated counterpart (ITCPTC in FIG. 6a), the introduction of Cl improves not only the electronic properties by red-shifting the absorption spectra (FIG. 6b) and deepening the LUMO energy levels, but also the molecular packing and thus thin-film morphology. The PM6:ITC-2Cl based device yields a significantly higher PCE (13.6% in FIG. 6c) with a lower Eloss (0.67 eV) than the ITCPTC-based device (PCE of 12.3% with Eloss of 0.70 eV). More importantly, compared to the archetypal nonfullerene acceptors such as IT-4F (PCE of 12.9% with Eloss of

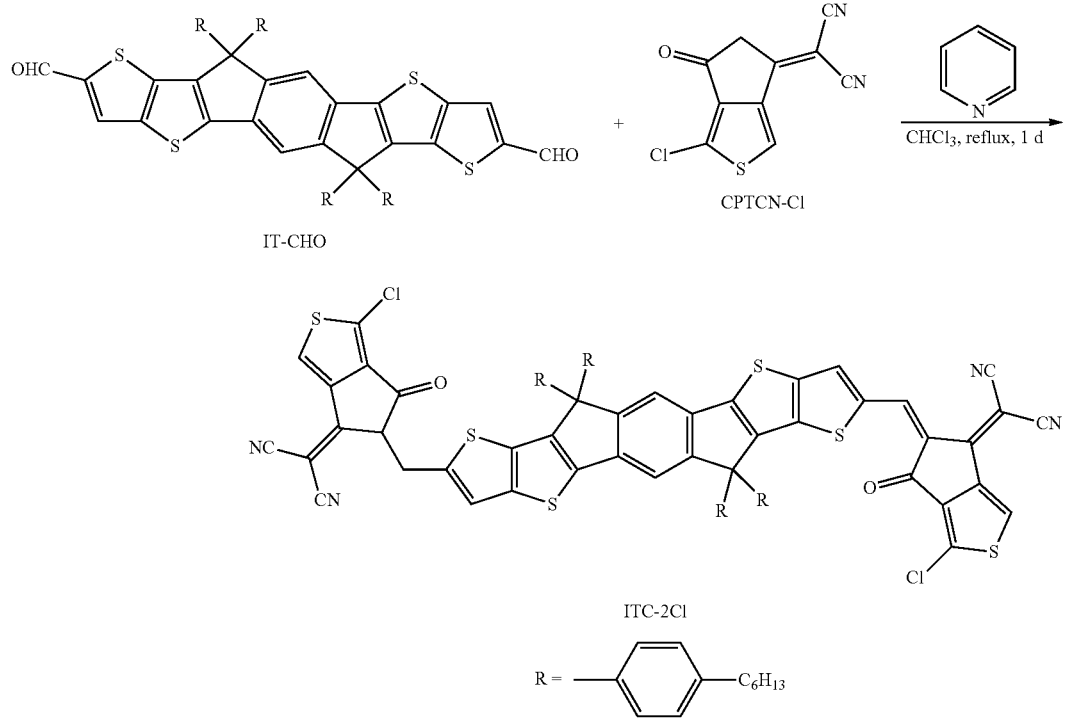

IT-CHO (200 mg, 0.19 mmol), CPTCN-Cl (187 mg, 0.8 mmol), chloroform (30 mL), and pyridine (1 mL) were added to a two-necked round-bottomed flask. The mixture was deoxygenated with nitrogen for 30 min and then refluxed for 24 h. After cooling to room temperature, the mixture was poured into methanol (200 mL) and filtered. The residue was purified by column chromatography on 0.73 eV) and IT-4Cl (PCE of 12.7% with Eloss of 0.76 eV), the ITC-2Cl-based device shows a higher PCE and a lower Eloss.

In order to figure out the reason why the ITC-2Cl-based devices achieved the lower Eloss relative to those of the ITCPTC-, IT-4F-IT-4Cl-based devices, we performed Fourier-transform photocurrent spectroscopy external quantum efficiency (FTPS-EQE) and EL spectra (FIG. 7). Relevant calculated data are summarized in Table 2. Specification of the three sources of Eloss follows the following equation:

$$E_{loss} = (E_{gap} - qE_{CT}) + (q\Delta V_{rad\ oc}) + (q\Delta V_{non\text{-}rad\ oc}) = \Delta E_1 + \Delta E_2 + \Delta E_3 \quad (5)$$

To estimate the energy of the charge transport state, we have performed FTPS-EQE measurement, as shown in FIG. 7. The lower energy part of the EQE spectra (the CT state manifold) can be fitted by Marcus theory to estimate the energy of the CT state.

$$EQEPV(E) = \frac{f}{E\sqrt{4\pi\lambda kT}} \exp\left(\frac{-(E_{CT} + \lambda - E)^2}{4\lambda kT}\right)$$

where k is the Boltzmann constant, T is absolute temperature, $\lambda$ is the reorganization energy and f is the oscillator absorption strength, proportional to the donor/acceptor interface area.

TABLE 2

Summary of parameters measured and calculated from FTPS-EQE and EL.

| Device | $E_{gap}$ (eV) | $V_{oc}$ (V) | $E_{loss}$ (eV) | $E_{CT}$ (V) | $\Delta E_1 = E_{gap} - qE_{CT}$ (eV) | $V_{oc}^{rad}$ (V) | $\Delta E_2 = q\Delta V_{oc}^{rad}$ (eV) | $\Delta E_3 = q\Delta V_{rad\ oc}^{non\text{-}}$ (eV) |
|---|---|---|---|---|---|---|---|---|
| ITCPTC | 1.65 | 0.95 | 0.70 | 1.54 | 0.11 | 1.309 | 0.231 | 0.359 |
| ITC-2Cl | 1.58 | 0.91 | 0.67 | 1.42 | 0.16 | 1.233 | 0.187 | 0.323 |
| IT-4F | 1.60 | 0.87 | 0.73 | 1.38 | 0.22 | 1.236 | 0.144 | 0.366 |
| IT-4Cl | 1.56 | 0.80 | 0.76 | 1.28 | 0.28 | 1.207 | 0.073 | 0.407 |

As shown in Table 2, as the $E_{gopt}$ of the acceptors gradually decreases, ECT gradually decreases but in contrast $\Delta E1$ increases in these four systems. The changes in $\Delta E1$ are approximately 0.11-0.28 eV, which alone cannot explain the difference in VOC distances. Radiative recombination loss ($\Delta E2$) values are depended on the absorption below the Egopt, which can be reduced from the $\Delta ECT$ values. $\Delta E2$ values in these four systems are 0.231 eV for PM6:ITCPTC system, 0.187 eV for PM6:ITC-2Cl system, 0.144 eV for PM6:IT-4F system, and 0.073 eV for PM6:IT-4Cl system, respectively. The final part of the nonradiative recombination loss ($\Delta E3$) is obtained by subtracting $\Delta Vrad$ oc from the measured qVOC. The ITC-2Cl-based device yields the lowest $\Delta E3$ (0.323 eV) among the four type devices. As a result, ITC-2Cl based device, compared with the PM6:ITCPTC system, reduced the radiative and non-radiative recombination loss, and thus led to a lower Eloss. In addition, the Eloss of PM6:ITC-2Cl system is also lower than those of the IT-4F- and IT-4Cl-based devices (see Table 2), the lowest Eloss in ITC-2Cl-based device should be attributed to suppress non-radiative recombination loss and unfavorable charge-transfer state.

Example 7—Synthetic Route to ITC-2 W, ITC-2Br1, and ITC-2Br2

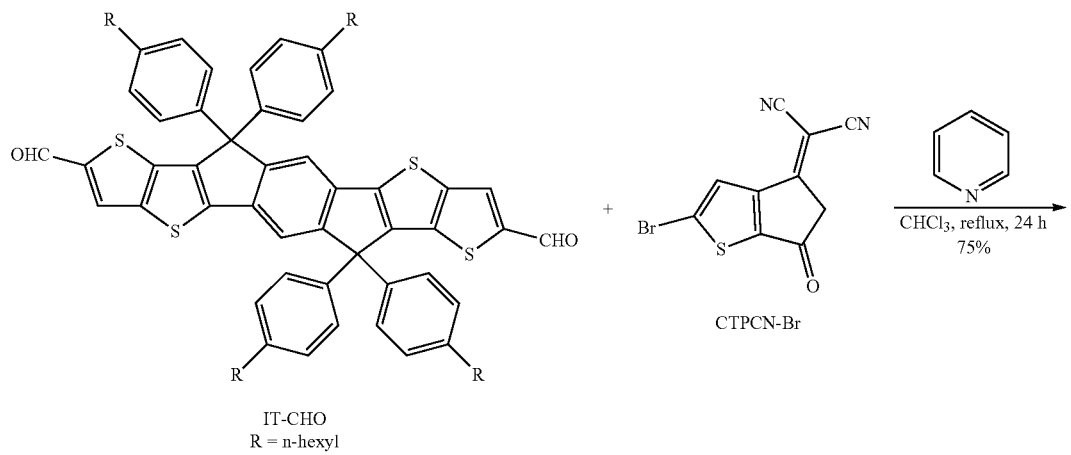

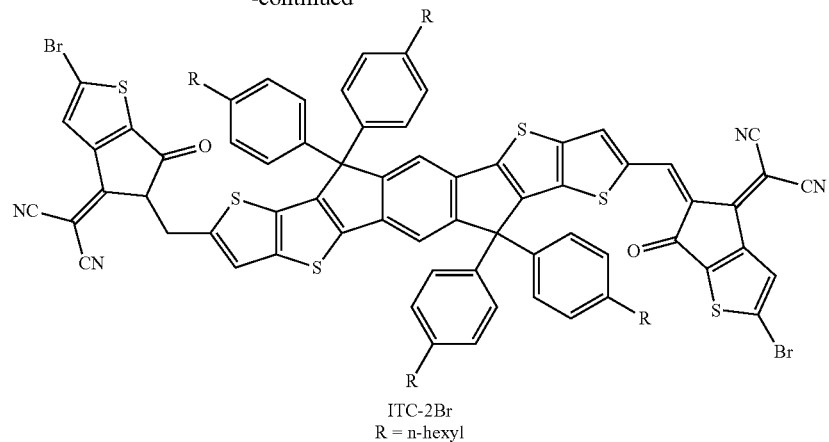
ITC-2Br
R = n-hexyl
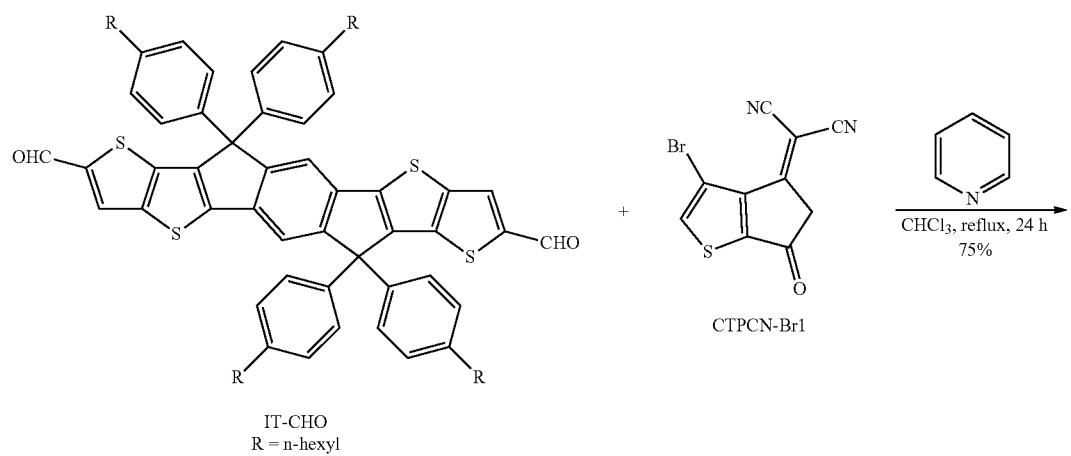
IT-CHO
R = n-hexyl
CTPCN-Br1
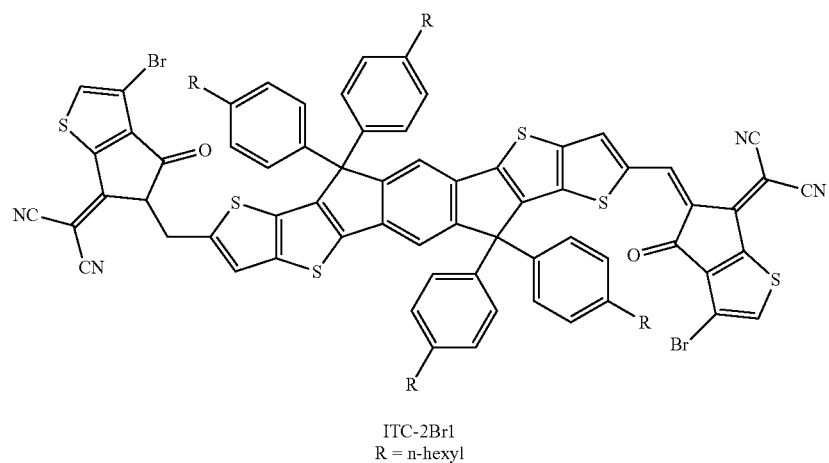
ITC-2Br1
R = n-hexyl

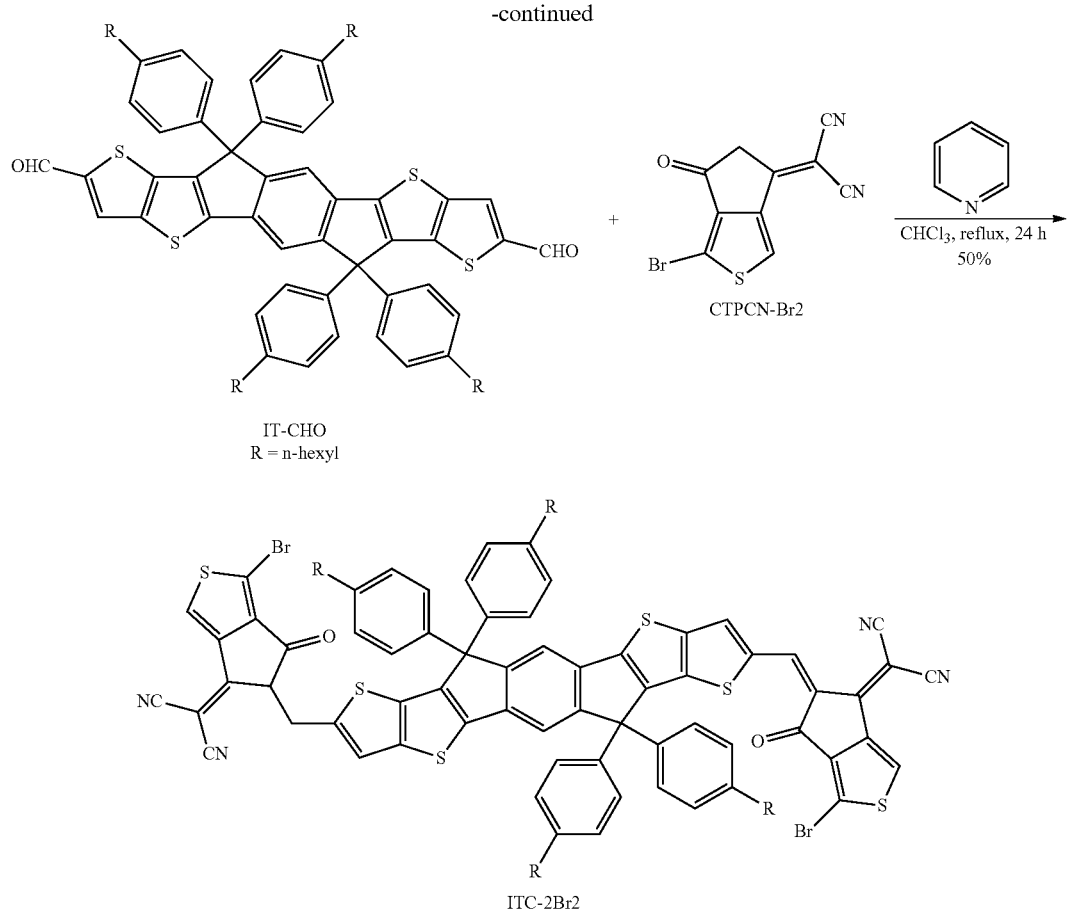

Example 7a—Synthesis of ITC-2Br

IT-CHO (200 mg, 0.19 mmol), CPTCN-Br (213 mg, 0.76 mmol), chloroform (30 mL), and pyridine (1 mL) were added to a two-necked round-bottomed flask. The mixture was deoxygenated with nitrogen for 30 min and then refluxed for 24 h. After cooling to room temperature, the mixture was poured into methanol (200 mL) and filtered. The residue was purified by column chromatography on silica gel using petroleum ether/dichloromethane (2:3) as eluent, yielding a dark blue solid (182 mg, yield: 75%). $^1$H NMR (CDCl$_3$, 400 MHz): δ [ppm]: 8.62 (s, 2H), 8.11 (s, 2H), 7.97 (s, 2H), 7.62 (s, 2H), 7.19 (d, J=8.0 Hz, 8H), 7.13 (d, J=8.0 Hz, 8H), 2.61-2.51 (m, 8H), 1.67-1.57 (m, 8H), 1.38-1.21 (m, 24H), 0.93-0.81 (m, 12H). $^{13}$C NMR (100 MHz, CDCl$_3$): δ [ppm]: 179.59, 155.43, 152.12, 151.26, 148.08, 147.43, 146.30, 143.22, 142.45, 138.97, 138.46, 136.84, 136.72, 136.16, 128.95, 127.85, 126.05, 123.35, 118.39, 113.97, 113.45, 69.83, 63.13, 35.59, 31.69, 31.27, 29.18, 22.59, 14.11. HRMS (ESI): calcd for [C$_{90}$H$_{76}$Br$_2$N$_4$O$_2$S$_6$] (M*+H)$^+$: Calc. m/z: 1594.2659, found: 1594.2655.

Example 7b—Synthesis of ITC-2Br1

The synthetic route of ITC-2Br1 is similar to that of ITC-2Br, excepting for using CPTCN-Br1 to replace CPTCN-Br. The black precipitate was filtered and purified by column chromatography, finally ITC-2Br1 was obtained (184 mg, yield: 75%). $^1$H NMR (CDCl$_3$, 400 MHz): δ [ppm]: 8.60 (s, 2H), 8.22 (s, 2H), 7.68 (s, 2H), 7.62 (s, 2H), 7.21 (d, J=8.0 Hz, 8H), 7.14 (d, J=8.0 Hz, 8H), 2.62-2.54 (m, 8H), 1.69-1.56 (m, 8H), 1.39-1.20 (m, 24H), 0.94-0.79 (m, 12H). $^{13}$C NMR (100 MHz, CDCl$_3$): δ [ppm]: 180.68, 155.49, 155.36, 152.81, 152.46, 147.49, 145.33, 143.57, 142.50, 138.93, 138.34, 136.90, 136.79, 136.20, 128.87, 127.86, 124.07, 118.45, 114.00, 113.27, 106.80, 68.02, 63.22, 35.62, 31.70, 31.28, 29.21, 22.59, 14.11. HRMS (ESI): calcd for [C$_{90}$H$_{76}$Br$_2$N$_4$O$_2$S$_6$] (M*+H)+: Calc. m/z: 1594.2659, found: 1594.2657.

Example 7c—Synthesis of ITC-2Br2

The synthetic route of ITC-2Br2 is similar to that of ITC-2Br, excepting for using CPTCN-Br2 to replace CPTCN-Br. The black precipitate was filtered and purified by column chromatography, finally ITC-Br1 was obtained (242 mg, 80%). $^1$H NMR (CDCl$_3$, 400 MHz): δ [ppm]: 8.76 (s, 2H), 8.42 (s, 2H), 8.37 (s, 2H), 7.63 (s, 2H), 7.21 (d, J=8.0 Hz, 8H), 7.14 (d, J=9.2 Hz, 8H), 2.60-2.50 (m, 8H), 1.68-1.57 (m, 8H), 1.36-1.20 (m, 24H), 0.91-0.80 (m, 12H). $^{13}$C NMR (100 MHz, CDCl$_3$): δ [ppm]: 180.31, 155.88, 154.67, 153.88, 147.81, 142.63, 142.53, 139.72, 138.79, 138.76, 137.01, 128.94, 127.85, 118.71, 67.50, 63.28, 35.63, 31.71, 31.30, 29.22, 22.61, 14.13. HRMS (ESI): calcd for [C$_{90}$H$_{76}$Br$_2$N$_4$O$_2$S$_6$] (M*+H)$^+$: Calc. m/z: 1594.2659, found: 1594.2662.

TABLE 3

The photovoltaic parameters of the optimized OSCs based on PM6: acceptors under standard AM 1.5 G illumination, 100 mW cm$^{-2}$. The average values and standard deviations were obtained from 20 devices.

| Devices | $V_{OC}$ (V) | $J_{SC}$ (mA cm$^{-2}$) | FF | PCE$_{max}$ (PCE$_{avg}$) % |
|---|---|---|---|---|
| PM6/ITC-2Br | 1.03 | 15.4 | 0.688 | 10.9 (10.7 ± 0.1) |
| PM6/ITC-2Br1 | 1.01 | 16.6 | 0.706 | 11.9 (11.7 ± 0.2) |
| PM6/ITC-2Br2 | 0.90 | 19.8 | 0.738 | 13.1 (12.9 ± 0.2) |

In this example, we developed three isomeric A-D-A small molecular acceptors (ITC-2Br, ITC-2Br1 and ITC-2Br2). Regarding the acceptors of ITC-2Br and ITC-2Br1, the change of the bromine substituent group on the thiophene ring has minor impact on the physicochemical properties and photovoltaic performance. However, as for ITC-2Br and ITC-2Br2, the change in the fused sites on the thiophene has significant effect on absorption, energy levels and photovoltaic performance. From ITC-2Br, ITC-2Br1 to ITC-2Br2, the absorption peak is gradually red-shifted (from 682, 692 to 746 nm (FIG. 8a)) along with constantly reduced LUMO energy levels (from −3.93, −3.95 to −4.02 eV (FIG. 8b)), and the electron mobility and molecular packing are gradually improved. Consequently, the ITC-2Br2-based polymer solar cells (PSCs) yields a significantly higher power energy efficiency of 13.1% than those of the device based on ITC-2Br-(10.9%) and ITC-2Br1 (11.9%) (FIG. 8c and Table 3). The JSC and FF exhibit a monotonic increase similar to the trend of PCE, from the ITC-2Br-, ITC-2Br1- to the ITC-2Br2-based device (FIG. 8d). The highest JSC and FF for the ITC-2Br2-based device should be attributed to the strongest and significantly redshifted absorption of ITC-2Br2, enhanced crystallinity, preferable molecular orientation, proper phase separation, high charge mobilities and balanced charge transport of PM6:ITC-2Br2 blend film. These results shed light on the structure-property relationship caused by end group isomerization, which is beneficial for developing highly efficient SMAs.

Example 8—Synthetic Route to IDTPC

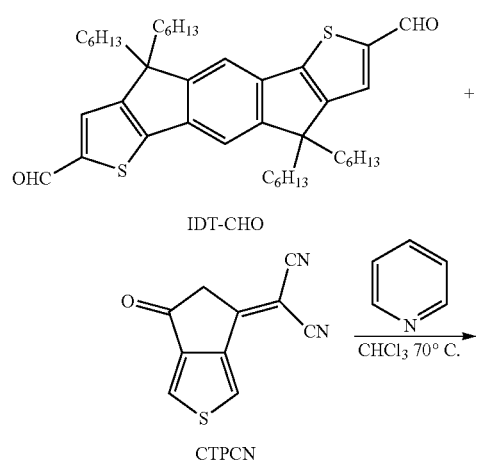

IDT-CHO

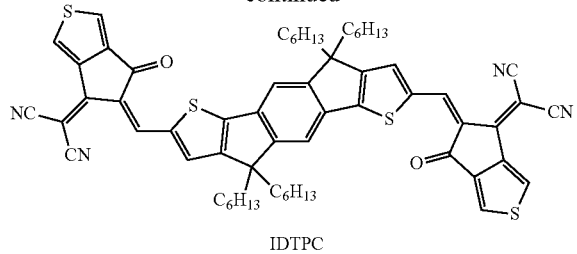

CTPCN

-continued

IDTPC

Materials IDT-CHO (0.130 g, 0.2 mmol) and CTPCN (0.200 g, 1 mmol) were added to a 100 ml two-necked flask, successively. After being flushed by a gentle stream of dry nitrogen for 15 min, chloroform (30 ml) was added and the two compounds were fully dissolved by stirring for a while. Then pyridine (0.6 ml) was added and the solution was slowly turned into green. The mixture was refluxed at 65° C. for 20 hours, and most of the solvent was evaporated. The crude product was washed by methanol to remove the excessive CTPCN, and further purified by column chromatography with n-hexane:CH$_2$Cl$_2$ (2:1) as the eluent to obtain the material IDTPC as the dark blue solid (0.184 g, 90% yield). $^1$H NMR (CDCl$_3$, 400 MHz): δ [ppm]: 8.91 (s, 2H), 8.40 (s, 2H), 7.96 (s, 2H), 7.70 (s, 2H), 7.59 (d, J=8.0 Hz, 8H), 2.10-2.01 (m, 8H), 1.28-1.15 (m, 24H), 0.86-0.70 (m, 20H). $^{13}$C NMR (100 MHz, CDCl$_3$): δ [ppm]: 181.48, 160.92, 157.65, 156.75, 142.50, 142.30, 141.20, 139.73, 138.06, 137.94, 128.17, 127.74, 125.48, 116.12, 115.18, 114.56, 54.35, 39.10, 31.62, 31.54, 29.56, 29.46, 24.36, 22.69, 22.57, 14.17, 14.03. MS (MALDI-TOF): calcd for (C$_{62}$H$_{62}$N$_4$O$_2$S$_4$), 1022.38; found, 1022.59. Elemental anal. calcd for C$_{62}$H$_{62}$N$_4$O$_2$S$_4$: C, 72.76; H, 6.11; N, 5.47. Found: C, 72.34; H, 6.29; N, 5.79.

A new n-type organic semiconductor (n-OS) acceptor IDTPC (FIG. 9b) with n-hexyl side chains was developed. Compared to side chains with 4-hexylphenyl counterparts (IDTCN), such a design endowed the acceptor of IDTPC with higher electron mobility, lower band gap and more ordered face-on molecular packing (FIG. 9d). Therefore, the IDTPC-based PSCs with a wide bandgap polymer PTQ10 as donor exhibited the maximum power conversion efficiency (PCE) of 12.2%, a surprising near 65% improvement in PCE relative to the IDTCN-based control device.

Apart from good photovoltaic performance, thickness-insensitive behavior for the film thickness of active layers in the range 100-500 nm is also crucial for large-scale fabrication of PSCs. Thus we systematically fabricated the PTQ10:IDTPC-based PSCs with varied active-layer thicknesses (ranging from 70 to 505 nm). As shown in FIG. 10c, VOC values of the devices slightly decreased for the active-layer thickness thicker than 110 nm. As for JSC, when the film thickness was increased from 110 nm to 145 nm, a significantly increase of JSC was observed, and thereafter, the JSC remained within 17.50±0.70 mA cm$^{-2}$. Although the FF gradually decreased when the film thickness exceeded 110 nm, a nice FF of 0.613 was still obtained for the device with a film thickness of 400 nm. Therefore, PCEs over 10% were achieved for the thickness of the active layer varying from 70 to 400 nm. What is more, the device based on IDTPC still displayed a high PCE of 9.2% when the film thickness reached 505 nm, corresponding to 75% of the peak value, which is the best performance relative to the respective PSCs reported so far. These results revealed that PTQ10:IDTPC blend films exhibited great potential for large-area manufacturing of PSCs by roll-to-roll process.

What is claimed:

1. A compound of Formula 1:

wherein Ar$^1$ is selected from the group consisting of:

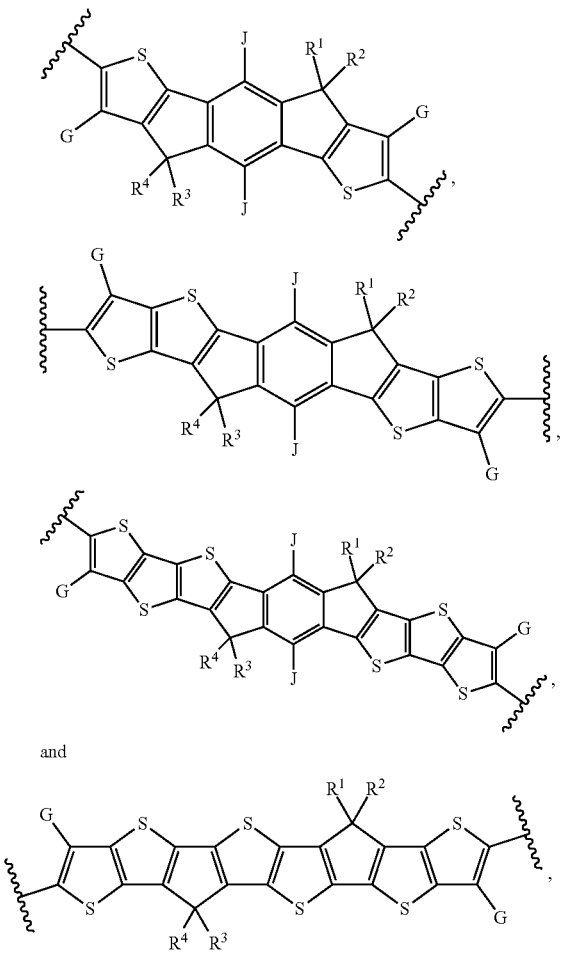

wherein each of R$^1$, R$^2$, R$^3$, and R$^4$ is an alkyl group selected from the group consisting of C$_2$-C$_{40}$ straight-chain alkyl, C$_3$-C$_{40}$ branched alkyl, C$_3$-C$_{40}$ cyclic alkyl, C$_2$-C$_{40}$ alkyl aryl, and C$_2$-C$_{40}$ alkyl heteroaryl;
J is hydrogen or an alkyl group;
G is hydrogen, F, Cl, or an alkyl group; and Ar$^2$ is selected from the group consisting of:

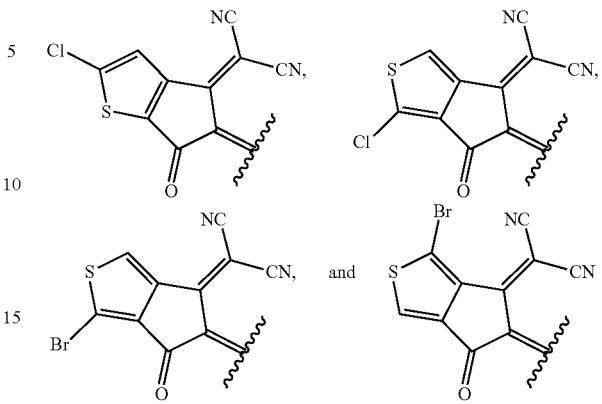

2. The compound of claim 1, wherein J is hydrogen; and G is hydrogen.

3. The compound of claim 1, wherein each of R$^1$, R$^2$, R$^3$, and R$^4$ is an alkyl group selected from the group consisting of C$_2$-C$_{40}$ straight-chain alkyl, C$_3$-C$_{40}$ branched alkyl, and C$_2$-C$_{40}$ alkyl aryl.

4. The compound of claim 1, wherein J is hydrogen; G is hydrogen; and each of R$^1$, R$^2$, R$^3$, and R$^4$ is an alkyl group selected from the from the group consisting of C$_2$-C$_{40}$ straight-chain alkyl and C$_2$-C$_{40}$ alkyl aryl.

5. The compound of claim 1, wherein Ar$^1$ is

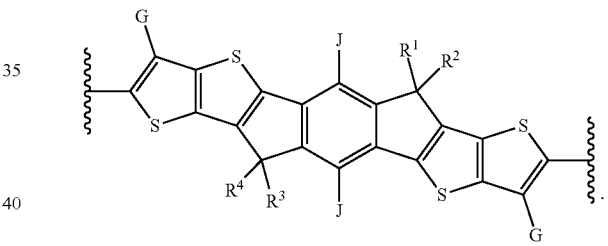

6. The compound of claim 5, wherein J is hydrogen; and each of R$^1$, R$^2$, R$^3$, and R$^4$ is an alkyl group selected from the group consisting of C$_2$-C$_{40}$ straight-chain alkyl, C$_3$-C$_{40}$ branched alkyl, C$_3$-C$_{40}$ cyclic alkyl, C$_2$-C$_{40}$ alkyl aryl, and C$_2$-C$_{40}$ alkyl heteroaryl.

7. The compound of claim 1, wherein Ar$^1$ is:

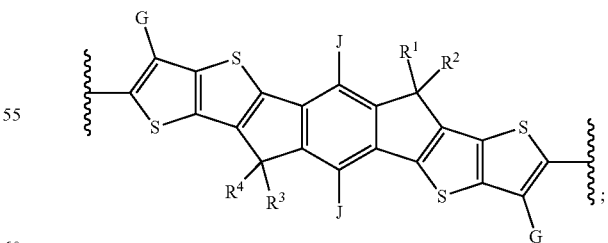

G is hydrogen; each of R$^1$, R$^2$, R$^3$, and R$^4$ is an alkyl group selected from the group consisting of C$_2$-C$_{40}$ straight-chain alkyl and C$_2$-C$_{40}$ alkyl aryl; and J is hydrogen.

8. The compound of claim 1, wherein the compound is selected from the group consisting of

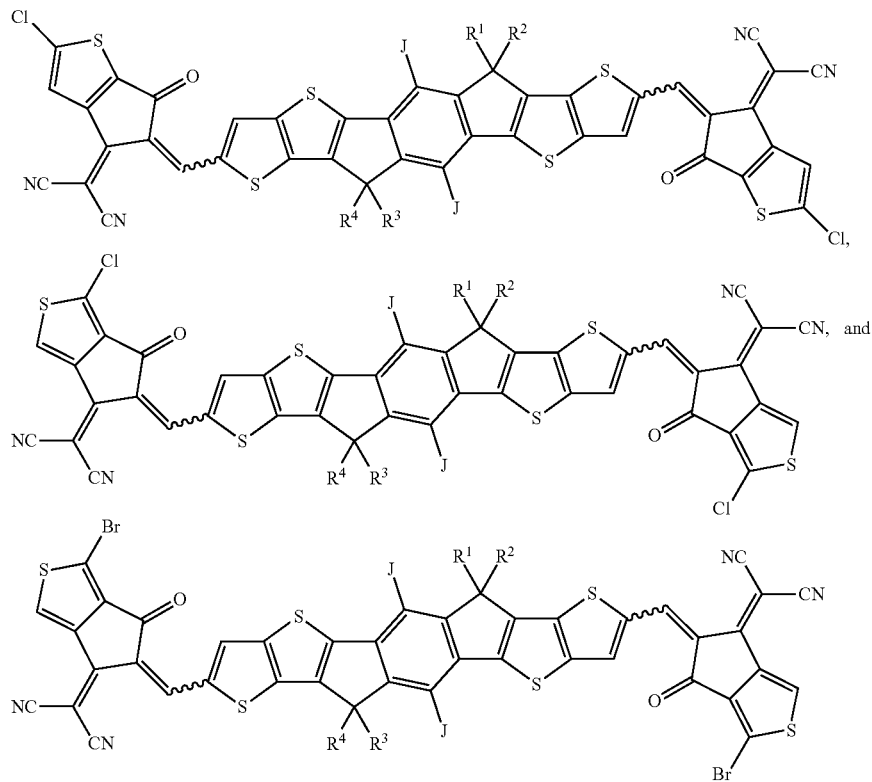

wherein each of $R^1$, $R^2$, $R^3$, and $R^4$ is an alkyl group selected from the group consisting of $C_2$-$C_{40}$ straight-chain alkyl, $C_3$-$C_{40}$ branched alkyl, $C_3$-$C_{40}$ cyclic alkyl, $C_2$-$C_{40}$ alkyl aryl, and $C_2$-$C_{40}$ alkyl heteroaryl; and J is hydrogen or an alkyl group.

9. The compound of claim 8, wherein each of $R^1$, $R^2$, $R^3$, and $R^4$ is 4-(n-hexyl)phenyl or n-octyl; and J is hydrogen.

10. A photovoltaic device comprising the compound of claim 1.

11. A photovoltaic device comprising the compound of claim 9.

* * * * *